United States Patent [19]

Chappell et al.

[11] Patent Number: 5,589,619

[45] Date of Patent: *Dec. 31, 1996

[54] PROCESS AND COMPOSITION FOR INCREASING SQUALENE AND STEROL ACCUMULATION IN HIGHER PLANTS

[75] Inventors: Joseph Chappell, Lexington, Ky.; Court A. Saunders, Clarendon Hills; Fred R. Wolf, Naperville, both of Ill.

[73] Assignee: Amoco Corporation, Chicago, Ill.

[*] Notice: The term of this patent shall not extend beyond the expiration date of Pat. No. 5,306,862.

[21] Appl. No.: 308,551

[22] Filed: Dec. 8, 1994

Related U.S. Application Data

[60] Division of Ser. No. 934,374, Aug. 14, 1992, Pat. No. 5,349,126, which is a continuation-in-part of Ser. No. 596,467, Oct. 12, 1990, Pat. No. 5,306,862.

[51] Int. Cl.$^6$ .............................. A01H 5/00; C12N 15/00; C12N 15/82

[52] U.S. Cl. ..................... 800/205; 800/250; 435/69.1; 435/172.3; 435/240.4

[58] Field of Search ................. 435/69.1, 70.1, 435/172.3, 183, 240.4, 320.1; 800/205, 255, 250

[56] References Cited

U.S. PATENT DOCUMENTS

| | | | |
|---|---|---|---|
| 4,956,282 | 9/1990 | Goodman et al. | 435/69.51 |
| 5,306,862 | 4/1994 | Chappell et al. | 800/205 |
| 5,365,017 | 11/1994 | Chappell et al. | 800/205 |

OTHER PUBLICATIONS

Basson et al., *Molecular and Cellular Biology*, 8:3797–3808 (1988).
Klein et al., *Plant Physiol*, 91:440–444 (1989).
Fromm et al., *Nature*, 319:791–793 (1986).
Odell et al., *Nature*, 313 (1985).
Marcotte et al., *Nature*, 335:454–457 (1988).
Fromm et al., *Proc. Natl. Acad. Sci.*, USA, 82:5824–5828 (1985).
Bytebier et al., *Proc. Natl. Acad. Sci.*, 84:5345–5349 (1987).
Klein et al., *Proc. Natl. Acad. Sci.*, 85:8502–8505 (1988).
Berger et al., *Proc. Natl. Acad. Sci.*, 8402–8406 (1989).
Yang et al., *Proc. Natl. Acad. Sci.*, 87:4144–4148 (1990).
Fraley et al., *Proc. Natl. Acad. Sci.*, 80:4803–4807 (1983).
Rine et al., *Proc. Natl. Acad. Sci.*, 80:6750–6754 (1983).
Schardi et al., *Gene* 61:1–11 (1987).
Liscum et al., *The Journal of Biological Chemistry*, 260:522–530 (1985).
Jorgensen et al., *Mol. Gen. Genet*, 207:471–477.
Uchimiya et al., *Mol. Gen. Genet*, 204:204–207 (1986).
Spielman et al., *Mol. Gen. Genet*, 205:34–41 (1986).
Poulsen et al., *Mol. Gen. Genet*, 205:193–200.
Bard et al., *Journal of General Microbiology*, 125:415–420 (1981).
Vasil, I. K., *Bio/Technology*, 8:797 (1990).
Wenzler et al., *Plant Molecular Biology*, 12:41–50 (1989).
Keller et al., *The EMBO Journal*, 8:1309–1314 (1989).
Simpson et al., *Science*, 233:34–38 (1986).
Brown et al., *Journal of Lipid Research*, 21:505–517 (1980).
Caberera et al., *J. Biol. Chem.*, 261(8):3578–3583 (1986).
Hasumi et al., *Eur. J. Biochem.*, 164:547–552 (1987).
Jordan-Stark et al., *J. of Biol Chem.*, 264:17919–17923.
Orci et al., *Cell*, 36:835–845 (1984).
Chin et al., *Proc. Natl. Acad. Sci.*, USA 79:1185–1189.
Goldstein et al., *Nature*, 343:425–430 (1990).
Luskey, K. L., *Molecular and Cellular Biology*, 7(5):1881.
Benfey et al., *Science*, 244:174 (1989).
Langridge et al., *Proc. Natl. Acad. Sci.*, USA, 86:3219.
Mayerhofer et al., *The EMBO Journal*, 10(3):697 (1991).
Toriyama et al. *Biotechnology*, 6:1072 (1988).
Vogeli et al., *Plant Physiol.*, 88(4):1291–1296 (1980).
Caelles et al., *Plant Molecular Biology*, 13:627–638 (1991).
Chappell et al., *Plant Physiology*, (Suppl) 96(1):127 (1991) (Abstract #853).
Narita et al., *The Plant Cell*, 1:181–190 (1989).
Chin et al., *Mol. Cell. Biol.*, 5(4):634–641 (1985).
Learned et al., *Proc. Natl. Acad. Sci. USA*, 86:2779–2783 (1989).
LaGrimini et al., *The Plant Cell*, 2:7–18 (1990).
Shigematsu et al., *Agr. & Biol. Ch.*, 46(11):2877–2879 (1982).
Vaeck et al., *Nature*, 328:33–37 (1987).
Bradford et al., *Can. J. Bot.*, 60:1469–1473 (1982).
Gil et al (1985) Cell 41:249–258.
Downing et al (1980) Biochem Biophys. Res. Comm 94(3):974–979.
Horsch et al (1985) Science 227:1229–1231
Chin et al (1984) Nature 308:613–617.
Chappel et al. (1989) Plant Cell Reports 8:48–52.

*Primary Examiner*—David T. Fox
*Assistant Examiner*—Elizabeth F. McElwain

[57] ABSTRACT

A process of increasing squalene and sterol accumulation in a transgenic plant by increasing the amount of a gene encoding a polypeptide having HMG-CoA reductase activity is disclosed. The amount is preferably increased by transforming plant cells with a recombinant DNA molecule comprising a vector operatively linked to an exogenous DNA segment that encodes a polypeptide having HMG-CoA reductase activity, and a promoter suitable for driving the expression of said polypeptide to form a transformed plant cell and regenerating a transgenic plant from that transformed cell. Also disclosed are a process of increasing pest resistance in a transgenic plant, transgenic plants and transgenic seeds capable of germinating into transgenic plants.

7 Claims, 23 Drawing Sheets

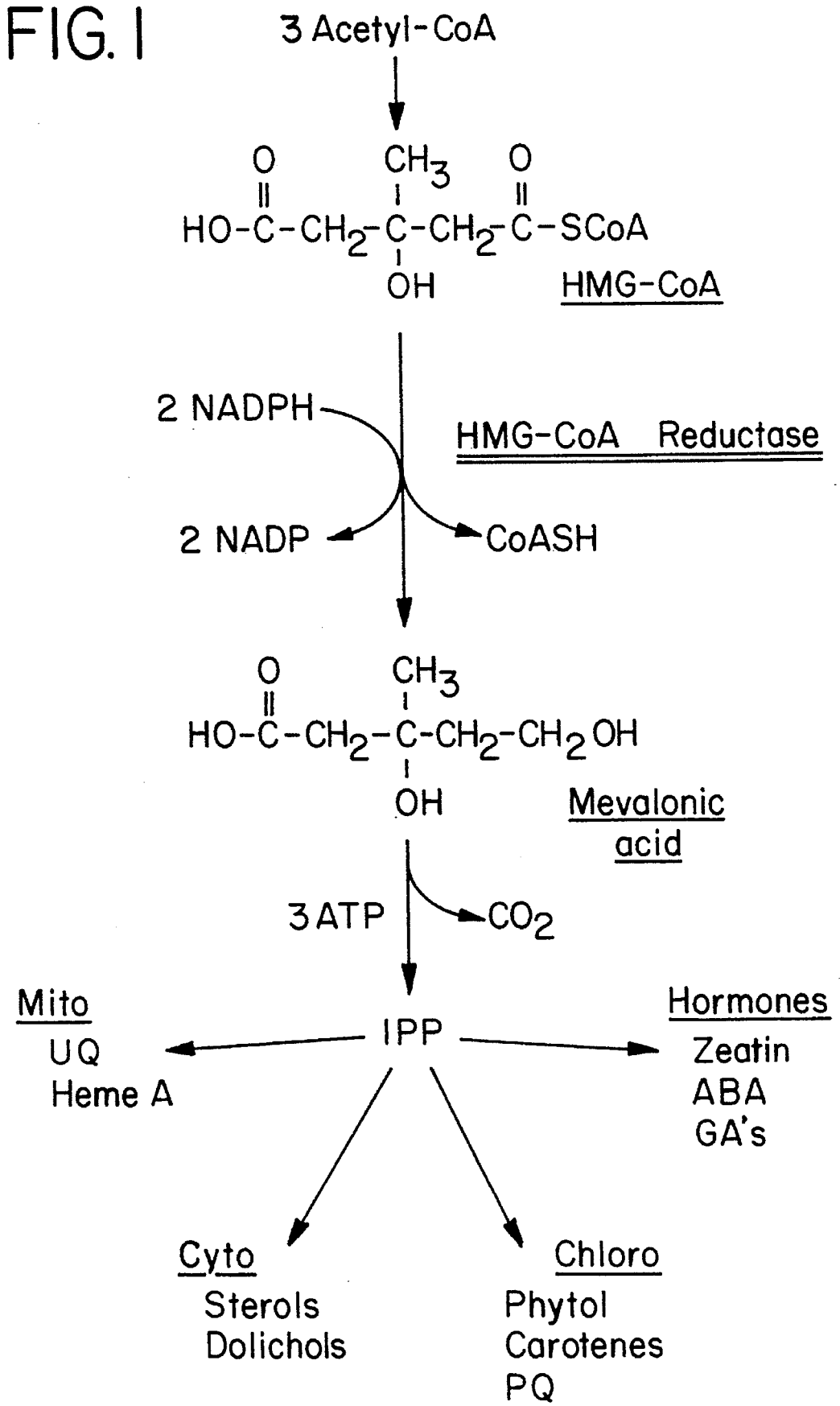

```
TGTATGTCTT GTCTTTCTCC TAAGGGGCGT AGGCTCATTG ATAACTCATG TCCTCACCTT         60

GCACTCCTTT TGGAATTATT TGGTTTGAGT GAAGAAGACC GGACCTTCGA GGTTCGCAAC        120

TTAAACAATA GACTTGTGAG GATCCAGGGA CCGAGTGGCT ACA ATG TTG TCA CGA         175
                                             Met Leu Ser Arg
                                              1

CTT TTC CGT ATG CAT GGC CTC TTT GTG GCC TCC CAT CCC TGG GAA GTT         223
Leu Phe Arg Met His Gly Leu Phe Val Ala Ser His Pro Trp Glu Val
      5                    10                    15                20

ATT GTG GGG ACG GTG ACA CTT ACC ATC TGT ATG ATG TCC ATG AAC ATG         271
Ile Val Gly Thr Val Thr Leu Thr Ile Cys Met Met Ser Met Asn Met
              25                    30                    35

TTC ACT GGC AAC AAG ATC TGT GGT TGG AAT TAC GAG TGC CCA AAA             319
Phe Thr Gly Asn Lys Ile Cys Gly Trp Asn Tyr Glu Cys Pro Lys
      40                    45                    50

TTT GAG GAG GAT GTA TTG AGC AGT GAC ATC ATC ATC CTC ACC ATA ACA         367
Phe Glu Glu Asp Val Leu Ser Ser Asp Ile Ile Ile Leu Thr Ile Thr
              55                    60                    65

CGG TGC ATC GCC ATC CTG TAC ATT TAC TTC CAG TTC CAG AAC TTA CGT         415
Arg Cys Ile Ala Ile Leu Tyr Ile Tyr Phe Gln Phe Gln Asn Leu Arg
      70                    75                    80
```

Figure 2A

| | | | | | | | | | | | | | | | | |
|---|---|---|---|---|---|---|---|---|---|---|---|---|---|---|---|---|
| CAG | CTT | GGG | TCG | AAG | TAT | ATT | TTA | GGT | ATT | GCT | GGC | CTG | TTC | ACA | ATT | 463 |
| Gln | Leu | Gly | Ser | Lys | Tyr | Ile | Leu | Gly | Ile | Ala | Gly | Leu | Phe | Thr | Ile | |
| 85 | | | | | 90 | | | | | 95 | | | | | 100 | |

| | | | | | | | | | | | | | | | | |
|---|---|---|---|---|---|---|---|---|---|---|---|---|---|---|---|---|
| TTC | TCA | AGT | TTT | GTC | TTT | AGT | ACA | GTC | GTC | ATT | CAC | TTC | TTA | GAC | AAA | 511 |
| Phe | Ser | Ser | Phe | Val | Phe | Ser | Thr | Val | Val | Ile | His | Phe | Leu | Asp | Lys | |
| | | 105 | | | | | | | 110 | | | | | 115 | | |

| | | | | | | | | | | | | | | | | |
|---|---|---|---|---|---|---|---|---|---|---|---|---|---|---|---|---|
| GAA | CTG | ACG | GGC | TTA | AAT | GAA | GCT | TTG | CCC | TTT | TTC | CTG | CTT | TTG | ATT | 559 |
| Glu | Leu | Thr | Gly | Leu | Asn | Glu | Ala | Leu | Pro | Phe | Phe | Leu | Leu | Leu | Ile | |
| | | 120 | | | | | 125 | | | | | | 130 | | | |

| | | | | | | | | | | | | | | | | |
|---|---|---|---|---|---|---|---|---|---|---|---|---|---|---|---|---|
| GAC | CTT | TCT | AGA | GCG | AGT | GCA | CTA | GCA | AAG | TTT | GCC | CTA | AGT | TCA | AAC | 607 |
| Asp | Leu | Ser | Arg | Ala | Ser | Ala | Leu | Ala | Lys | Phe | Ala | Leu | Ser | Ser | Asn | |
| | | 135 | | | | | 140 | | | | | | 145 | | | |

| | | | | | | | | | | | | | | | | |
|---|---|---|---|---|---|---|---|---|---|---|---|---|---|---|---|---|
| TCT | CAG | GAT | GAA | GTA | AGG | GAA | AAT | ATA | GCT | CGC | GGA | ATG | GCA | ATT | CTG | 655 |
| Ser | Gln | Asp | Glu | Val | Arg | Glu | Asn | Ile | Ala | Arg | Gly | Met | Ala | Ile | Leu | |
| 150 | | | | | 155 | | | | | 160 | | | | | | |

| | | | | | | | | | | | | | | | | |
|---|---|---|---|---|---|---|---|---|---|---|---|---|---|---|---|---|
| GGC | CCC | ACA | TTC | ACC | CTT | GAT | GCT | CTT | GTG | GAA | TGT | CTT | GTA | ATT | GGA | 703 |
| Gly | Pro | Thr | Phe | Thr | Leu | Asp | Ala | Leu | Val | Glu | Cys | Leu | Val | Ile | Gly | |
| 165 | | | | | 170 | | | | | 175 | | | | | 180 | |

| | | | | | | | | | | | | | | | | |
|---|---|---|---|---|---|---|---|---|---|---|---|---|---|---|---|---|
| GTT | GGC | ACC | ATG | TCA | GGG | GTG | CGT | CAG | CTT | GAA | ATC | ATG | TGC | TGC | TTT | 751 |
| Val | Gly | Thr | Met | Ser | Gly | Val | Arg | Gln | Leu | Glu | Ile | Met | Cys | Cys | Phe | |
| | | | 185 | | | | | 190 | | | | | | 195 | | |

Figure 2B

```
GGC TGC ATG TCT GTG CTT GCC AAC TAC TTC GTG TTC ATG ACA TTT TTC    799
Gly Cys Met Ser Val Leu Ala Asn Tyr Phe Val Phe Met Thr Phe Phe
            200                 205                 210

CCA GCG TGT GTG TCC CTG GTC CTT GTC CTG GAG CTT TCT CGG GAA AGT CGA GAG    847
Pro Ala Cys Val Ser Leu Val Leu Val Leu Glu Leu Ser Arg Glu Ser Arg Glu
            215                 220                 225

GGT CGT CCA ATT TGG CAG CTT AGC CAT TTT GCC CGA GTT TTG GAA GAA    895
Gly Arg Pro Ile Trp Gln Leu Ser His Phe Ala Arg Val Leu Glu Glu
            230                 235                 240

GAA GAG AAT AAA CCA AAC CCT GTA ACC CAA AGG GTC AAG ATG ATT ATG    943
Glu Glu Asn Lys Pro Asn Pro Val Thr Gln Arg Val Lys Met Ile Met
245                 250                 255                 260

TCT TTA GGT TTG GTT CTT GTT CAT GCT CAC AGT CGA TGG ATA GCT GAT    991
Ser Leu Gly Leu Val Leu Val His Ala His Ser Arg Trp Ile Ala Asp
            265                 270                 275

CCT TCC CCT CAG AAT AGC ACA ACA GAA CAT TCT AAA GTC TCC TTG GGA    1039
Pro Ser Pro Gln Asn Ser Thr Thr Glu His Ser Lys Val Ser Leu Gly
            280                 285                 290

CTG GAT GAA GAT GTG TCC AAG AGA ATT GAA CCA AGT GTT TCT CTC TGG    1087
Leu Asp Glu Asp Val Ser Lys Arg Ile Glu Pro Ser Val Ser Leu Trp
295                 300                 305
```

Figure 2C

```
CAG TTT TAT CTC TCC AAG ATG ATC AGC ATG GAC ATT GAA CAA GTG GTT      1135
Gln Phe Tyr Leu Ser Lys Met Ile Ser Met Asp Ile Glu Gln Val Val
310                 315                 320

ACC CTG AGC TTA GCT TTT CTG TTG GCT GTC AAG TAC ATT TTC TTT GAA      1183
Thr Leu Ser Leu Ala Phe Leu Leu Ala Val Lys Tyr Ile Phe Phe Glu
325                 330                 335                 340

CAA GCA GAG ACA GAG TCC ACA CTG TCT TTA AAA AAT CCT ATC ACG TCT      1231
Gln Ala Glu Thr Glu Ser Thr Leu Ser Leu Lys Asn Pro Ile Thr Ser
            345                 350                 355

CCT GTC ACC CTG GTG AGA AGG AGC GAG AAA GCT CCA GAC AAC TGT TGT AGA CGG GAG    1279
Pro Val Thr Leu Val Arg Arg Ser Glu Lys Ala Pro Asp Asn Cys Cys Arg Arg Glu
        360             365             370

CCT GGG GTG AGC CAA GAT AGA AGG AGC GAG AAA GTT GAG GTT ATA AAA CCA TTA GTG    1327
Pro Gly Val Ser Gln Asp Arg Arg Ser Glu Lys Val Glu Val Ile Lys Pro Leu Val
    390             395             400

GTG GAA ACT GAG AGT GCA AGC AGA GCT ACA TTT GTG CTT GGC GCC TCT                1375
Val Glu Thr Glu Ser Ala Ser Arg Ala Thr Phe Val Leu Gly Ala Ser
405                 410                 415                 420
```

Figure 2D

```
GGG ACC AGC CCT CCA GTG GCA GCG AGG ACA CAG GAG CTT GAA ATT GAA    1471
Gly Thr Ser Pro Pro Val Ala Ala Arg Thr Gln Glu Leu Glu Ile Glu
            425                     430                     435

CTC CCC AGT GAG CCT CGG CCT AAT GAA TGT CTG CAG ATA CTG GAG        1519
Leu Pro Ser Glu Pro Arg Pro Asn Glu Cys Leu Gln Ile Leu Glu
            440                     445                     450

AGT GCC GAG AAA GGT GCA AAG TTC CTT AGC GAT GCA GAG ATC ATC CAG    1567
Ser Ala Glu Lys Gly Ala Lys Phe Leu Ser Asp Ala Glu Ile Ile Gln
            455                     460                     465

TTG GTC AAT GCC AAG CAC ATC CCA GCC TAC AAA TTG GAA ACC TTA ATG    1615
Leu Val Asn Ala Lys His Ile Pro Ala Tyr Lys Leu Glu Thr Leu Met
            470                     475                     480

GAA ACT CAT GAA CGT GGT GTA TCT ATT CGC CGG CAG CTC CTC TCC ACA    1663
Glu Thr His Glu Arg Gly Val Ser Ile Arg Arg Gln Leu Leu Ser Thr
            485                     490                     495                     500

AAG CTT CCA GAG CCT TCT TCT CTG CAG TAC CTG CCT TAC AGA GAT TAT    1711
Lys Leu Pro Glu Pro Ser Ser Leu Gln Tyr Leu Pro Tyr Arg Asp Tyr
            505                     510                     515

AAT TAT TCC CTG GTG ATG GGA GCT TGC TGT GAG AAT GTG ATC GGA TAT    1759
Asn Tyr Ser Leu Val Met Gly Ala Cys Cys Glu Asn Val Ile Gly Tyr
            520                     525                     530
```

Figure 2E

| | | | | | | | | | | | | | | | | |
|---|---|---|---|---|---|---|---|---|---|---|---|---|---|---|---|---|
| ATG | CCC | ATC | CCT | GTC | GGA | GTA | GCA | GGG | CCT | CTG | TGC | CTG | GAT | GGT | AAA | 1807 |
| Met | Pro | Ile | Pro | Val | Gly | Val | Ala | Gly | Pro | Leu | Cys | Leu | Asp | Gly | Lys | |
| | | 535 | | | | | 540 | | | | | 545 | | | | |
| GAG | TAC | CAG | GTT | CCA | ATG | GCA | ACA | ACG | GAA | GGC | TGT | CTG | GTG | GCC | AGC | 1855 |
| Glu | Tyr | Gln | Val | Pro | Met | Ala | Thr | Thr | Glu | Gly | Cys | Leu | Val | Ala | Ser | |
| | 550 | | | | | 555 | | | | | 560 | | | | | |
| ACC | AAC | AGA | GGC | TGC | AGG | GCA | ATA | GGT | CTT | GGT | GGA | GGT | GCC | AGC | AGC | 1903 |
| Thr | Asn | Arg | Gly | Cys | Arg | Ala | Ile | Gly | Leu | Gly | Gly | Gly | Ala | Ser | Ser | |
| 565 | | | | | 570 | | | | | 575 | | | | | 580 | |
| CGG | GTC | CTT | GCA | GAT | GGG | ATG | ACC | CGG | GGC | CCA | GTG | GTG | CGT | CTT | CCT | 1951 |
| Arg | Val | Leu | Ala | Asp | Gly | Met | Thr | Arg | Gly | Pro | Val | Val | Arg | Leu | Pro | |
| | | | | 585 | | | | | 590 | | | | | 595 | | |
| CGT | GCT | TGT | GAT | TCT | GCA | GAA | GTG | AAG | GCC | TGG | CTT | GAA | ACA | CCC | GAA | 1999 |
| Arg | Ala | Cys | Asp | Ser | Ala | Glu | Val | Lys | Ala | Trp | Leu | Glu | Thr | Pro | Glu | |
| | | 600 | | | | | 605 | | | | | 610 | | | | |
| GGG | TTT | GCG | GTG | ATA | AAG | GAC | GCC | TTC | GAT | AGC | ACT | AGC | AGA | TTT | GCA | 2047 |
| Gly | Phe | Ala | Val | Ile | Lys | Asp | Ala | Phe | Asp | Ser | Thr | Ser | Arg | Phe | Ala | |
| | 615 | | | | | 620 | | | | | 625 | | | | | |
| CGT | CTA | CAG | AAG | CTT | CAT | GTG | ACC | ATG | GCA | GGG | CGC | AAC | CTG | TAC | ATC | 2095 |
| Arg | Leu | Gln | Lys | Leu | His | Val | Thr | Met | Ala | Gly | Arg | Asn | Leu | Tyr | Ile | |
| 630 | | | | | 635 | | | | | 640 | | | | | | |

Figure 2F

```
CGT TTC CAG TCC AAG ACA GGG GAT GCC ATG GGG ATG AAC ATG ATT TCC         2143
Arg Phe Gln Ser Lys Thr Gly Asp Ala Met Gly Met Asn Met Ile Ser
645                 650                 655                 660

AAG GGC ACT GAG AAA GCA CTT CTG AAG CTT CAG GAG TTC TTT CCT GAA         2191
Lys Gly Thr Glu Lys Ala Leu Leu Lys Leu Gln Glu Phe Phe Pro Glu
            665                 670                 675

ATG CAG ATT CTG GCA GTT AGT GGT AAC TAC TGC ACT GAC AAG AAA CCT         2239
Met Gln Ile Leu Ala Val Ser Gly Asn Tyr Cys Thr Asp Lys Lys Pro
        680                 685                 690

GCC GCC ATA AAC TGG ATC GAG GGA AGA GGA AAG ACA GTT GTG TGT GAA         2287
Ala Ala Ile Asn Trp Ile Glu Gly Arg Gly Lys Thr Val Val Cys Glu
    695                 700                 705

GCT GTT ATT CCA GCC AAG GTG GTG AGA GAA GTA TTA AAG ACA ACT ACG         2335
Ala Val Ile Pro Ala Lys Val Val Arg Glu Val Leu Lys Thr Thr Thr
710                 715                 720

GAA GCT ATG ATT GAC GTA AAC ATT AAC AAG AAT CTT GTG GGT TCT GCC         2383
Glu Ala Met Ile Asp Val Asn Ile Asn Lys Asn Leu Val Gly Ser Ala
725                 730                 735                 740

ATG GCT GGG AGC ATA GGA GGC TAC AAT GCC CAT GCA AAC ATC GTC             2431
Met Ala Gly Ser Ile Gly Gly Tyr Asn Ala His Ala Asn Ile Val
            745                 750                 755
```

Figure 2G

```
ACT GCT ATC TAC ATT GCA TGT GGC CAG GAT GCA GCA CAG AAT GTG GGG    2479
Thr Ala Ile Tyr Ile Ala Cys Gly Gln Asp Ala Ala Gln Asn Val Gly
        760                     765                     770

AGT TCA AAC TGT ATT ACT TTA ATG GAA GCA AGT GGT CCC ACG AAT GAA    2527
Ser Ser Asn Cys Ile Thr Leu Met Glu Ala Ser Gly Pro Thr Asn Glu
        775                     780                     785

GAC TTG TAT ATC AGC TGC ACC ATG CCA TCT ATA GAG ATA GGA ACT GTG    2575
Asp Leu Tyr Ile Ser Cys Thr Met Pro Ser Ile Glu Ile Gly Thr Val
        790                     795                     800

GGT GGT GGG ACC AAC CTC CTA CCA CAG CAG GCC TGT CTG CAG ATG CTA    2623
Gly Gly Gly Thr Asn Leu Leu Pro Gln Gln Ala Cys Leu Gln Met Leu
805                     810                     815                 820

GGT GTT CAA GGA GCG TGC AAA GAC AAT CCT GGA GAA AAT GCA CGG CAA    2671
Gly Val Gln Gly Ala Cys Lys Asp Asn Pro Gly Glu Asn Ala Arg Gln
        825                     830                     835

CTT GCC CGA ATT GTG TGT GGT ACT GTA ATG GCT GGG GAG TTG TCC TTG    2719
Leu Ala Arg Ile Val Cys Gly Thr Val Met Ala Gly Glu Leu Ser Leu
        840                     845                     850

ATG GCA TTG GCA GCA GGA CAT CTT GTT AGA AGT CAC ATG GTT CAT        2767
Met Ala Leu Ala Ala Gly His Leu Val Arg Ser His Met Val His
        855                     860                     865
```

Figure 2H

```
AAC AGA TCG AAG ATA AAT TTA CAA GAT CTG CAA GGA ACG TGC ACC AAG        2815
Asn Arg Ser Lys Ile Asn Leu Gln Asp Leu Gln Gly Thr Cys Thr Lys
    870                         875                         880

AAG TCA GCT TGAGCAGCCT GACAGTATTG AACTGAAACA CGGGCATTGG                2864
Lys Ser Ala
885

GTTCTCAAGG ACTAACATGA AATCTGTGAA TTAAAAATCT CAATGCAGTG TCTTGTGGAA      2924

GATGAATGAA CGTGATCAGT GAGACGCCCTG CTTGGTTTCT GGCTCTTTCA GAGACGTCTG     2984

AGGTCCCTTG CTCGGAGACT CCTCAGATCT GGAAACAGTG TGGTCCTTCC CATGCTGTAT     3044

TCTGAAAAGA TCTCATATGG ATGTTGTGCT CTGAGCACCA CAGATGTGAT CTGCAGCTCG     3104

TTTCTGAAAT GATGGAGTTC ATGGTGATCA GTGTGAGACT GGCCTCTCCC AGCAGGTTAA     3164

AAATGGAGTT TTAAATTATA CTGTAGCTGA CAGTACTTCT GATTTATAT TTATTTAGTC      3224

TGAGTGTGTAG AACTTTGCAA TCTAAGTTTA TTTTTTGTAA CCTAATAATT CATTTGGTGC    3284

TGGTCTATTG ATTTTTGGGG GTAAACAATA TTATTCTTCA GAAGGGGACC TACTTCTTCA     3344

TGGGAAGAAT TACTTTTATT CTCAAACTAC AGAACAATGT GCTAAGCAGT GCTAAATTGT     3404

TCTCATGAAG AAAACAGTCA CTGCATTTAT CTCTGTAGGC CTTTTTTCAG.AGAGGCCTTG    3464
```

Figure 2I

```
TCTAGATTTT TGCCAGCTAG GCTACTGCAT GTCTTAGTGT CAGGCCTTAG GAAAGTGCCA    3524
CGCTCTGCAC TAAAGATATC AGAGCTCTTG GTGTTACTTA GACAAGAGTA TGAGCAAGTC    3584
GGACCTCTCA GAGTGTGGGA ACACAGTTTT GAAAGAAAAA CCATTTCTCT AAGCCAATTT    3644
TCTTTAAAGA CATTTTAACT TATTTAGCTG AGTTCTAGAT TTTTCGGGTA AACTATCAAA    3704
TCTGTATATG TTGTAATAAA GTGTCTTATG CTAGGAGTTT ATTCAAAGTG TTTAAGTAAT    3764
AAAAGGACTC AAATTTACAC TGATAAAATA CTCTAGCTTG GGCCAGAGAA GACAGTGCTC    3824
ATTAGCGTTG TCCAGGAAAC CCTGCTTGCT TGCCAAGCCT AATGAAGGGA AAGTCAGCTT    3884
TCAGAGCCAA TGATGGAGGC CACATGAATG GCCCTGGAGC CTCCTTTGAT GTTCTGTGGC    3944
CAGGAGCTTG GTGACTGAAT CATTTACGGG CTCCTTTGAT TTTTTTAATG TACCAGTTAG    4004
CTTCCCTCAGG GGGTCAGCAG AGTTGTTGAA TCTTAATTTT TGTATTCTAT CTAATGCTTC GAGTTCAGTC    4064
GTATAAATAA TAATAAAGAG CTCCTTATTT TGTATTCTAT CTAATGCTTC GAGTTCAGTC    4124
TTGGGAAGCT GACATCTCAT GTAGAAGATG GACTCTGAAA GACATTCCAA GAGTGCAGCG    4184
GCATCATGGG AGCCTCTTAG TGATTGTGTG TCAGTATTAT TGTGGAAGAT TGACTTTGCT    4244
TTTGTATGTG AAGTTTCAGA TTGCTCCCTCT TGTGACTTTT TAGCCAGTAA CATTTTATTT    4304
```

Figure 2J

```
ACCTGAGCTT GTCATGGAAG TGGCAGTGAA AAGTATTGAG TATTCATGCT GGTGACTGTA  4364
ACCAATGTCA TCTTGCTAAA AACTCATGTT TTGTACAATT ACTAAATTGT ATACATTTG   4424
TTATAGAATA CTTTTTCCAG TTGAGTAAAT TATGAAAGGA AGTTAACATT AACAGGTGTA  4484
AGCGGTGGCT TTTTAAAAAT GAAGGATTAA CCCTAAGCCC GAGACCCAGA AGCTAGCAAA  4544
GTCTGGCAGA GTGGTAAACT. GTCCTGCTGG GGCCATCCAA TCATCTCTCT. CCATTACACT 4604
TTCTAACTTT GCAGCATTGG TGCTGGCCAG TGTATTGTTT CATTGATCTT CCTTACGCTT  4664
AGAGGGTTTG ATTGGTTCAG ATCTATAATC TCAGCCACAT TGTCTTGGTA TCAGCTGGAG  4724
AGAGTTAAGA GGAAGGGAAA ATAAAGTTCA GATAGCCAAA ACAC                   4768
```

Figure 2K

```
TTTATTAACT TATTTTTTC TTCTTCTAC CCAATTCTAG TCAGGAAAAG ACTAAGGGCT        60

GGAACATAGT GTATCATTGT CTAATTGTTG ATACAAAGTA GATAAATACA TAAAACAAGC      120

ATG CCG CCG CTA TTC AAG GGA CTG AAA CAG ATG GCA AAG CCA ATT GCC       168
Met Pro Pro Leu Phe Lys Gly Leu Lys Gln Met Ala Lys Pro Ile Ala
  1               5                  10                  15

TAT GTT TCA AGA TTT TCG GCG AAA CGA CCA ATT CAT ATA ATA CTT TTT       216
Tyr Val Ser Arg Phe Ser Ala Lys Arg Pro Ile His Ile Ile Leu Phe
             20                  25                  30

TCT CTA ATC ATA TCC GCA TTC GCT TAT CTA TCC GTC ATT CAG TAT TAC       264
Ser Leu Ile Ile Ser Ala Phe Ala Tyr Leu Ser Val Ile Gln Tyr Tyr
         35                  40                  45

TTC AAT GGT TGG CAA CTA GAT TCA AAT AGT GTT TTT GAA ACT GCT CCA       312
Phe Asn Gly Trp Gln Leu Asp Ser Asn Ser Val Phe Glu Thr Ala Pro
     50                  55                  60

AAT AAA GAC TCC AAC ACT CTA TTT CAA GAA TGT TCC CAT TAC TAC AGA       360
Asn Lys Asp Ser Asn Thr Leu Phe Gln Glu Cys Ser His Tyr Tyr Arg
 65                  70                  75                  80

GAT TCC TCT CTA GAT GGT TGG GTA TCA ATC ACC GCG CAT GAA GCT AGT       408
Asp Ser Ser Leu Asp Gly Trp Val Ser Ile Thr Ala His Glu Ala Ser
             85                  90                  95
```

Figure 3A

| | | | | | | |
|---|---|---|---|---|---|---|
| GAG | TTA | CCA | GCC | CCA | CAC | CAT | TAC | TAT | CTA | TTA | AAC | CTG | AAC | TTC | AAT | 456 |
| Glu | Leu | Pro | Ala | Pro | His | His | Tyr | Tyr | Leu | Leu | Asn | Leu | Asn | Phe | Asn | |
|  |  | 100 |  |  |  |  | 105 |  |  |  |  | 110 |  |  |  | |

```
GAG TTA CCA GCC CCA CAC CAT TAC TAT CTA TTA AAC CTG AAC TTC AAT     456
Glu Leu Pro Ala Pro His His Tyr Tyr Leu Leu Asn Leu Asn Phe Asn
        100                 105                 110

AGT CCT AAT GAA ACT GAC TCC ATT CCA GAA CTA GCT AAC ACG GTT TTT     504
Ser Pro Asn Glu Thr Asp Ser Ile Pro Glu Leu Ala Asn Thr Val Phe
        115                 120                 125

GAG AAA GAT AAT ACA AAA TAT CTG CAA GAA GAT CTC AGT GTT TCC         552
Glu Lys Asp Asn Thr Lys Tyr Ile Leu Gln Glu Asp Leu Ser Val Ser
        130                 135                 140

AAA GAA ATT TCT TCT ACT GAT GGA ACG AAA TGG AGG TTA AGA AGT GAC     600
Lys Glu Ile Ser Ser Thr Asp Gly Thr Lys Trp Arg Leu Arg Ser Asp
145                 150                 155                 160

AGA AAA AGT CTT TTC GAC GTA AAG ACG TTA GCA TAT TCT CTC TAC GAT     648
Arg Lys Ser Leu Phe Asp Val Lys Thr Leu Ala Tyr Ser Leu Tyr Asp
        165                 170                 175

GTA TTT TCA GAA AAT GTA ACC CAA GCA GAC CCG TTT GAC GTC CTT ATT     696
Val Phe Ser Glu Asn Val Thr Gln Ala Asp Pro Phe Asp Val Leu Ile
        180                 185                 190

ATG GTT ACT GCC TAC CTA ATG ATG TTC TAC ACC ATA TTC GGC CTC TTC     744
Met Val Thr Ala Tyr Leu Met Met Phe Tyr Thr Ile Phe Gly Leu Phe
        195                 200                 205
```

Figure 3B

```
AAT GAC ATG AGG AAG ACC GGG TCA AAT TTT TGG TTG AGC GCC TCT ACA    792
Asn Asp Met Arg Lys Thr Gly Ser Asn Phe Trp Leu Ser Ala Ser Thr
210                 215                 220

GTG GTC AAT TCT GCA TCA CTT TTC TTA GCA TTG TAT GTC ACC CAA        840
Val Val Asn Ser Ala Ser Leu Phe Leu Ala Leu Tyr Val Thr Gln
        225                 230                 235             240

TGT ATT CTA GGC AAA GAA GTT TCC GCA TTA ACT CTT TTT GAA GGT TTG    888
Cys Ile Leu Gly Lys Glu Val Ser Ala Leu Thr Leu Phe Glu Gly Leu
245                 250                 255

CCT TTC ATT GTA GTT GTT GGT TTC AAG CAC AAA ATC AAG ATT GCC        936
Pro Phe Ile Val Val Val Gly Phe Lys His Lys Ile Lys Ile Ala
        260                 265                 270

CAG TAT GCC CTG GAG AAA TTT GAA AGA GTC GGT TTA TCT AAA AGG ATT    984
Gln Tyr Ala Leu Glu Lys Phe Glu Arg Val Gly Leu Ser Lys Arg Ile
275                 280                 285

ACT GAT GAA ATC GTT TTT GAA TCC GTG AGC GAA GGT GGT CGT            1032
Thr Asp Glu Ile Val Phe Glu Ser Val Ser Glu Glu Gly Gly Arg
        290                 295                 300

TTG ATT CAA GAC CAT TTG CTT TGT ATT TTT GCC TTT ATC GGA TGC TCT    1080
Leu Ile Gln Asp His Leu Leu Cys Ile Phe Ala Phe Ile Gly Cys Ser
305                 310                 315                 320
```

Figure 3C

| | | | | | | | | | | | | | | | |
|---|---|---|---|---|---|---|---|---|---|---|---|---|---|---|---|
| ATG | TAT | GCT | CAC | CAA | TTG | AAG | ACT | TTG | ACA | AAC | TTC | TGC | ATA | TTA | TCA |
| Met | Tyr | Ala | His | Gln | Leu | Lys | Thr | Leu | Thr | Asn | Phe | Cys | Ile | Leu | Ser |
| | | | 325 | | | | | 330 | | | | | | 335 | |

1128

| | | | | | | | | | | | | | | | |
|---|---|---|---|---|---|---|---|---|---|---|---|---|---|---|---|
| GCA | TTT | ATC | CTA | ATT | TTT | GAA | TTG | ATT | ATT | ACT | CCT | ACA | TTT | TAT | TCT |
| Ala | Phe | Ile | Leu | Ile | Phe | Glu | Leu | Ile | Ile | Thr | Pro | Thr | Phe | Tyr | Ser |
| | | 340 | | | | | | 345 | | | | | | 350 | |

1176

| | | | | | | | | | | | | | | | |
|---|---|---|---|---|---|---|---|---|---|---|---|---|---|---|---|
| GCT | ATC | TTA | GCG | CTT | AGA | CTG | GAA | ATG | AAT | GTT | ATC | CAC | AGA | TCT | ACT |
| Ala | Ile | Leu | Ala | Leu | Arg | Leu | Glu | Met | Asn | Val | Ile | His | Arg | Ser | Thr |
| | 355 | | | | | | 360 | | | | | 365 | | | |

1224

| | | | | | | | | | | | | | | | |
|---|---|---|---|---|---|---|---|---|---|---|---|---|---|---|---|
| ATT | ATC | AAG | CAA | ACA | TTA | GAA | GAC | GGT | GTT | CCA | TCT | ACA | GCA |
| Ile | Ile | Lys | Gln | Thr | Leu | Glu | Asp | Gly | Val | Pro | Ser | Thr | Ala |
| 370 | | | | | 375 | | | | | 380 | | | |

1272

| | | | | | | | | | | | | | | | |
|---|---|---|---|---|---|---|---|---|---|---|---|---|---|---|---|
| AGA | ATC | ATT | TCT | AAA | GCA | GAA | AAG | AAA | TCC | GTA | TCT | TCT | TTC | TTA | AAT |
| Arg | Ile | Ile | Ser | Lys | Ala | Glu | Lys | Lys | Ser | Val | Ser | Ser | Phe | Leu | Asn |
| 385 | | | | | 390 | | | | | 395 | | | | | 400 |

1320

| | | | | | | | | | | | | | | | |
|---|---|---|---|---|---|---|---|---|---|---|---|---|---|---|---|
| CTC | AGT | GTG | GTT | GTC | ATT | ATC | ATG | AAA | CTC | TCT | GTC | ATA | CTG | TTG | TTT |
| Leu | Ser | Val | Val | Val | Ile | Ile | Met | Lys | Leu | Ser | Val | Ile | Leu | Leu | Phe |
| | | | 405 | | | | | 410 | | | | | | 415 | |

1368

| | | | | | | | | | | | | | | | |
|---|---|---|---|---|---|---|---|---|---|---|---|---|---|---|---|
| GTT | TTC | ATC | AAC | TTT | TAT | AAC | TTT | GGT | GCA | AAT | TGG | GTC | AAT | GAT | GCC |
| Val | Phe | Ile | Asn | Phe | Tyr | Asn | Phe | Gly | Ala | Asn | Trp | Val | Asn | Asp | Ala |
| | | | 420 | | | | | 425 | | | | | | 430 | |

| | | | | | | | | | | | | | | | | |
|---|---|---|---|---|---|---|---|---|---|---|---|---|---|---|---|---|
| TTC | AAT | TCA | TTG | TAC | TTC | GAT | AAG | GAA | CGT | GTT | TCT | CTA | CCA | GAT | TTT | 1464 |
| Phe | Asn | Ser | Leu | Tyr | Phe | Asp | Lys | Glu | Arg | Val | Ser | Leu | Pro | Asp | Phe | |
| | | 435 | | | | | 440 | | | | | 445 | | | | |
| ATT | ACC | TCG | AAT | GCC | TCT | GAA | AAC | TTT | AAA | GAG | CAA | GCT | ATT | GTT | AGT | 1512 |
| Ile | Thr | Ser | Asn | Ala | Ser | Glu | Asn | Phe | Lys | Glu | Gln | Ala | Ile | Val | Ser | |
| | 450 | | | | | 455 | | | | 460 | | | | | | |
| GTC | ACC | CCA | TTA | TAT | TAC | AAA | CCC | ATT | AAG | TCC | TAC | CAA | CGC | ATT | 1560 | |
| Val | Thr | Pro | Leu | Tyr | Tyr | Lys | Pro | Ile | Lys | Ser | Tyr | Gln | Arg | Ile | | |
| 465 | | | | | 470 | | | | 475 | | | | | 480 | | |
| GAG | GAT | ATG | GTT | CTT | CTA | TTG | CTT | CGT | AAT | GTC | AGT | GTT | GCC | ATT | CGT | 1608 |
| Glu | Asp | Met | Val | Leu | Leu | Leu | Leu | Arg | Asn | Val | Ser | Val | Ala | Ile | Arg | |
| | | 485 | | | | | 490 | | | | | 495 | | | | |
| GAT | AGG | TTC | GTC | AGT | AAA | TTA | GTT | CTT | TCC | GCC | TTA | GTA | TGC | AGT | GCT | 1656 |
| Asp | Arg | Phe | Val | Ser | Lys | Leu | Val | Leu | Ser | Ala | Leu | Val | Cys | Ser | Ala | |
| | 500 | | | | | 505 | | | | 510 | | | | | | |
| GTC | ATC | AAT | GTG | TAT | TTA | TTG | AAT | GCT | AGA | ATT | CAT | ACC | AGT | TAT | | |
| Val | Ile | Asn | Val | Tyr | Leu | Leu | Asn | Ala | Arg | Ile | His | Thr | Ser | Tyr | | 1704 |
| 515 | | | | | 520 | | | | 525 | | | | | | | |
| ACT | GCA | GAC | CAA | TTG | GTG | AAA | ACT | GAA | GTC | ACC | AAG | TCT | TTT | ACT | | 1752 |
| Thr | Ala | Asp | Gln | Leu | Val | Lys | Thr | Glu | Val | Thr | Lys | Ser | Phe | Thr | | |
| 530 | | | | | 535 | | | | 540 | | | | | | | |

Figure 3E

```
GCT CCT GTA CAA AAG GCT TCT ACA CCA GTT TTA ACC AAT AAA ACA GTC   1800
Ala Pro Val Gln Lys Ala Ser Thr Pro Val Leu Thr Asn Lys Thr Val
545                 550                 555                 560

ATT TCT GGA TCG AAA GTC AAA AGT TTA TCA TCT GCG CAA TCG AGC TCA   1848
Ile Ser Gly Ser Lys Val Lys Ser Leu Ser Ser Ala Gln Ser Ser Ser
            565                 570                 575

TCA GGA CCT TCA TCT AGT GAG GAA GAT GAT TCC CGC GAT ATT GAA       1896
Ser Gly Pro Ser Ser Ser Glu Glu Asp Asp Ser Arg Asp Ile Glu
580                 585                 590

AGC TTG GAT AAG AAA ATA CGT CCT TTA GAA GAA TTA GAA GCA TTA TTA   1944
Ser Leu Asp Lys Lys Ile Arg Pro Leu Glu Glu Leu Glu Ala Leu Leu
    595                 600                 605

AGT AGT GGA AAT ACA AAA CAA TTG AAG AAC AAA GAG GTC GCT GCC TTG   1992
Ser Ser Gly Asn Thr Lys Gln Leu Lys Asn Lys Glu Val Ala Ala Leu
610                 615                 620

GTT ATT CAC GGT AAG TTA CCT TTG TAC GCT TTG GAG AAA AAA TTA GGT   2040
Val Ile His Gly Lys Leu Pro Leu Tyr Ala Leu Glu Lys Lys Leu Gly
625                 630                 635                 640

GAT ACT ACG AGA GCG GTT GCG GTA CGT AGG AAG GCT CTT TCA ATT TTG   2088
Asp Thr Thr Arg Ala Val Ala Val Arg Arg Lys Ala Leu Ser Ile Leu
            645                 650                 655
```

Figure 3F

```
GCA GAA GCT CCT GTA TTA GCA TCT GAT CGT TTA CCA TAT AAA AAT TAT    2136
Ala Glu Ala Pro Val Leu Ala Ser Asp Arg Leu Pro Tyr Lys Asn Tyr
            660                 665                 670

GAC TAC GAC CGC GTA TTT GGC GCT TGT GAA AAT GTT ATA GGT TAC        2184
Asp Tyr Asp Arg Val Phe Gly Ala Cys Glu Asn Val Ile Gly Tyr
        675                 680                 685

ATG CCT TTG CCC GTT GGT GTT ATA GGC CCC TTG GTT ATC GAT GGT ACA    2232
Met Pro Leu Pro Val Gly Val Ile Gly Pro Leu Val Ile Asp Gly Thr
            690                 695                 700

TCT TAT CAT ATA CCA ATG GCA ACT ACA GAG GGT TGT TTG GTA GCT TCT    2280
Ser Tyr His Ile Pro Met Ala Thr Thr Glu Gly Cys Leu Val Ala Ser
    705                 710                 715                 720

GCC ATG CGT GGC TGT AAG GCA ATC AAT GCT GGC GGT GGT GCA ACA ACT    2328
Ala Met Arg Gly Cys Lys Ala Ile Asn Ala Gly Gly Gly Ala Thr Thr
            725                 730                 735

GTT TTA ACT AAG GAT GGT ATG ACA AGA GGC CCA GTA GTC CGT TTC CCA    2376
Val Leu Thr Lys Asp Gly Met Thr Arg Gly Pro Val Val Arg Phe Pro
            740                 745                 750

ACT TTG AAA AGA TCT GGT GCC TGT AAG ATA TGG TTA GAC TCA GAA GAG    2424
Thr Leu Lys Arg Ser Gly Ala Cys Lys Ile Trp Leu Asp Ser Glu Glu
            755                 760                 765
```

Figure 3G

```
GGA CAA AAC GCA ATT AAA AAA GCT TTT AAC TCT ACA TCA AGA TTT GCA    2472
Gly Gln Asn Ala Ile Lys Lys Ala Phe Asn Ser Thr Ser Arg Phe Ala
770                 775                 780

CGT CTG CAA CAT ATT CAA ACT TGT CTA GCA GGA GAT TTA CTC TTC ATG    2520
Arg Leu Gln His Ile Gln Thr Cys Leu Ala Gly Asp Leu Leu Phe Met
785                 790                 795                 800

AGA TTT AGA ACA ACT GGT GAC GCA ATG GGT ATG AAT ATG ATT TCT        2568
Arg Phe Arg Thr Thr Gly Asp Ala Met Gly Met Asn Met Ile Ser
        805                 810                 815

AAA GGT GTC GAA TAC TCA TTA AAG CAA ATG GTA GAA GAG TAT TGT GGC TGG 2616
Lys Gly Val Glu Tyr Ser Leu Lys Gln Met Val Glu Glu Tyr Cys Gly Trp
    820                 825                 830

GAA GAT ATG GAG GTT GTC TCC GTT TCT GGT AAC TAC TGT ACC GAC AAA    2664
Glu Asp Met Glu Val Val Ser Val Ser Gly Asn Tyr Cys Thr Asp Lys
835                 840                 845

AAA CCA GCT GCC ATC AAC TGG ATC GAA GGT CGT GGT AAG AGT GTC GTC    2712
Lys Pro Ala Ala Ile Asn Trp Ile Glu Gly Arg Gly Lys Ser Val Val
    850                 855                 860

GCA GAA GCT ACT ATT CCT GGT GAT GTT GTC AGA AAA GTG TTA AAA AGT    2760
Ala Glu Ala Thr Ile Pro Gly Asp Val Val Arg Lys Val Leu Lys Ser
865                 870                 875                 880
```

Figure 3H

```
GAT GTT TCC GCA TTG GTT GAG TTG AAC ATT GCT AAG AAT TTG GTT GGA    2808
Asp Val Ser Ala Leu Val Glu Leu Asn Ile Ala Lys Asn Leu Val Gly
            885                     890                     895

TCT GCA ATG GCT GGG TCT GTT GGT GGA TTT AAC GCA CAT GCA GCT AAT    2856
Ser Ala Met Ala Gly Ser Val Gly Gly Phe Asn Ala His Ala Ala Asn
            900                     905                     910

TTA GTG ACA GCT GTT TTC TTG GCA TTA GGA CAA GAT CCT GCA CAA AAT    2904
Leu Val Thr Ala Val Phe Leu Ala Leu Gly Gln Asp Pro Ala Gln Asn
            915                     920                     925

GTT GAA AGT TCC AAC TGT ATA ACA TTG ATG AAA GAA GTG GAC GGT GAT    2952
Val Glu Ser Ser Asn Cys Ile Thr Leu Met Lys Glu Val Asp Gly Asp
            930                     935                     940

TTG AGA ATT TCC GTA TCC ATG CCA TCC ATC GAA GTA GGT ACC ATC GGT    3000
Leu Arg Ile Ser Val Ser Met Pro Ser Ile Glu Val Gly Thr Ile Gly
            945                     950                     955                     960

GGT ACT GTT CTA GAA CCA CAA GGT GCC ATG TTG GAC TTA TTA GGT        3048
Gly Thr Val Leu Glu Pro Gln Gly Ala Met Leu Asp Leu Leu Gly
        965                     970                     975

GTA AGA GGC CCG CAT GCT ACC GCT CCT GGT ACC AAC GCA CGT CAA TTA    3096
Val Arg Gly Pro His Ala Thr Ala Pro Gly Thr Asn Ala Arg Gln Leu
            980                     985                     990
```

Figure 3I

```
GCA AGA ATA GTT GCC TGT GCC GTC TTG GCA GGT GAA TTA TCC TTA TGT    3144
Ala Arg Ile Val Ala Cys Ala Val Leu Ala Gly Glu Leu Ser Leu Cys
         995                1000                    1005

GCT GCC CTA GCA GCC GGC CAT TTG GTT CAA AGT CAT ATG ACC CAC AAC    3192
Ala Ala Leu Ala Ala Gly His Leu Val Gln Ser His Met Thr His Asn
        1010                1015                    1020

AGG AAA CCT GCT GAA CCA ACA AAA CCT AAC AAT TTG GAC GCC ACT GAT    3240
Arg Lys Pro Ala Glu Pro Thr Lys Pro Asn Asn Leu Asp Ala Thr Asp
        1025                1030                    1035    1040

ATA AAT CGT TTG AAA GAT GGG TCC GTC ACC TGC ATT AAA TCC            3282
Ile Asn Arg Leu Lys Asp Gly Ser Val Thr Cys Ile Lys Ser
        1045                1050

TAAACTTAGT CATACGTCAT TGGTATTCTC TTGAAAAGA AGCACAACAG CACCATGTGT   3342

TACGTAAAAT ATTTACTT                                                3360
```

Figure 3J

PROCESS AND COMPOSITION FOR INCREASING SQUALENE AND STEROL ACCUMULATION IN HIGHER PLANTS

CROSS-REFERENCE TO RELATED APPLICATION

This is a divisional of application Ser. No. 07/934,374, filed Aug. 14, 1992, now U.S. Pat. No. 5,349,126, which is a continuation-in-part of application Ser. No. 07/596,467, filed Oct. 12, 1990, now U.S. Pat. No. 5,306,862, whose disclosures are incorporated by reference herein.

TECHNICAL FIELD

The present invention relates to processes and compositions for increasing the accumulation of squalene and sterols in higher plants, and more particularly to increasing squalene and non-delta-5 sterol accumulation by increasing the amount of a gene encoding a polypeptide having HMG-CoA reductase activity.

BACKGROUND OF THE INVENTION

Acetate is the metabolic precursor of a vast array of compounds vital for cell and organism viability. Acetyl coenzyme A (CoA) reacts with acetoacetyl CoA to form 3-hydroxy-3-methylglutaryl CoA (HMG-CoA). HMG-CoA is reduced to mevalonate in an irreversible reaction catalyzed by the enzyme HMG-CoA reductase. Mevalonate is phosphorylated and decarboxylated to isopentenyl-pyrophosphate (IPP). Through the sequential steps of isomerization, condensation and dehydrogenation, IPP is converted to geranyl pyrophosphate (GPP). GPP combines with IPP to form farnesyl pyrophosphate (FPP), two molecules of which are reductively condensed to form squalene, a 30-carbon precursor of sterols.

Sterols are derivatives of a fused, reduced ring system, cyclopenta-[α]-phenanthrene, comprising three fused cyclohexane rings (A, B and C) in a phenanthrene arrangement, and a terminal cyclopentane ring (D) having the formula and carbon atom position numbering shown below:

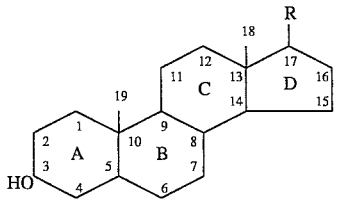

where R is an 8 to 10 carbon-atom side chain.

In plants, squalene is converted to squalene epoxide, which is then cyclized to form cycloartenol (4,4,14α-trimethyl-9β,19 cyclo-5α-cholest-24-en-3β-ol). Cycloartenol has two methyl groups at position 4, a methyl group at position 14, a methylene bridge between the carbon atoms at positions 9 and 19 that forms a disubstituted cyclopropyl group at those positions, and includes an 8 carbon sidechain of the formula: $CH_3CH(CH_2)_2CH=C(CH_3)_2$.

Cycloartenol is formed in an early stage in the biosynthetic pathway of sterol production in higher plants. Cycloartenol is formed from squalene epoxide, which is formed from squalene, a derivative of mevalonic acid (mevalonate). Squalene epoxide can alternatively be converted into pentacyclic sterols, containing five instead of four rings. Exemplary pentacyclic sterols include the phytoalexins and saponins.

Being one of the first sterols in the higher plant biosynthetic pathway, cycloartenol serves as a precursor for the production of numerous other sterols. In normal plants, cycloartenol is converted to predominantly 24-methylene cycloartenol (4,4,14α-trimethyl-9β,19 cyclo-22,23-dihydroergosta-24(28)-en-3-β-ol), cycloeucalenol (4,14α-dimethyl-9β,19 cyclo-5α-ergost-24(28)-en-3α-ol), obtusifoliol (4,14α-dimethyl-5α-ergosta-8,24(28)-dien-3β-ol), isofucosterol (5α-stigmasta-5-Z-24(28)-dien-3β-ol), sitosterol (5α-stigmasta-5-en-3β-ol), stigmasterol (stigmasta-5,E-22-dien-3β-ol), campesterol (5α-ergosta-5-en-3β-ol), and cholesterol (5α-cholesta-5-en-3β-ol).

Although sterols produced by plants, and particularly higher (vascular) plants, can be grouped by the presence or absence of one or more of several functionalities, plant sterols are classified into two general groups herein; i.e., those containing a double bond between the carbon atoms at positions 5 and 6 (delta-5 or Δ5 sterols) and those not containing a double bond between the carbon atoms at positions 5 and 6 (non-delta-5 sterols).

Exemplary naturally occurring delta-5 plant sterols isofucosterol, sitosterol, stigmasterol, campesterol, cholesterol, and dihydrobrassicasterol. Exemplary naturally occurring non-delta-5 plant sterols are cycloartenol, 24-methylene cycloartenol, cycloeucalenol, and obtusifoliol.

The most abundant sterols of vascular plants are campesterol, sitosterol and stigmasterol, all of which contain a double bond between the carbon atoms at positions 5 and 6 and are classified as delta-5 sterols.

The ratio of delta-5 to non-delta-5 sterols in plants can be an important factor relating to insect pest resistance. Insect pests are unable to synthesize de novo the steroid nucleus and depend upon external sources of sterols in their food source for production of necessary steroid compounds. In particular, insect pests require an external source of delta-5 sterols. By way of example, externally provided delta-5 sterols are necessary for the production of ecdysteroids, hormones that control reproduction and development. See, e.g., Costet et al., *Proc. Natl. Acad. Sci. U.S.A.*, 84:643 (1987) and Corio-Costet et al., *Archives of Insect Biochem. Physiol.*, 11:47 (1989).

Treatment of wheat with the fungicide fenpropimorph reduced delta-5 sterol content from about 93 percent of total sterol to about 1 percent of total sterol and increased non-delta-5 sterol content from about 7 percent of total sterol to about 99 percent of total sterol. Where the phytophagous grasshopper *Locusta migratoria* was reared feeding on wheat seedlings treated with fenpropimorph, the concentration of ecdysteroids in eggs was reduced by 80 percent. Those eggs either did not develop (meiosis is inhibited) or they developed with complex abnormalities and malfunctions. Costet et al., *Proc. Natl. Acad. Sci. U.S.A.*, 84:643 (1987); Corio-Costet et al., *Archives of Insect Biochem. Physiol.*, 11:47 (1989).

Because insects can use delta-5 sterols for steroid production, those delta-5 sterols are referred to herein as "utilizable" sterols. Non-delta-5 sterols are referred to herein as "non-utilizable" sterols.

Naturally occurring higher plants typically contain an excess of utilizable over non-utilizable sterols. Costet et al., *Proc. Natl. Acad. Sci. U.S.A.*, 84:643 (1987); Corio-Costet et al., *Archives of Insect Biochem, Physiol.*, 11:47 (1989). Such plants thus can provide an appropriate food supply for insect pests.

Plants having an abundance of non-utilizable sterols have also been produced by treatment with inhibitors of sterol biosynthesis such as the fungicides triarimol, tridemorph, and triparanol. Hosokawa et al., *Lipids*, 19(6):449 (1984). The use of fungicides, however, is undesirable in light of the adverse environmental effects attendant with the use of such chemicals.

All of the fungicides discussed above are known to inhibit sterol biosynthesis subsequent to the formation of cycloartenol.

As set forth above, cycloartenol is a metabolic derivative of mevalonate, which is formed from the reduction of 3-hydroxy-3-methylglutaryl coenzyme A (HMG-CoA). The reduction of HMG-CoA to mevalonate is catalyzed by the enzyme HMG-CoA reductase.

The HMG-CoA reductase enzymes of animals and yeasts are integral membrane glycoproteins of the endoplasmic reticulum. The intact enzyme comprises three regions: a catalytic region, containing the active site of the enzyme; a membrane binding region, anchoring the enzyme to the endoplasmic reticulum; and a linker region, joining the catalytic and membrane binding regions of the enzymes. The membrane binding region occupies the $NH_2$-terminal portion of the intact protein, whereas the catalytic region occupies the COOH-terminal portion of the protein, with the linker region constituting the remaining portion. Basson, M. E. et al., *Mol. Cell Biol.*, 8(9):3797–3808 (1988). At present, the sub-cellular localization of HMG-CoA reductase in plants is not known. Russell, D. W. et al., *Current Topics in Plant Biochemistry*, Vol. 4, ed. by D. D. Randall et al., Univ. of Missouri (1985).

The activity of HMG-CoA reductase in animals and yeasts is known to be subject to feedback inhibition by sterols. Such feedback inhibition requires the presence of the membrane binding region of the enzyme. See, e.g., Gil, G. et al., *Cell*, 41: 249–258(1985); Bard, M. and Downing, J. F. *Journal of General Microbiology*, 125:415–420(1981).

Given that mevalonate is the precursor for sterols and other isoprenoids, it might be expected that increases in the amount or activity of HMG-CoA reductase would lead to increases in the accumulation of both sterols and other isoprenoids. In yeasts and non-photosynthetic microorganisms, increases in HMG-CoA reductase activity are not associated with predictable increases in the production of sterols or other isoprenoids.

In mutant strains of the yeast *Saccharomyces cerevisiae* (*S. cerevisiae*) having abnormally high levels of HMG-CoA reductase activity, the production of two sterols, 4,14-dimethylzymosterol and 14-methylfecosterol, is markedly increased above normal. Downing et al., *Biochemical and Biophysical Research Communications*, 94(3): 974–979(1980).

When HMG-CoA reductase activity was increased by illumination in non-photosynthetic microorganisms, isoprenoid (carotenoid), but not sterol (ergosterol), synthesis was enhanced. Tada et al., *Plant and Cell Physiology*, 23(4): 615–621(1982). There are no studies reporting the effects of such increases in HMG-CoA reductase activity in plants.

SUMMARY OF THE INVENTION

The present invention provides a process of increasing sterol accumulation in a transgenic plant comprising:

(a) transforming a plant cell with a recombinant DNA molecule comprising a vector operatively linked to a DNA segment that encodes a polypeptide having HMG-CoA reductase activity and a promoter suitable for driving the expression of said polypeptide in said plant cell to form a transformed plant cell; and (b) regenerating the transformed plant cell into the transgenic plant.

A polypeptide having HMG-CoA reductase activity preferably comprises the catalytic region and at least a portion of the linker region but is free from the membrane binding region of a HMG-CoA reductase. In a preferred embodiment, the promoter is a promoter whose regulatory function is substantially unaffected by the level of sterol in said transgenic plant such as the CaMV 35S promoter. A preferred recombinant DNA molecule is plasmid HMGRΔ227-pKYLX71.

The plant cell is preferably obtained from plants of the group consisting of tobacco, cotton, soybean, tomato and alfalfa. A sterol whose accumulation is increased is preferably a non-delta-5 sterol and, more preferably cycloartenol.

A similar process to that set forth above is used increase squalene accumulation and to increase pest resistance in a transgenic plant.

The present invention further contemplates a transgenic plant produced in accordance with any of the above processes.

Still further, the present invention contemplates a transgenic plant that (a) has an increased amount of a structural gene that encodes a polypeptide having HMG-CoA reductase activity and (b) over accumulates sterols or squalene relative to a native, non-transgenic plant of the same strain.

The encoded polypeptide is preferably an intact HMG-CoA reductase enzyme or an active, truncated HMG-CoA reductase enzyme comprising the catalytic and at least a portion of the linker region that is free from the membrane binding region of a HMG-CoA reductase enzyme such as a hamster HMG-CoA reductase.

Preferably, the transgenic plant is a transgenic tobacco, cotton, soybean, tomato or alfalfa plant. The present invention also contemplates a transgenic tobacco plant whose seeds have ATCC accession No. 40904 and mutants, recombinants, genetically engineered derivatives thereof and hybrids derived therefrom.

In a still further aspect, the present invention contemplates a transgenic plant seed capable of germinating into a transgenic plant that over accumulates sterol or squalene relative to a native, non-transgenic plant of the same strain and mutants, recombinants, genetically engineered derivatives thereof and hybrids derived therefrom.

BRIEF DESCRIPTION OF THE DRAWINGS

In the drawings forming a portion of this disclosure:

FIG. 1 is a schematic representation of the metabolism of acetyl coenzyme A to sterols and other isoprenoids in plants as published by Russell et al., *Current Topics in Pant Biochemistry*, Vol. 4, ed. by D. D. Randall et al., Univ. of Missouri (1985).

FIG. 2, shown as eleven panels designated FIG. 2A through 2K, is the composite nucleotide sequence of the cDNA corresponding to the mRNA for hamster HMG-CoA reductase (SEQ ID NO:1), and the predicted amino acid sequence (SEQ ID NO:2) of the protein as published by Chin et al., *Nature*, 308:613–617 (1984). Nucleotides are numbered (right-hand side) in the 5' to 3' direction. The predicted amino acid sequence is shown below the nucleotide sequence. The amino acid residues are numbered below every fifth amino acid beginning with the initiator methionine.

FIG. 3, shown as ten panels designated FIG. 3A through 3J is the nucleotide base sequence (SEQ ID NO:3) and derived amino acid residue sequence (SEQ ID NO:4) for *S.*

Figures 4, 5:
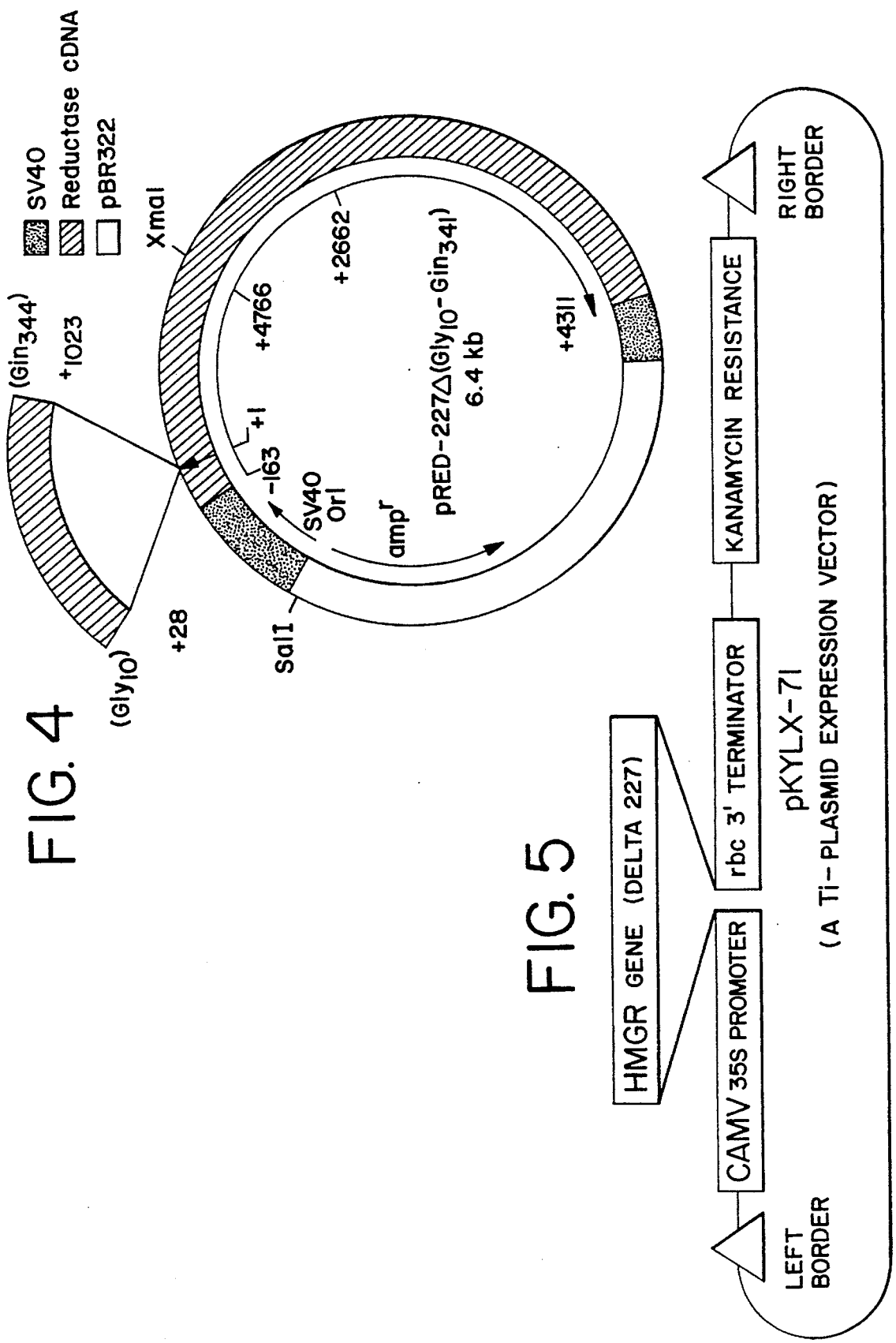

*cerevisiae* HMG-CoA reductase 1 published by Basson, M. E. et al., *Mol. Cell Biol.*, 8(9):3797–3808 (1988). Nucleotides are shown and numbered as discussed for FIG. 2 as are the derived amino acid residues.

FIG. 4 is a schematic drawing showing the structure of a plasmid (pRed-227Δ) used to insert a truncated hamster gene encoding for hamster HMG-CoA reductase into cells lacking such hamster enzyme. Base pairs of the reductase coding sequence (nucleotides 28 to 1023) that encode amino acids 10 to 341 have been deleted and are shown externally of the plasmid. The hatched area denotes the reductase cDNA sequence portion of the plasmid. The reductase cDNA initiator methionine codon (nucleotide 1) and terminator codon (nucleotide 2662) are indicated, as are other features of the plasmid.

FIG. 5 is a schematic restriction map of plasmid HMGRΔ227-pKYLX71 used to transform the plants of the present invention.

DETAILED DESCRIPTION OF THE INVENTION

I. Definitions

The following words and phrases have the meanings set forth below.

Expression: The combination of intracellular processes, including transcription and translation undergone by a structural gene to produce a polypeptide.

Plant integrating vector: A polynucleotide having a first portion containing a structural gene and control elements that direct and regulate expression of that structural gene when operatively linked to that gene and a second portion containing polynucleotide sequences that permit the first portion to be integrated into the chromosome of a plant cell.

Operatively linked: A structural gene is covalently bonded in correct reading frame to another DNA (or RNA as appropriate) segment, such as to a plant integrating vector so that the structural gene is under the control of the plant integrating vector.

Promoter: A recognition site on a DNA sequence or group of DNA sequences that provide an expression control element for a structural gene and to which RNA polymerase specifically binds and initiates RNA synthesis (transcription) of that gene.

Recombinant DNA molecule: A hybrid DNA sequence comprising at least two nucleotide sequences not normally found together in nature.

Regeneration: The process of growing a plant from a plant cell (e.g. plant protoplast or explant).

Structural gene: A DNA sequence that is expressed as a polypeptide, i.e., an amino acid residue sequence.

Transformation: A process of introducing an exogenous sequence (e.g. a vector, a recombinant DNA molecule) into a cell or protoplasts in which that exogenous DNA is incorporated into a chromosome.

Transformed plant cell: A plant cell whose DNA has been altered by the introduction of an exogenous DNA molecule into that cell or protoplast.

Transgenic plant cell: Any plant cell derived or regenerated from a transformed plant cell or protoplast or derived from a transgenic plant. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

II. The Invention

A. Processes for Increasing Sterol Accumulation

In one aspect, the present invention relates to a process for increasing sterol accumulation in transgenic plants, as well as to the transgenic plants that exhibit increased sterol accumulation relative to a native variety of the plant. Preferably, the increase in sterol accumulation is the result of an increased accumulation of non-delta-5 sterols (i.e., sterols lacking a double bond between the carbon atoms at positions 5 and 6 of the sterol nucleus).

A plant contemplated by this invention is a vascular, multicellular higher plant. Such higher plants will hereinafter be usually referred to simply as "plants". Such "plants" include both complete entities having leaves, stems, seeds, roots and the like as well as callus and cell cultures that are monocotyledonous and dicotyledonous. Dicotyledonous plants are a preferred embodiment of the present invention.

Preferred plants are members of the Solanaceae, Leguminosae, Ammiaceae, Brassicaceae, Gramineae, Carduaceae and Malvaceae families. Exemplary plant members of those families are tobacco, petunia and tomato (Solanaceae), soybean and alfalfa (Leguminosae), carrot (Ammiaceae), corn and barley (Gramineae, arabidopsis (Brassicaceae), guayule (Carduaceae), and cotton (Malvaceae). A preferred plant is tobacco of the strain *Nicotina tabacum* (*N. tabacum*), cotton of the strain Coker line 312-5A, soybean of the strain *Glycine max*, alfalfa of the strain RYSI or tomato of the strain *Lycopersicon esculentum*.

A transgenic plant contemplated by this invention is produced by transforming a plant cell or protoplast with an added, exogenous structural gene that encodes a polypeptide having HMG-CoA reductase activity to produce a transformed plant cell, and regenerating a transgenic plant from the transformed plant cell. The encoded polypeptide is expressed both in the transformed plant cell or protoplast and the resulting transgenic plant. (The phrase "plant cell" will hereinafter be used to include a plant protoplast, except where plant protoplasts are specifically discussed.)

A non-transgenic plant that serves as the source of the plant cell that is transformed; i.e., the precursor cell, is referred to herein as a "native, non-transgenic" plant. The native, non-transgenic plant is of the same strain as the formed transgenic plant.

Sterol production in a transgenic plant of the present invention is increased by increasing the activity of the enzyme HMG-CoA reductase, which enzyme catalyzes the conversion of 3-hydroxy-3-methylglutaryl Coenzyme A (HMG-CoA) to mevalonate. As used herein, "activity" means the total catalytic activity of HMG-CoA reductase in a plant cell. As used herein, the term "specific activity" means the activity normalized to cellular protein content.

HMG-CoA reductase activity is increased by increasing the amount (copy number) of a gene encoding a polypeptide having HMG-CoA reductase catalytic activity. Expression of the increased amount of that encoded structural gene enhances the activity of that enzyme.

The amount of the expressed gene is increased by transforming a plant cell with a recombinant DNA molecule comprising a vector operatively linked to a DNA segment that encodes a polypeptide having HMG-CoA reductase activity, and a promoter suitable for driving the expression of that polypeptide in that plant cell, and culturing the transformed plant cell into a transgenic plant. Such a polypeptide includes intact as well as catalytically active, truncated HMG-CoA reductase proteins.

Thus, a transformed plant cell and a transgenic plant have one or more added, exogenous genes that encode a polypeptide having HMG-CoA reductase activity relative to a native, non-transgenic plant or untransformed plant cell of the same type. As such, a transformed plant cell or transgenic plant can be distinguished from an untransformed plant cell or native, non-transgenic plant by standard technology such as agarose separation of DNA fragments or mRNAs followed by transfer and appropriate blotting with DNA or RNA, e.g., Southern or Northern blotting, or by use of polymerase chain reaction technology, as are well known. Relative HMG-CoA reductase activity of the transformed cell or transgenic plant with untransformed cells and native, non-transgenic plants or cell cultures therefrom can also be compared, with a relative activity for that enzyme of about 1.5:1 for transgenic (transformed):native (untransformed) showing transformation. Higher relative activity ratios such as about 15:1 have also been observed.

Sterol accumulation can also be used to distinguish between native, non-transgenic and transgenic plants. A transgenic plant has at least about twice the total sterol content as a native, non-transgenic plant where a single added gene is present. Greater differences up to about forty-fold have also been observed.

The increased accumulation of sterol is preferably the result of an increase in the accumulation of non-delta-5 sterols lacking a double bond between the carbon atoms at positions 5 and 6.

By way of example, in transgenic tobacco made in accordance with a process of the present invention, the increase in sterol accumulation was found to be due predominantly to an increase in the accumulation of the non-delta-5 sterol cycloartenol (See Example 3 hereinafter). Increases in non-delta-5 sterols were also observed in transgenic cotton, soybean, tomato and alfalfa plant callus cultures (See Examples 6, 7, 8 and 9 hereinafter).

B. Processes for Increasing Squalene Accumulation

In another aspect, the present invention relates to processes for increasing squalene accumulation in transgenic plants, as well as to the transgenic plants that exhibit increased squalene accumulation relative to a native, non-transgenic plant of the same strain.

Squalene production in a transgenic plant of the present invention is increased by increasing the activity of the enzyme HMG-CoA reductase. The increase in HMG-CoA reductase activity is carried out in accordance with the processes discussed above relating to a process for increasing sterol accumulation.

Although similar processes are used to increase sterol and squalene accumulation in transgenic plants, there does not appear to be any causal or necessary relationship between the increased accumulation of those compounds. For example, observed increases in sterol accumulation of transgenic plants of the present invention do not correlate with increases in squalene accumulation in those same plants. Table 1, below, shows the increases in sterol and squalene accumulation in transgenic tobacco, cotton, soybean, tomato and alfalfa callus. The data in Table 1 are taken from the data in Tables 6, 7, 8, 9 and 10 hereinafter. The Delta values shown in Table 1 represent averages of the individual data in Tables 6–10.

TABLE 1

| Plant | Control | Transgenic | Delta[2] (Cont-Trans) |
|---|---|---|---|
| Sterol Accumulation[1] | | | |
| Tobacco | 0.21 | 0.78 | 0.57 |
| Cotton | 0.16 | 0.60 | 0.44 |
| Soybean | 0.37 | 0.85 | 0.48 |
| Tomato | 0.04 | 0.99 | 0.95 |
| Alfalfa | 0.24 | 1.26 | 1.02 |
| Squalene Accumulation[1] | | | |
| Tobacco | <0.010 | 0.126 | 0.126 |
| Cotton | <0.002 | 0.560 | 0.560 |
| Soybean | 0.022 | 0.233 | 0.211 |
| Tomato | <0.002 | 0.090 | 0.090 |
| Alfalfa | 0.002 | 0.052 | 0.050 |

[1]Sterol and squalene levels of Control and Transgenic callus are given as percentage of dry weight
[2]Delta values are calculated as control minus transgenic (Cont-Trans) levels. Where the control value is trace (tr) or <0.01, the delta value is calculated as the level in the transgenic callus.

It can be seen that there is no correlation between increases in sterol and squalene accumulation. In tobacco, the increase in sterol accumulation (0.57) was associated with an increase in squalene accumulation of 0.126. In marked contrast, in alfalfa where the increase in sterol accumulation was twice that seen in tobacco (1.02 vs. 0.57), the accumulation of squalene was only one-twentieth that seen in tobacco (0.05 vs. 0.126). These data show the likely independent effects of transformation and formation of transgenic plants on sterol and squalene accumulation.

Squalene accumulation can also be used to distinguish between transgenic and native, non-transgenic plants. Thus, a transgenic plant contemplated herein can accumulate about 5 to about 75 times the squalene of a native, non-transformed, plant.

C. Structural Genes

The present invention contemplates transforming a plant cell with a structural gene that encodes a polypeptide having HMG-CoA reductase activity. The HMG-CoA reductase enzymes of both animal and yeast cells comprise three distinct amino acid residue sequence regions, which regions are designated the catalytic region, the membrane binding region and the linker region.

The catalytic region contains the active site of the HMG-CoA reductase enzyme and comprises about forty percent of the COOH-terminal portion of intact HMG-CoA reductase enzyme.

The membrane binding region contains hydrophobic amino acid residues and comprises about fifty percent of the $NH_2$-terminal portion of intact HMG-CoA reductase enzyme.

The linker region connects the catalytic and membrane binding regions, and constitutes the remaining about ten percent of the intact enzyme.

As discussed in greater detail below, only the catalytic region of HMG-CoA reductase is needed herein to provide the desired enzyme activity. Thus, an exogenous structural gene that encodes a polypeptide corresponding to that catalytic region is the minimal gene required for transforming plant cells. The present invention therefore contemplates use of both intact and truncated structural genes that encode a polypeptide having HMG-CoA reductase activity.

A structural gene encoding a polypeptide having HMG-CoA reductase activity can be obtained or constructed from a variety of sources and by a variety of methodologies. See, e.g., Carlson et al., *Cell*, 28:145 (1982); Rine et al., *Proc. Nat. Acad. Sci. U.S.A.*, 80:6750 (1983). Exemplary of such structural genes are the mammalian and yeast genes encoding HMG-CoA reductase or the catalytic region thereof.

The mammalian genome contains a single gene encoding HMG-CoA reductase. The nucleotide base sequence of the hamster and human gene for KMG-CoA reductase have been described. A composite nucleotide sequence of cDNA corresponding to the mRNA (SEQ ID NO:1), as well as the derived amino acid residue sequence (SEQ ID NO:2), for hamster HMG-CoA reductase is provided in FIG. 2, reprinted from Chin et al., *Nature*, 308:613 (1984). The composite nucleotide sequence of FIG. 2 (SEQ ID NO:1), comprising about 4768 base pairs, includes the nucleotide sequence encoding the intact hamster HMG-CoA reductase enzyme.

Intact hamster HMG-CoA reductase comprises about 887 amino acid residues (SEQ ID NO:2). A structural gene encoding an intact hamster HMG-CoA reductase enzyme of 887 amino acid residues comprises base pairs from about nucleotide position 164 to about nucleotide position 2824 of FIG. 2 (SEQ ID NO:1).

A preferred structural gene is one that encodes a polypeptide corresponding to only the catalytic region of the enzyme. Two catalytically active segments of hamster HMG-CoA reductase have been 1187–2824 from FIG. 2 (SEQ ID NO:1), which encodes amino acid residues 1–9 (from the membrane binding region) and 342–887 has been used to transform plant cells. The schematic structure of the transforming plasmid (pRED-227Δ) containing the truncated gene is reprinted in FIG. 4. A structural gene encoding a polypeptide comprising a catalytically active, truncated or intact HMG-CoA reductase enzyme from other organisms such as yeast can also be used in accordance with the present invention.

Yeast cells contain two genes encoding HMG-CoA reductase. The two yeast genes, designated HMG1 and HMG2, encode two distinct forms of HMG-CoA reductase, designated HMG-CoA reductase 1 and HMG-CoA reductase 2. The nucleotide base sequence of HMG1 (SEQ ID NO:3) as well as the amino acid residue sequence of HMG-CoA reductase 1 (SEQ ID NO:4) are presented in FIG. 3, taken from Basson et al., *Mol. Cell Biol.*, 8(9):3797 (1988). The nucleotide base sequences of HMG2 (SEQ ID NO:5) as well as the amino acid residue sequence of HMG-CoA reductase 2 (SEQ ID NO:6) are set forth hereinafter in the Sequence Listing.

The entire HMG1 gene comprises about 3360 base pairs (SEQ ID NO:3). Intact HMG-CoA reductase 1 comprises an amino acid sequence of about 1054 amino acid residues (SEQ ID NO:4). Thus, the minimal portion of the HMG1 gene that encodes an intact enzyme comprises base pairs from about nucleotide position 121 to about position 3282 of FIG. 3 (SEQ ID NO:3).

The entire HMG2 gene comprises about 3348 base pairs (SEQ ID NO:5). Intact HMG-CoA reductase 2 comprises about 1045 amino acid residues (SEQ ID NO:6). Thus, the minimal portion of HMG2 gene that encodes intact HMG-CoA reductase 2 comprises base pairs from defined. Liscum et al., *J. Biol. Chem*, 260(1):522 (1985). One segment containing a catalytic region has an apparent molecular weight of 62 kDa and comprises amino acid residues from about position 373 to about position 887. A second segment containing a catalytic region has an apparent molecular weight of 53 kDa segment and comprises amino acid residues from about position 460 to about position 887. The 62 kDa catalytically active segment is encoded by base pairs from about nucleotide position 1280 to about nucleotide position 2824 of FIG. 2 (SEQ ID NO:1). The 53 kDa catalytically active segment is encoded by base pairs from about nucleotide position 1541 to about nucleotide position 2824 of FIG. 2 (SEQ ID NO:1).

In a preferred embodiment, the utilized structural gene encodes the catalytic region and at least a portion of the linker region of HMG-CoA reductase. The linker region of hamster HMG-CoA reductase comprises amino acid residues from about position 340 to about position 373 or from about position 340 to about position 460, depending upon how the catalytic region is defined. These linker regions are encoded by base pairs from about nucleotide position 1180 to about nucleotide position 1283 or from about position 1180 to about position 1540 respectively of FIG. 2 (SEQ ID NO:1). The structural gene encoding the linker region is operatively linked to the structural gene encoding the catalytic region.

In one particularly preferred embodiment, a structural gene encoding a catalytically active, truncated HMG-CoA reductase enzyme can optionally contain base pairs encoding a small portion of the membrane region of the enzyme. A truncated hamster HMG-CoA reductase gene, designated HMGR-Δ227, comprising nucleotides 164–190 operatively linked to nucleotides about nucleotide position 121 to about position 3255 of FIG. 3 (SEQ ID NO:5).

By analogy to the truncated hamster structural gene, structural genes encoding polypeptides comprising catalytically active, truncated HMG-CoA reductase enzymes from yeast can also be used in accordance with the present invention.

The catalytic region of HMG-CoA reductase 1 comprises amino acid residues from about residue 618 to about residue 1054: i.e., the COOH-terminus. A structural gene that encodes the catalytic region comprises base pairs from about nucleotide position 1974 to about position 3282 of FIG. 3.

The linker region of HMG-CoA reductase 1 comprises an amino acid sequence from about residue 525 to about residue 617. A structural gene that encodes the linker region comprises nucleotides from about position 1695 to about position 1973 of FIG. 3. A structural gene encoding a polypeptide comprising the catalytic region and at least a portion of the linker region of yeast HMG-CoA reductase 1 preferably comprises the structural gene encoding the linker region of the enzyme operatively linked to the structural gene encoding the catalytic region of the enzyme.

Also by analogy to the truncated hamster gene, a truncated HMG1 gene can optionally contain nucleotide base pair sequences encoding a small portion of the membrane binding region of the enzyme. Such a structural gene preferably comprises base pairs from about nucleotide position 121 to about position 147 and from about position 1695 to about position 3282 of FIG. 3.

A construct similar to those above from an analogous portion of yeast HMG-CoA reductase 2 can also be utilized.

It will be apparent to those of skill in the art that the nucleic acid sequences set forth herein, either explicitly, as in the case of the sequences set forth above, or implicitly with respect to nucleic acid sequences generally known and not presented herein, can be modified due to the built-in redundancy of the genetic code and non-critical areas of the polypeptide that are subject to modification and alteration. In this regard, the present invention contemplates allelic variants of structural genes encoding a polypeptide having HMG-CoA reductase activity.

The previously described DNA segments are noted as having a minimal length, as well as total overall lengths. That minimal length defines the length of a DNA segment having a sequence that encodes a particular polypeptide having HMG-CoA reductase activity. As is well known in the art, so long as the required DNA sequence is present, (including start and stop signals), additional base pairs can be present at either end of the segment and that segment can still be utilized to express the protein. This, of course, presumes the absence in the segment of an operatively linked DNA sequence that represses expression, expresses a further product that consumes the enzyme desired to be expressed, expresses a product other than the desired enzyme or otherwise interferes with the structural gene of the DNA segment.

Thus, so long as the DNA segment is free of such interfering DNA sequences, a DNA segment of the invention can be up to 15,000 base pairs in length. The maximum size of a recombinant DNA molecule, particularly a plant integrating vector, is governed mostly by convenience and the vector size that can be accommodated by a host cell, once all of the minimal DNA sequences required for replication and expression, when desired, are present. Minimal vector sizes are well known.

D. Recombinant DNA Molecules

A recombinant DNA molecule of the present invention can be produced by operatively linking a vector to a useful DNA segment discussed before to form a plasmid such as those discussed herein. A particularly preferred recombinant DNA molecule is discussed in detail in Example 1, hereafter. A vector capable of directing the expression of a polypeptide having HMG-CoA reductase activity is referred to herein as an HMG-CoA reductase "plant integrating vector".

Such plant integrating vectors contain control elements that direct and regulate expression, including a promoter, a marker, a terminator and insertion sequences (see FIG. 5). The polypeptide coding genes are operatively linked to the plant integrating vector to allow the promoter sequence to direct RNA polymerase binding and expression of the desired polypeptide coding gene.

Useful in expressing the polypeptide coding gene are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chau et al., *Science*, 244:174–181 (1989). The promoter preferably comprises a promoter sequence whose function in regulating expression of the structural gene is substantially unaffected by the amount of sterol or squalene in the cell. As used herein, the term "substantially unaffected" means that the promoter is not responsive to direct feedback control by the sterols or squalene accumulated in transformed cells or transgenic plants.

A promoter is also selected for its ability to direct the transformed plant cell's or transgenic plant's transcriptional activity to the structural gene encoding a polypeptide having HMG-CoA reductase activity. Structural genes can be driven by a variety of promoters in plant tissues. Promoters can be near-constitutive, such as the CaMV 35S promoter, or tissue specific or developmentally specific promoters affecting dicots or monocots.

As exemplified and discussed in detail hereinafter, where the near-constitutive promoter CaMV 35S is used to transform tobacco plants, increases in total sterol and squalene accumulation are found in a variety of transformed plant tissues (e.g. callus, leaf, seed and root). Alternatively, the effects of transformation (e.g. increased amount of a gene coding for HMG-CoA reductase, increased total sterol accumulation and increased squalene accumulation) can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

A plant integrating vector containing a structural gene coding for a polypeptide having HMG-CoA reductase activity is engineered to be under control of the Lectin promoter and that vector is introduced into soybean plants using a protoplast transformation method. Dhir et al., *Plant Cell Reports*, 10:97 (1991). The expression of the polypeptide having HMG-CoA reductase activity is directed specifically to the seeds of the transgenic plant. In this way, a transgenic soybean seed having increased squalene accumulation is produced. Such seeds can then be used to extract oil containing enhanced levels of squalene. As set forth hereinafter, such squalene-enhanced oil is characterized by a greater thermal stability when compared to non-squalene-enhanced oil.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci. U.S.A.*, 87:4144–48 (1990)), corn alcohol dehydrogenase 1 (Vogel et al., *J. Cell Biochem.*, (supplement 13D, 312) (1989)), corn zein 19KD gene (storage protein) (Boston et al., *Plant Physiol.*, 83:742–46), corn light harvesting complex (Simpson, *Science*, 233:34 (1986), corn heat shock protein (O'Dell et al., *Nature*, 313:810–12 (1985), pea small subunit RuBP Carboxylase (Poulsen et al., *Mol. Gen. Genet.*, 205:193–200 (1986); Cushmore et al., *Gen. Eng. of Plants*, Plenum Press, New York, 29–38 (1983), Ti plasmid mannopine synthase (Langridge et al., *Proc. Natl. Acad. Sci. U.S.A.*, 86:3219–3223 (1989), Ti plasmid nopaline synthase (Langridge et al., *Proc. Natl. Acad. Sci. U.S.A.*, 86:3219–3223 (1989), petunia chalcone isomerase (Van Tunen et al., *EMBO J.*, 7:1257 (1988), bean glycine rich protein 1 (Keller et al., *EMBO J.*, 8:1309–14 (1989), CaMV 35s transcript (O'Dell et al., *Nature*, 313:810–12 (1985) and Potato patatin (Wenzler et al., *Plant Mol. Biol.*, 12:41–50 (1989). Preferred promoters are the cauliflower mosaic virus (CaMV 35S) promoter and the S-E9 small subunit RuBP carboxylase promoter.

The choice of which plant integrating vector and ultimately to which promoter a polypeptide coding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding gene, i.e., the gene encoding HMG-CoA reductase activity, included in the DNA segment to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other plant integrating vector systems are known to function in plants including pCaMVCN transfer control vector described by Fromm et al., *Proc. Natl. Acad. Sci. U.S.A.*, 82:5824 (1985). Plasmid pCaMVCN (available from Pharmacia, Piscataway, N.J.) includes the cauliflower mosaic virus CaMV 35S promoter.

The use of retroviral plant integrating vectors to form the recombinant DNAs of the present invention is also contemplated. As used herein, the term "retroviral plant integrating vector" refers to a DNA molecule that includes a promoter sequence derived from the long terminal repeat (LTR) region of a retrovirus genome.

In preferred embodiments, the vector used to express the polypeptide coding gene includes a selection marker that is effective in a plant cell, preferably a drug resistance selection marker. One preferred drug resistance marker is the gene whose expression results in kanamycin resistance; i.e., the chimeric gene containing the nopaline synthae promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988).

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the plant integrating vector. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase. Thus, the products of the reaction are DNA segments carrying synthetic linker sequences at their ends. These DNA segments are then cleaved with the appropriate restriction endonuclease and ligated into a plant integrating vector that has been cleaved with an enzyme that produces termini compatible with those of the synthetic linker. Synthetic linkers containing a variety of restriction endonuclease sites are commercially available from a number of sources including New England BioLabs, Beverly, Mass.

Also contemplated by the present invention are RNA equivalents of the above described recombinant DNA molecules.

A preferred recombinant DNA molecule utilized in accordance with the present invention is plasmid HMGRΔ227-pKYLX71.

E. Transformed Plant Cells, Transgenic Plants, Processes of Transformation and Processes of Regeneration The amount of a gene coding for a polypeptide having HMG-CoA reductase activity is increased by transforming a desired plant cell with a suitable vector that contains that added exogenous structural gene. Expression of that gene in the transformed plant cell and transgenic plants developed from that transformed plant cell enhances the activity of HMG-CoA reductase.

Methods for transforming polypeptide-coding genes into plant cells include Agrobacterium-mediated plant transformation, protoplast transformation, gene transfer into pollen, injection into reproductive organs and injection into immature embryos. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes.

In addition, Agrobacteria containing both armed and disarmed Ti genes can be used for the transformations. Both types of transforming systems are illustrated herein. Transformants from the former system result in callus from which the desired squalene or sterol can be obtained, whereas transformants obtained from the latter, disarmed Ti genes can be regenerated into complete transgenic plants from whose tissues, e.g. leaf, seed and root, the desired chemicals can be obtained.

In those plant strains where Agrobacterium-mediated transformation is efficient, it is the method of choice because of the facile and defined nature of the gene transfer.

Agrobacterim-mediated transformation of leaf disks and other tissues such as cotyledons and hypocotyls appears to be limited to plant strains that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. U.S.A.*, 84:5345 (1987). Therefore, commercially important cereal grains such as rice, corn, and wheat must usually be transformed using alternative methods. However, as mentioned above, the transformation of asparagus using Agrobacterim can also be achieved. See, for example, Bytebier, et al., *Proc. Natl. Acad. Sci. U.S.A.*, 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis. A transgenic plant containing a single structural gene that encodes a polypeptide having HMG-CoA reductase activity; i.e., an independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced HMG-CoA reductase activity, sterol accumulation, or squalene accumulation or all three, relative to a control (native, non-transgenic) or an independent segregant transgenic plant. A homozygous transgenic plant exhibits enhanced HMG-CoA reductase activity, sterol and squalene accumulation as compared to both a native, non-transgenic plant and an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide having HMG-CoA activity. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimiya et al., *Mol. Gen. Genet*, 204:204 (1986); Callis et al., *Genes and Development*, 1:1183 (1987); and Marcotte et al., *Nature*, 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters*, 2:74 (1985); Toriyama et al., *Theor. Appl. Genet.*, 73:16 (1986); Yamada et al., *Plant Cell Rep.*, 4:85 (1986); Abdullah et al., *Biotechnology*, 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized.

Using that latter technology, DNA is carried through the cell wall and into the cytoplasm on the surface of small metal particles as described in Klein et al., *Nature*, 327:70 (1987); Klein et al., *Proc. Natl. Acad. Sci, U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell*, 2:603–618 (1990); Klein, T. M. et al., *Plant Physiol.*, 91:440–444 (1989); Klein, T. M. et al., *Proc. Natl. Acad. Sci. U.S.A.*, 85:8502–8505 (1988); and Tomes, D. T. et al., *Plant Mol. Biol.*, 14:261–268 (1990). Transformation of tissue explants eliminates the need for passage through a protoplast stage and thus speeds the production of transgenic plants.

Thus, the amount of a gene coding for a polypeptide having HMG-CoA reductase activity can be increased in monocotyledonous plants such as corn by transforming those plants using particle bombardment methods. Maddock et al., *Third International Congress of Plant Molecular Biology*, Abstract 372 (1991). By way of example, a plant integrating vector containing a structural gene for HMG-CoA reductase and an appropriate selectable marker is transformed into a suspension of embryonic maize (corn) cells using a particle gun to deliver the DNA coated on microprojectiles. Transgenic plants are regenerated from transformed embryonic calli that express HMG-CoA reductase.

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo 1986*, Butterworth, Stoneham, Mass., pp. 27–54 (1986).

The development or regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide having HMG-CoA activity introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Mature regenerated transgenic plants are obtained that exhibit increased sterol or squalene accumulation due to expression of the HMG-CoA reductase polypeptide gene. Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants. The presence of the added gene in the progeny is assessed as discussed hereinafter.

A transgenic plant of the present invention containing a desired HMG-CoA reductase polypeptide is cultivated using methods well known to one skilled in the art. Any of the transgenic plants of the present invention can be cultivated to isolate the desired sterol or squalene products they contain.

A transgenic plant of this invention thus has an increased amount of a structural gene that encodes a polypeptide having HMG-CoA reductase activity. A preferred transgenic plant is an independent segregant for the added HMG-CoA reductase structural gene and can transmit that gene and its activity to its progeny. A more preferred transgenic plant is homozygous for that gene, and transmits that gene to all of its offspring on sexual mating.

A transgenic plant of the invention accumulates sterols and, particularly non-delta-5 sterols relative to a native plant. A transgenic plant of the invention also accumulates squalene relative to a native, non-transgenic plant. A transgenic plant also exhibits resistance to pests such as the hornworms and budworms as is discussed hereinafter.

F. Development of Commercial Hybrid Seed

Seed from a transgenic plant is grown in the field or greenhouse, and resulting sexually mature transgenic plants are self-pollinated to generate true breeding plants. The progeny from these plants become true breeding lines that are evaluated for sterol or squalene accumulation, preferably in the field, under a range of environmental conditions.

The commercial value of a transgenic plant with increased sterol or squalene accumulation is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, sterol or squalene accumulation is preferably bred into a large number of parental lines so that many hybrid combinations can be produced.

Adding an enhanced sterol or squalene accumulation trait to an agronomically elite line is accomplished by a variety of techniques well known to those of skill in the art. For example, parent transgenic plants that are either homozygous or contain a single independent segregatable gene that encodes a polypeptide having HMG-CoA activity and thus for enhanced sterol or squalene accumulation are crossed with lines having other desirable traits, such as herbicide resistance (U.S. Pat. No. 4,761,373) produce hybrids. Preferably, transgenic plants homozygous for enhanced sterol or squalene accumulation are used to generate hybrids.

For example, a transgenic plant homozygous for enhanced sterol accumulation is crossed with a parent plant having other desired traits. The progeny, which are heterozygous or independently segregatable for enhanced sterol accumulation, are backcrossed with the parent to obtain transgenic plants having enhanced sterol accumulation and the other desired traits. The backcrossing of progeny with the parent may have to be repeated more than once to obtain a transgenic plant that possesses all desirable traits.

Alternatively, transgenic plants with an enhanced sterol or squalene accumulation trait are made multiply transgenic by introducing into such plants other genes that encode and express other desirable traits, or are mutated as with radiation, e.g. X-rays or gamma rays, as in U.S. Pat. No. 4,616,099, whose disclosures are incorporates by reference. Thus, the present invention also contemplates mutants and genetically engineered derivatives of transgenic plants having enhanced sterol or squalene accumulation.

G. Accumulation of Sterols in Transgenic Plants

The present invention provides processes for increasing the accumulation of sterols, particularly non-delta-5 sterols, in transgenic plants. This is accomplished by increasing the amount of a gene encoding for a polypeptide having HMG-CoA reductase activity and subsequent expression of that encoded polypeptide.

In native, non-transgenic plants sterol accumulation is usually equal to about 0.3 weight percent of the dry weight on the plant. The predominant sterols accumulated by such normal plants are campesterol, sitosterol and stigmasterol. These sterols, $\Delta 5$-derivatives of cycloartenol that have undergone desaturation of the 5(6) carbon-carbon bond of cycloartenol, comprise over 80 weight percent of total sterols in native plants. Cycloartenol normally comprises from about 3 to about 30 percent of the total sterols present in such a plant.

Transgenic plants having an increased amount of a gene encoding a polypeptide having HMG-CoA reductase activity demonstrate a marked increase in total sterol accumulation when compared to a native, non-transgenic plant of the same strain. Further, the predominant sterol found in such transgenic plants is cycloartenol, which represents from about 60 to about 70 weight percent of total sterols of a transgenic plant.

Thus, the present invention provides transgenic plants that overaccumulate sterols relative to a native, non-transgenic plant. Transgenic plants with a single added gene accumulate total sterol to a level about twice that found in native, non-transgenic plants. In particular, such transgenic plants accumulate non-delta-5 sterols (e.g. cycloartenol) to a level from about ten to about one hundred times greater than found in native, non-transgenic plants.

These results are surprising and unexpected in light of studies relating HMG-CoA reductase activity and sterol accumulation in other organisms.

In yeast, increases in HMG-CoA reductase activity are associated with increases in squalene, 4,14-dimethylzymosterol and 14-methylfecosterol. Downing et al., *Biochemical and Biophysical Research Communications*, 94(3): 974–979 (1980). Increases in HMG-CoA reductase activity of yeast were not associated with increases in lanosterol, (a sterol of yeast analogous to cycloartenol). Benveniste, *Ann. Rev. Plant Physiol.*, 37:275–308 (1986).

In non-photosynthetic microorganisms, light-induced increases in HMG-CoA reductase activity were not associated with increases in sterol accumulation. Tada et al., *Plant and cell Physiology*, 23(4):615–621(1982).

H. Increased Squalene Accumulation

The present invention provides processes for increasing the accumulation of squalene in transgenic plants. This is accomplished by increasing the amount of a gene encoding for a polypeptide having HMG-CoA reductase activity and subsequent expression of that encoded polypeptide in the transgenic plant.

Squalene has use as a bactericide, a pharmaceutical intermediate, and cosmetic ingredient. Further, enhanced squalene levels in or on rind can serve to protect citrus fruit against the harmful effects of chilling and freezing.

There is an inverse relationship between squalene levels in the epicuticular wax of grapefruit and severity of chilling injury in that fruit. Norby and McDonald, *Lipids*, 25:807–810 (1990), *J. Agric. Food Chem.*, 39:957–962 (1991), and U.S. Pat. 4,921,715. Further, where squalene was applied as a spray or dip to grapefruit, it prevented chill injury. Norby and McDonald, *Hortscience*, 25:94 (1990).

In a preferred embodiment, the present invention provides processes for increasing the accumulation of squalene in a transgenic citrus plant. This is accomplished by increasing the amount of a gene encoding for a polypeptide having HMG-CoA reductase activity and subsequent expression of that encoded polypeptide in the transgenic plant.

The amount of a gene encoding for a polypeptide having HMG-CoA reductase activity is increased in a citrus plant by transforming a citrus plant cell in accordance with a process of the present invention. Means for transforming citrus plant cells using Agrobacterium-mediated transformation techniques are well known in the art.

Still further, squalene is reported to improve the heat stability of vegetable oils. The addition of squalene to rapeseed oil was found to retard the formation of thermally unstable polar compounds in rapeseed oil heated to about 170° C. for about 10 hours. Malecka, N., *Die Nahrung*, 35(5):541 (1991).

Transgenic tobacco plant seeds of the present invention have an increased accumulation of squalene when compared to seeds of a native, non-transgenic seed (See Example 10 hereinafter). Thus, in another aspect, the present invention contemplates transgenic plant seeds whose oil contains an increased accumulation of squalene when compared to oil obtained from a native, non-transgenic seed.

In native, non-transgenic plants squalene accumulation is less than about 0.01 weight percent of the dry weight on the plant. In transgenic plants of the present invention squalene accumulation increases to a level of from about 0.115 weight percent of dry weight (tobacco and soybean) to 0.56 weight percent (cotton) (See Examples 5–9 hereinafter).

I. Harvesting of Sterols and Squalene

If desired, after cultivation, the transgenic plant is harvested to recover the sterol or squalene product. This harvesting step can consist of harvesting a callus culture, the entire plant, or only the leaves, or roots of the plant. This step can either kill the plant or, if only a non-essential portion of the transgenic plant is harvested, can permit the remainder of the plant to continue to grow.

In preferred embodiments, this harvesting step further comprises the steps of:

(i) homogenizing at least a sterol-containing or a squalene-containing portion of the transgenic plant to produce a plant pulp and using the sterol- or squalene-containing pulp directly, as in dried pellets or tablets as where an animal food is contemplated; or (ii) extracting the squalene or sterol(s) from the plant pulp with an appropriate solvent such as an organic solvent or by supercritical extraction [Favati et al., *J. Food Sci.*, 53:1532 (1988) and the citations therein] to produce a sterol- or squalene-containing liquid solution or suspension; and (iii) isolating the squalene or sterol(s) from the solution or suspension.

At least a portion of the transgenic plant is homogenized to produce a plant pulp using methods well known to one skilled in the art. This homogenization can be done manually, by a machine, or by a chemical means as long as the transgenic plant portions are broken up into small pieces to produce a plant pulp. This plant pulp consists of a mixture of squalene or the sterol of interest, residual amounts of precursors, cellular particles and cytosol contents. This pulp can be dried and compressed into pellets or tablets and eaten or otherwise used to derive the benefits, or the pulp can be subjected to extraction procedures.

The sterol or squalene can be extracted from the plant pulp produced above to form a sterol- or squalene-containing solution or suspension. Such extraction processes are common and well known to one skilled in this art. For example, the extracting step can consist of soaking or immersing the plant pulp in a suitable solvent. This suitable solvent is capable of dissolving or suspending the squalene or sterol present in the plant pulp to produce a sterol- or squalene-containing solution or suspension. Solvents useful for such an extraction process are well known to those skilled in the art and include several organic solvents and combinations thereof such as methanol, ethanol, isopropanol, acetone, acetonitrile, tetrahydrofuran (THF), hexane, and chloroform as well as water-organic solvent mixtures. A vegetable oil such as peanut, corn, soybean and similar oils can also be used for this extraction as can steam distillation.

A whole plant or callus culture with an added, exogenous structural gene for a polypeptide having HMG-CoA reductase activity is grown under suitable conditions for a period of time sufficient for squalene or sterols to be synthesized and accumulated. The sterol- or squalene-containing plant cells, preferably in dried form, are then lysed chemically or mechanically, and the squalene or sterol is extracted from the lysed cells using a liquid organic solvent or steam distillation, as described before, to form a sterol- or squalene-containing liquid solution or suspension. The squalene or sterol is thereafter isolated from the liquid solution or suspension by usual means such as chromatography.

The squalene or sterol is isolated from the solution or suspension produced above using methods that are well known to those skilled in the art of squalene and sterol isolation. These methods include, but are not limited to, purification procedures based on solubility in various liquid media, chromatographic techniques such as column chromatography and the like.

J. Pest Resistance of Transgenic Plants

Certain sterols accumulated by a transgenic plant of the present invention have use as systemic insecticidal or pesticidal agents. As set forth before, because insects are unable to synthesize de novo the steroid nucleus, they depend upon external, dietary sources of delta-5 sterols for production of necessary steroid compounds such as ecdysteroids. See, e.g. Costet et al., *Proc. Natl. Acad. Sci. U.S.A.*, 84:643 (1987) and Corio-Costet et al., *Archives of Insect Biochem. Physiol.*, 11:47 (1989).

This embodiment of the present invention relates to a process of increasing pest resistance of a transgenic plant comprising transforming a plant cell of a native, non-transgenic plant with a recombinant DNA molecule comprising a vector operatively linked to a DNA segment that encodes the catalytic region of HMG-CoA reductase, and a promoter suitable for driving the expression of said reductase in that plant, and regenerating a transgenic plant from the transformed plant cell. In preferred practice, the DNA segment also encodes at least a portion of the linker region but not the membrane binding region of HMG-CoA reductase. Use of the hamster gene is particularly preferred. The resulting transgenic plant exhibits enhanced resistance to insect pests.

A transgenic plant is then preferably grown to sexual maturity and used to transmit its enhanced pest resistance to its offspring. Transgenic plants can also themselves be used agriculturally.

Tobacco hornworm larvae grown on the leaves of transgenic plants regenerated from plant cells transformed with a truncated hamster HMG-CoA reductase gene, which transgenic plants have increased levels of non-delta-5 sterol and, particularly cycloartenol, demonstrated retarded development. Preliminary studies also indicate that tobacco bud worms (*Heliothis virescens*) fed on leaves of a similar transgenic plant exhibited retarded development under similar conditions.

Other insects such as *Locusta migratoria* show marked developmental arrest and growth abnormalities when reared on plants deficient in delta-5 sterols. Costet et al., *Proc. Soc. Natl. Acad. Sci., U.S.A.*, 84:643 (1987); Corro-Costet et al., *Archives Insect Biochem. Physiol.*, 11:47 (1989).

Further, initial feeding studies show that the growth and development at various stages of Heliothis and European corn borer, *Ostrinia nubialis*, are markedly inhibited by feeding those insect pests on artificial diets having reduced levels of delta-5 sterols and increased levels of non-delta-5 sterols.

K. Harvesting of Transgenic Seed Oil

Oil is extracted from transgenic plant seeds of the present invention by methods well known in the art. By way of example, oil can be extracted from plant seeds using extraction methods set forth above for harvesting sterols and squalene from transgenic plants. Alternatively, oil can be extracted from transgenic plant seeds by usually used methods for obtaining seed oils such as by crushing the seeds to produce a pulp and then pressing the pulp to obtain oil. The pulp can also be extracted with appropriate solvents (e.g. benzene) to obtain the oil. *Industrial Chemistry: A Manual for the Student and Manufacturer*, ed. by A. Rogers and A. B. Aubert, D. Van Nostrand Co., New York, pages 547–548 (1912).

The following examples illustrate the best mode of carrying out the invention and are not to be construed as limiting of the specification and claims in any way.
Best Mode for Carrying out the Invention

EXAMPLE 1

Transformation of Plant Cells

Plant cells were transformed in accordance with standard methods for expressing foreign genes in plants. Schardl et al., *Gene*, 61:1–11 (1987). A pKYLX series of vectors was used as the expression system. Preferred vectors are plasmids pKYLX6 and pKYLX7. Berger et al., *Proc. Natl. Acad. Sci. U.S.A.*, 86: 8402–8406. (1989).

Transformations were performed with a truncated Hamster HMG-CoA reductase gene (HMGR-Δ227) obtained from the laboratories of Dr. J. L. Goldstein, See, e.g., Gil et al., *Cell*, 41:249–258(1985); Bard et al., *Journal of General Microbiology*, 125:415–420(1981).

The HMGR-Δ227 gene was incorporated into modified vectors pKYLX6 (an *E. coli* vector designed for intermediate constructs) and pKYLX7 (an *A. tunefaciens* vector designed for integration of cloned genes). Berger et al., *Proc. Natl. Acad. Sci. U.S.A.*, 86:8402–8406 (1989). The modified vectors pKYLX61 and pKYLX71 contained Hind III, Xho I, Bam HI, Pst I, and Sst I sites in place of the original Hind III Sst I fragment multiple cloning site region.

The HMGR-Δ227 gene was digested with Bam HI and Sst I, and the approximately, 2500 bp HMGR-Δ227-Bam HI-Sst I fragment was inserted into plasmid pKYLX61. The resulting HMGRΔ227-pKYLX61 construct was cleaved with Eco RI and Cla I, and an approximately 4000 bp fragment containing the promoter-gene-terminator portion was inserted into corresponding sites of pKYLX71 to generate plasmid HMGRΔ227-pKYLX71 (see FIG. 5). In plasmid HMGRΔ227-KYLX71, the truncated HMGR-Δ227 gene is under control of the strong, constitutive CaMV 35S promoter.

The HMGRΔ227-pKYLX71 plasmid was mobilized into *Agrobacterium tumefaciens* by a standard triparental mating between *E. coli*, harboring the HMGRΔ227-pKYLX71 construct, *Argrobacterium tumefaciens*, harboring a disarmed Ti-plasmid, GV3850, and *E. coli* harboring the conjugation helper plasmid pRK2013. See, e.g., Schardl, et al., *Gene*, 61:1–11 (1987); Ditta et al., *Proc. Natl. Acad. Sci. U.S.A.* 77:7347–7351 (1980). As a result of the cross, Agrobacterium harboring the HMGRΔ227-pKYLX71 construct, was selected for by resistance to rifampicin (encoded on the chromosome of Agrobacterium), and to tetracycline and kanamycin (encoded on the pKYLX71 vector).

Alternatively, the HMGR Δ-227-KYLX71 plasmid is mobilized into *Agrobacterium tumefaciens* strain 281, which contains a fully armed T-DNA plasmid to form a binary plasmid strain A281-Δ227. See, e.g., Schardl et al. *Gene*, 61:1–11 (1987) and Montoya et al., *J. Bacteriol.*, 129:101 (1977) (See Example 7 hereinafter).

*Nicotiana tabacum L. cv. xanthii* (*N. tabacum*) was transformed by the well known "leaf disk method". Horsch et al., *Science* 27:1229–1231 (1985). Leaf disks were incubated with Agrobacteria containing plasmid Δ227-pKYLX71 for about 3 days. Transformed tissue was selected for by resistance to kanamycin (encoded by the pKYLX71 vector), cured of Agrobacteria using the antibiotic mefoxin, and regenerated into whole plants. Horsch et al., *Science*, 27:1229–1231 (1985).

Transgenic plant tissue was checked for the presence of integrated copies of the HMGR Δ227 gene sequences by the method of Mettler, *Plant Mol. Biol. Reporter*, 5:346–349 (1987). RNA transcription levels were determined by northern blotting or S-1 protection assays. Maniatis et al., *Molecular Cloning: A Laboratory Manual*, Cold Spring Harbour Lab., Cold Spring Harbour, N.Y. (1982).

Transgenic plants exhibiting HMG-CoA reductase activity greater than native, non-transgenic (control) plants or transgenic plants regenerated from plant cells transformed without the HMGR-Δ227-construct were sexually crossed with themselves, to generate progeny.

EXAMPLE 2

HMG-CoA Reductase Enzyme Activity in Transgenic Plants

Transgenic plants were screened for expression of the truncated HMGR gene by examining HMG-CoA reductase activity in the 100,000×G supernatant of lysed cells using a standard assay, Chappell et al., *Plant Phyiol.*, 85:469–473 (1987).

Soluble HMG-CoA reductase enzyme activity was measured in callus cultures grown on selection (kanamycin) medium, seedlings germinated in the presence of kanamycin or on moistened filter paper, and leaves of various sizes from plants grown in the greenhouse. Examplary results of studies of HMG-CoA reductase activity in leaves from greenhouse-grown plants are also summarized in Table 2 below:

TABLE 2

| Plant Sample No. | Total HMG-CoA Reductase Activity (pmol/hr./leaf) | % of Control |
| --- | --- | --- |
| Control | | |
| 30 | 258 | 100 |
| Transgenic | | |
| 5 | 860 | 300 |
| 14 | 1,100 | 390 |
| 15 | 633 | 220 |
| 18 | 456 | 160 |
| 23 | 713 | 250 |

The control plant, 30, was transformed with a selection marker but not with the $\Delta 227$ gene. Transgenic plants 5, 14, 15, 18 and 23 were regenerated from plant cells transformed with the HMGR-$\Delta 227$ gene, as discussed above.

Total HMG-CoA reductase activity was 1.6 to 3.9 times greater in transgenic plants harboring the $\Delta 227$ gene as compared to the control plant.

EXAMPLE 3

Sterol Accumulation in Transgenic Plants

Regenerated, transgenic *N. tabacum*, from cells transformed with the HMGR-$\Delta 227$ gene according to the process of Example 1 were analyzed for total sterol content. The results are presented in Table 3.

TABLE 3

| Plant Sample | HMG-CoA Reductase (pmol\mg dry wt.) | Total Sterols (% of dry wt) |
| --- | --- | --- |
| Control Plants (n = 6) | 2.00 ± 0.19 | 0.27 ± 0.02 |
| Transgenic Plants (n = 12) | 5.75 ± 1.55 | 0.89 ± 0.17 |

Transgenic plants had elevated HMG-CoA reductase activity and increased sterol content.

In addition to determining total sterol content, transgenic *N. tabacum* were examined for the accumulation of squalene and specific sterols. The designated plant tissues were lyophilized and heated with agitation in an alcohol/water solution containing potassium hydroxide to effect extraction and saponification of sterols and sterol esters. Free sterols were then extracted into heptane and measured by gas chromatography using an internal standard. The results of such an analysis in a control (Cntrl) and a transgenic (Trg) plant are presented in Table 4.

TABLE 4

| Accumulated Product | Percent Dry Weight of Squalene and Sterols | | | | | |
| --- | --- | --- | --- | --- | --- | --- |
| | Callus | | Leaf | | Root | |
| | Cntrl | Trg | Cntrl | Trg | Cntrl | Trg |
| Squalene | tr | 0.025 | 0.01 | 0.126 | tr | 0.019 |
| Sterols | | | | | | |
| Campesterol | 0.009 | 0.021 | 0.057 | 0.056 | 0.058 | 0.022 |
| Cholesterol | 0.004 | tr | tr | tr | tr | tr |
| Cycloartenol | 0.003 | 0.258 | 0.011 | 0.678 | 0.039 | 0.642 |
| Sitosterol | 0.027 | 0.077 | 0.083 | 0.187 | 0.029 | 0.194 |
| Stigmasterol | 0.003 | 0.012 | 0.132 | 0.078 | tr | 0.238 | tr = trace (<0.001 percent dry wt.)

In the control plant, cycloartenol represented from about 3(0.011/0.283) percent dry weight (leaf) to about 30(0.039/0.126) percent dry weight (root) of total sterol accumulation. The predominant sterols accumulated by control plants (i.e. sitosterol, campesterol) are $\Delta 5$-sterol derivatives of cycloartenol that have undergone additional metabolic transformation.

As a result of transformation with the HMGR-$\Delta 227$ gene, the ratio of cycloartenol to its derivatives is reversed. In transgenic plants, cycloartenol accumulation represents from about 60 (root) to about 70 (leaf) percent by weight of total sterol accumulation.

These data show that transgenic plants of the present invention overaccumulate sterols relative to a native, non-transgenic plant. Transgenic, heterozygous plants overaccumulate total sterols to a level about twice that found in a native plant. The data further show that transgenic plants containing a single added, exogenous gone over-accumulate cycloartenol to a level about ten to about one hundred times greater than found in a native plant.

EXAMPLE 4

Insecticidal Effects of Transgenic Plants

First instar larvae of the tobacco pests tobacco hornworm (*Maduca sexta*), were placed onto leaves of control or HMGR-$\Delta 227$ transgenic *N. tabacum* on a moistened filtered paper in a petri dish. Additional leaf material, from control or transgenic plants, was added to each dish, and the larvae were grown for an additional 7 days. Larvae were then examined to determine growth and development. The results are presented in Table 5.

TABLE 5

| | Control (n = 14) | Transgenic (n = 13) |
| --- | --- | --- |
| Development | | |
| % of larvae in second instar | 28.6 | 100 |
| % of larvae in premolt or third instar | 71.4 | 0 |
| Growth | | |
| Fresh Wet Weight (mg) | 42.8 | 24.4 |

Tobacco hornworm (*Manduca sexta*) larvae grown on leaves from transgenic plants (from HMGR-$\Delta 227$-transformed cells) demonstrated retarded development (no progression beyond the second instar stage) and inhibited growth (wet weight) as compared to controls. The cycloartenol levels of the control and transgenic plants used in this study were 0.017 and 1.02 percent of dry leaf weight, respectively. This study thus illustrates both the process of increasing the accumulation of cycloartenol in a plant and of enhancing pest resistance in a plant.

Preliminary studies with a member of the Heliothis group of insect pests, the tobacco bud worm (*Heliothis virescens*), indicate a slower growth rate for insects fed on leaves of transgenic plant 14 (Example 2) than on leaves of the native, non-transgenic, control plant 30 (Example 2).

EXAMPLE 5

Homozygous Transgenic Plants

One of the previously described transformed plants, plant 14 of Example 2, was selfed; i.e., sexually mated with itself.

Twelve seeds from that cross were germinated and raised into plants. The tissues of those siblings were then analyzed for HMG-CoA reductase activity, total squalene (squalene plus squalene monoepoxide), and total sterol content as described in Example 3. The specific activity of HMG-CoA reductase was also calculated. The results of that assay compared to similar data from siblings from a selfing control plant 30 (Example 2) are presented in Table 6, below.

TABLE 6

| Plant | HMGR Activity[1] | Protein[2] | Specific Activity[3] | Sterols[4] | Squalenes[5] |
|---|---|---|---|---|---|
| 30-1 | 3.78 | 30.22 | 184 | 0.20 | <0.01 |
| 30-2 | 2.20 | 30.00 | 146 | 0.25 | <0.01 |
| 30-3 | 1.44 | 18.70 | 154 | 0.29 | <0.01 |
| 30-4 | 2.13 | 23.67 | 180 | 0.31 | <0.01 |
| 30-5 | 1.70 | 19.27 | 176 | 0.36 | <0.01 |
| 30-6 | 1.77 | 19.32 | 183 | 0.22 | <0.01 |
| 14-1 | 1.36 | 23.60 | 115 | 0.21 | 0.142 |
| 14-2 | 2.07 | 26.55 | 156 | 0.17 | 0.127 |
| 14-3 | 10.28 | 17.60 | 1168 | 1.10 | 0.101 |
| 14-4 | 7.08 | 27.25 | 520 | 0.74 | 0.114 |
| 14-5 | 4.13 | 20.92 | 394 | 1.59 | 0.107 |
| 14-6 | 1.58 | 11.00 | 143 | 0.25 | 0.086 |
| 14-7* | 20.35 | 16.77 | 2426 | 2.05 | 0.119 |
| 14-8 | 4.87 | 24.20 | 402 | 0.97 | 0.174 |
| 14-9 | 2.37 | 12.95 | 366 | 0.19 | 0.126 |
| 14-10 | 7.94 | 11.00 | 1444 | 1.02 | 0.075 |
| 14-11 | 2.56 | 15.25 | 334 | 1.10 | 0.082 |
| 14-12 | 4.39 | 21.10 | 416 | 1.29 | 0.130 |

[1]pmoles/0.5 hours.
[2]micrograms (μg).
[3]pmoles of enzyme/hour/mg of total protein.
[4]percentage of dry weight.
[5]squalene plus squalene monoepoxide (percentage of dry weight
*this plant died.

The phenotype for altered sterol composition segregated in a standard Mendelian manner with a ratio of three plants containing the elevated HMG-CoA reductase activity to one plant lacking the elevated HMG-CoA reductase activity.

On the basis of the above data, the plants were classified as (a) having no added HMG-CoA reductase gene, or (b) containing the added gene. Illustratively, plant 14-2 was thus determined to lack the added gene and plant 14-8 was determined to contain the added gene.

Southern blot analyses were performed on the transformed plants and confirmed the presence of the integrated gene.

These data show that seeds from a transformed plant are capable of expressing enhanced squalene and sterol accumulation.

Taken together with the data of Example 3, these data show that the transgenic plants of the present invention overaccumulate squalene, total sterol, and particularly non-utilizable sterols relative to a native plant and that such plants are capable of producing seeds, which germinate into transgenic plants that overaccumulate squalene and those sterols.

Seeds from a selfing of transgenic plant 14-8 were deposited pursuant to the Budapest Treaty requirements with the American Type Culture Collection (ATCC) at 12301 Parklawn Drive, Rockville, Md. 20852 U.S.A. on Sep. 28, 1990, and were assigned accession number ATCC 40904.

The above deposit is made for a term of at least thirty (30) years and at least five (5) years after the most recent request for the furnishing of a sample of the deposit was received by the depository.

EXAMPLE 6

Transformation of Cotton

The cotton plant cell line Coker 312-5A was transformed with HMGR-Δ227 gene incorporated into plasmid pKYLX6. Transformation by Agrobacterium-mediated gene transfer was accomplished using the method of Trolinder et al., *Plant Cell Reports*, 6:231–234 (1987).

Total sterol, delta-5 sterol, non-delta-5 sterol and squalene levels were determined in control, non-transgenic and transgenic calli as described in Example 3. The results of those studies are presented below in Table 7.

TABLE 7

| Plant | Total Sterol | Non-Util Sterol[1] | Util Sterol[2] | Squalene |
|---|---|---|---|---|
| Control | 0.16 | 0.03 | 0.13 | <0.002 |
| Tr-1 | 0.48 | 0.39 | 0.09 | 0.2 |
| Tr-2 | 0.53 | 0.44 | 0.09 | 0.39 |
| Tr-3 | 0.79 | 0.72 | 0.07 | 1.1 |

*all data are expressed as percentage of dry weight. Tr-1, Tr-2, and Tr-3 are transgenic calli one, two and three
[1]non-delta-5 sterols
[2]delta-5 sterols These data show that transgenic cotton calli of the present invention overaccumulate squalene, total sterol and non-utilizable sterols relative to native, non-transgenic calli.

EXAMPLE 7

Transformation of Soybean

The HMGR 227-KYLX71 plasmid was mobilized into *Agrobacterim tumefaciens* strain 281. Strain 281 contains a fully armed T-DNA plasmid. Montoya et al., *J. Bacteriol.*, 129:101–107 (1977).

The resulting strain A281:227 is a binary plasmid strain. Upon transfection, transformed plant cells proliferate as an undifferentiated transgenic callus since the tumor inducing (Ti) genes are transferred with KYLX-227 as cointegrates. The advantage of this system is that no selection is needed for transformants because they are self-proliferating.

This is particularly advantageous in strains that have low transformation frequency and would not hold up well under stringent selection pressure. This expands the possible host range, including even woody strains, and existing vectors can be used without further engineering.

Sterilized cotyledons from soybean *Glycine max* cv Peking were inoculated with A281:227 by placing a small aliquot of the Agrobacterium culture in cuts made on the inner surface of the tissue. The infected cotyledons were then put on Gamborg's B5 media lacking hormones and cultured for two weeks. Gamborg et al., *Exp. Cell Res.*, 50:1151–1158 (1968). Transgenic calli were then isolated and analyzed for total squalene, total sterol and total cyclopropyl-pentacyclic (non-utilizable sterol levels as described in Example 3. The results of those studies are presented below in Table 8.

TABLE 8*

| Plant | Total Sterol | Cyclopropyl/ Pentacyclic Sterol | Squalene |
|---|---|---|---|
| Callus | | | |
| Control | 0.37 | 0.002 | 0.022 |
| Transgenic | 0.85 | 0.12 | 0.233 |

*Data are presented as a percentage of dry weight. Data for the control represent the average of five vector controls. Transgenic represents a single transformant designated D-13.

Pentacyclic triterpenoids are sterol compounds having a fifth ring formed from cyclization of the steroidal 17-position side chain. Examples of these compounds include alpha-amyrin, beta-amyrin and lupeol. Although these compounds are found in a wide variety of plants, they are usually present in only trace amounts. These compounds and their conjugates (e.g. saponins) are reported to have medicinal and insecticidal properties.

The positive identification of pentacyclic-type (non-utilizable) compounds in transgenic soybean callus was made by gas chromatography-mass spectroscopy (GC-MS). Quantification by GC analysis is difficult because these compounds coelute with cyclopropyl sterols. The results for soybean transformants given in Table 8, above, therefore give cyclopropyl and pentacyclic sterols as a combined quantity.

EXAMPLE 8

Transformation of Tomato

Hypocotyls from tomato *Lycopersicon esculentum* cv. UC82B were transformed as described in accordance with the procedures of Example 7 for soybean. After two weeks the transgenic calli were isolated and analyzed for sterol and squalene levels as described in Example 3.

The results of these studies are presented below in Table 9.

TABLE 9

| | Total Sterol | Cyclopropyl | Squalene |
|---|---|---|---|
| CTRL | 0.04 | <0.002 | 0.002 |
| TRNSG #10 | 1.42 | 0.84 | 0.142 |
| #19 | 0.56 | 0.21 | 0.039 |

*Data are expressed as percentage of dry weight CTRL = non-transgenic control TRNSG = transgenic The data show that calli of tomato plant cells transformed by a process of the present invention results in increases in total sterol, cyclopropyl (non-delta-5) sterols and squalene accumulation.

EXAMPLE 9

Transformation of Alfalfa

Hypocotyls from alfalfa strain RYSI were transformed in accordance with the procedures of Example 3 for tobacco. After three or four weeks transgenic calli were isolated and analyzed for sterol and squalene levels as described in Example 3. The results of those studies are shown below in Table 10.

TABLE 10*

| | Total Sterol | Cyclopropyl/ Pentacyclic Sterol | Squalene |
|---|---|---|---|
| CTRL | 0.24 | <0.002 | 0.002 |
| TRNSG | 1.26 | 0.99 | 0.052 |

*Data are expressed as percentage of dry weight CTRL = non-transgenic control TRNSG = transgenic The data from Table 10 show that transgenic alfalfa calli demonstrate large increases in total sterol, pentacyclic and cyclopropyl sterols, and squalene accumulation when compared to a native, non-transgenic calli.

EXAMPLE 10

Transgenic Tobacco Seeds

Transgenic tobacco seeds produced in accordance with the procedures of Example 1 were assayed for total sterol and squalene accumulation as described in Example 3. The results of those studies are presented below in Table 11.

TABLE 11*

| | Total Sterol | Cyclopropyl | Squalene |
|---|---|---|---|
| CTRL | 0.286 | 0.031 | 0.011 |
| TRNSG #5 | 0.509 | 0.123 | 0.047 |
| #19 | 0.714 | 0.163 | 0.042 |

*Data are expressed as percentage of dry weight CTRL = non-transgenic control TRNSG = transgenic The data in Table 11 show that transgenic tobacco seeds of the present invention have an increased accumulation of total sterol, cyclopropyl sterol (non-delta-5 sterol) and squalene when compared to a native, non-transgenic seed of the same strain.

The present invention has been described with respect to preferred embodiments. It is readily apparent to those skilled in the art that modifications and/or variations of the disclosed subject matter can be made without departing from the scope of the invention set forth herein.

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4768 base pairs
        ( B ) TYPE: nucleic acid
        ( C ) STRANDEDNESS: single
        ( D ) TOPOIDGY: linear ( i i ) MOLECULE TYPE: CDNA ( i x ) FEATURE:
        ( A ) NAME/KEY: CDS
        ( B ) LOCATION: 164..2827

( x i ) SEQUENCE DESCRIPTION: SEQ ID NO:1:

```
TGTATGTCTT GTCTTTCTCC TAAGGGGCGT AGGCTCATTG ATAACTCATG TCCTCACCTT          60

GCACTCCTTT TGGAATTATT TGGTTTGAGT GAAGAAGACC GGACCTTCGA GGTTCGCAAC         120

TTAAACAATA GACTTGTGAG GATCCAGGGA CCGAGTGGCT ACA ATG TTG TCA CGA          175
                                              Met Leu Ser Arg
                                                1

CTT TTC CGT ATG CAT GGC CTC TTT GTG GCC TCC CAT CCC TGG GAA GTT          223
Leu Phe Arg Met His Gly Leu Phe Val Ala Ser His Pro Trp Glu Val
 5               10                  15                  20

ATT GTG GGG ACG GTG ACA CTT ACC ATC TGT ATG ATG TCC ATG AAC ATG          271
Ile Val Gly Thr Val Thr Leu Thr Ile Cys Met Met Ser Met Asn Met
                 25                  30                  35

TTC ACT GGC AAC AAC AAG ATC TGT GGT TGG AAT TAC GAG TGC CCA AAA          319
Phe Thr Gly Asn Asn Lys Ile Cys Gly Trp Asn Tyr Glu Cys Pro Lys
             40                  45                  50

TTT GAG GAG GAT GTA TTG AGC AGT GAC ATC ATC ATC CTC ACC ATA ACA          367
Phe Glu Glu Asp Val Leu Ser Ser Asp Ile Ile Ile Leu Thr Ile Thr
         55                  60                  65

CGG TGC ATC GCC ATC CTG TAC ATT TAC TTC CAG TTC CAG AAC TTA CGT          415
Arg Cys Ile Ala Ile Leu Tyr Ile Tyr Phe Gln Phe Gln Asn Leu Arg
     70                  75                  80

CAG CTT GGG TCG AAG TAT ATT TTA GGT ATT GCT GGC CTG TTC ACA ATT          463
Gln Leu Gly Ser Lys Tyr Ile Leu Gly Ile Ala Gly Leu Phe Thr Ile
 85                  90                  95                 100

TTC TCA AGT TTT GTC TTT AGT ACA GTC GTC ATT CAC TTC TTA GAC AAA          511
Phe Ser Ser Phe Val Phe Ser Thr Val Val Ile His Phe Leu Asp Lys
                105                 110                 115

GAA CTG ACG GGC TTA AAT GAA GCT TTG CCC TTT TTC CTG CTT TTG ATT          559
Glu Leu Thr Gly Leu Asn Glu Ala Leu Pro Phe Phe Leu Leu Leu Ile
            120                 125                 130

GAC CTT TCT AGA GCG AGT GCA CTA GCA AAG TTT GCC CTA AGT TCA AAC          607
Asp Leu Ser Arg Ala Ser Ala Leu Ala Lys Phe Ala Leu Ser Ser Asn
        135                 140                 145

TCT CAG GAT GAA GTA AGG GAA AAT ATA GCT CGC GGA ATG GCA ATT CTG          655
Ser Gln Asp Glu Val Arg Glu Asn Ile Ala Arg Gly Met Ala Ile Leu
    150                 155                 160

GGC CCC ACA TTC ACC CTT GAT GCT CTT GTG GAA TGT CTT GTA ATT GGA          703
Gly Pro Thr Phe Thr Leu Asp Ala Leu Val Glu Cys Leu Val Ile Gly
165                 170                 175                 180

GTT GGC ACC ATG TCA GGG GTG CGT CAG CTT GAA ATC ATG TGC TGC TTT          751
Val Gly Thr Met Ser Gly Val Arg Gln Leu Glu Ile Met Cys Cys Phe
                185                 190                 195

GGC TGC ATG TCT GTG CTT GCC AAC TAC TTC GTG TTC ATG ACA TTT TTC          799
Gly Cys Met Ser Val Leu Ala Asn Tyr Phe Val Phe Met Thr Phe Phe
            200                 205                 210

CCA GCG TGT GTG TCC CTG GTC CTT GAG CTT TCT CGG GAA AGT CGA GAG          847
Pro Ala Cys Val Ser Leu Val Leu Glu Leu Ser Arg Glu Ser Arg Glu
        215                 220                 225
```

| | | | | | | | | | | | | | | | | |
|---|---|---|---|---|---|---|---|---|---|---|---|---|---|---|---|---|
| GGT | CGT | CCA | ATT | TGG | CAG | CTT | AGC | CAT | TTT | GCC | CGA | GTT | TTG | GAA | GAA | 895 |
| Gly | Arg | Pro | Ile | Trp | Gln | Leu | Ser | His | Phe | Ala | Arg | Val | Leu | Glu | Glu | |
| | 230 | | | | 235 | | | | | 240 | | | | | | |
| GAA | GAG | AAT | AAA | CCA | AAC | CCT | GTA | ACC | CAA | AGG | GTC | AAG | ATG | ATT | ATG | 943 |
| Glu | Glu | Asn | Lys | Pro | Asn | Pro | Val | Thr | Gln | Arg | Val | Lys | Met | Ile | Met | |
| 245 | | | | 250 | | | | | 255 | | | | | | 260 | |
| TCT | TTA | GGT | TTG | GTT | CTT | GTT | CAT | GCT | CAC | AGT | CGA | TGG | ATA | GCT | GAT | 991 |
| Ser | Leu | Gly | Leu | Val | Leu | Val | His | Ala | His | Ser | Arg | Trp | Ile | Ala | Asp | |
| | | | | 265 | | | | | 270 | | | | | 275 | | |
| CCT | TCC | CCT | CAG | AAT | AGC | ACA | ACA | GAA | CAT | TCT | AAA | GTC | TCC | TTG | GGA | 1039 |
| Pro | Ser | Pro | Gln | Asn | Ser | Thr | Thr | Glu | His | Ser | Lys | Val | Ser | Leu | Gly | |
| | | | 280 | | | | | 285 | | | | | 290 | | | |
| CTG | GAT | GAA | GAT | GTG | TCC | AAG | AGA | ATT | GAA | CCA | AGT | GTT | TCT | CTC | TGG | 1087 |
| Leu | Asp | Glu | Asp | Val | Ser | Lys | Arg | Ile | Glu | Pro | Ser | Val | Ser | Leu | Trp | |
| | | 295 | | | | | 300 | | | | | 305 | | | | |
| CAG | TTT | TAT | CTC | TCC | AAG | ATG | ATC | AGC | ATG | GAC | ATT | GAA | CAA | GTG | GTT | 1135 |
| Gln | Phe | Tyr | Leu | Ser | Lys | Met | Ile | Ser | Met | Asp | Ile | Glu | Gln | Val | Val | |
| 310 | | | | | 315 | | | | | 320 | | | | | | |
| ACC | CTG | AGC | TTA | GCT | TTT | CTG | TTG | GCT | GTC | AAG | TAC | ATT | TTC | TTT | GAA | 1183 |
| Thr | Leu | Ser | Leu | Ala | Phe | Leu | Leu | Ala | Val | Lys | Tyr | Ile | Phe | Phe | Glu | |
| 325 | | | | 330 | | | | | 335 | | | | | 340 | | |
| CAA | GCA | GAG | ACA | GAG | TCC | ACA | CTG | TCT | TTA | AAA | AAT | CCT | ATC | ACG | TCT | 1231 |
| Gln | Ala | Glu | Thr | Glu | Ser | Thr | Leu | Ser | Leu | Lys | Asn | Pro | Ile | Thr | Ser | |
| | | | | 345 | | | | 350 | | | | | 355 | | | |
| CCT | GTC | GTG | ACC | CCA | AAG | AAA | GCT | CCA | GAC | AAC | TGT | TGT | AGA | CGG | GAG | 1279 |
| Pro | Val | Val | Thr | Pro | Lys | Lys | Ala | Pro | Asp | Asn | Cys | Cys | Arg | Arg | Glu | |
| | | | 360 | | | | | 365 | | | | | 370 | | | |
| CCT | CTG | CTT | GTG | AGA | AGG | AGC | GAG | AAG | CTT | TCA | TCG | GTT | GAG | GAG | GAG | 1327 |
| Pro | Leu | Leu | Val | Arg | Arg | Ser | Glu | Lys | Leu | Ser | Ser | Val | Glu | Glu | Glu | |
| | | 375 | | | | | 380 | | | | | 385 | | | | |
| CCT | GGG | GTG | AGC | CAA | GAT | AGA | AAA | GTT | GAG | GTT | ATA | AAA | CCA | TTA | GTG | 1375 |
| Pro | Gly | Val | Ser | Gln | Asp | Arg | Lys | Val | Glu | Val | Ile | Lys | Pro | Leu | Val | |
| | 390 | | | | 395 | | | | | 400 | | | | | | |
| GTG | GAA | ACT | GAG | AGT | GCA | AGC | AGA | GCT | ACA | TTT | GTG | CTT | GGC | GCC | TCT | 1423 |
| Val | Glu | Thr | Glu | Ser | Ala | Ser | Arg | Ala | Thr | Phe | Val | Leu | Gly | Ala | Ser | |
| 405 | | | | 410 | | | | | 415 | | | | | 420 | | |
| GGG | ACC | AGC | CCT | CCA | GTG | GCA | GCG | AGG | ACA | CAG | GAG | CTT | GAA | ATT | GAA | 1471 |
| Gly | Thr | Ser | Pro | Pro | Val | Ala | Ala | Arg | Thr | Gln | Glu | Leu | Glu | Ile | Glu | |
| | | | | 425 | | | | 430 | | | | | 435 | | | |
| CTC | CCC | AGT | GAG | CCT | CGG | CCT | AAT | GAA | GAA | TGT | CTG | CAG | ATA | CTG | GAG | 1519 |
| Leu | Pro | Ser | Glu | Pro | Arg | Pro | Asn | Glu | Glu | Cys | Leu | Gln | Ile | Leu | Glu | |
| | | | 440 | | | | | 445 | | | | 450 | | | | |
| AGT | GCC | GAG | AAA | GGT | GCA | AAG | TTC | CTT | AGC | GAT | GCA | GAG | ATC | ATC | CAG | 1567 |
| Ser | Ala | Glu | Lys | Gly | Ala | Lys | Phe | Leu | Ser | Asp | Ala | Glu | Ile | Ile | Gln | |
| | | 455 | | | | | 460 | | | | | 465 | | | | |
| TTG | GTC | AAT | GCC | AAG | CAC | ATC | CCA | GCC | TAC | AAA | TTG | GAA | ACC | TTA | ATG | 1615 |
| Leu | Val | Asn | Ala | Lys | His | Ile | Pro | Ala | Tyr | Lys | Leu | Glu | Thr | Leu | Met | |
| | 470 | | | | 475 | | | | | 480 | | | | | | |
| GAA | ACT | CAT | GAA | CGT | GGT | GTA | TCT | ATT | CGC | CGG | CAG | CTC | CTC | TCC | ACA | 1663 |
| Glu | Thr | His | Glu | Arg | Gly | Val | Ser | Ile | Arg | Arg | Gln | Leu | Leu | Ser | Thr | |
| 485 | | | | | 490 | | | | 495 | | | | | 500 | | |
| AAG | CTT | CCA | GAG | CCT | TCT | TCT | CTG | CAG | TAC | CTG | CCT | TAC | AGA | GAT | TAT | 1711 |
| Lys | Leu | Pro | Glu | Pro | Ser | Ser | Leu | Gln | Tyr | Leu | Pro | Tyr | Arg | Asp | Tyr | |
| | | | | 505 | | | | 510 | | | | | 515 | | | |
| AAT | TAT | TCC | CTG | GTG | ATG | GGA | GCT | TGT | TGT | GAG | AAT | GTG | ATC | GGA | TAT | 1759 |
| Asn | Tyr | Ser | Leu | Val | Met | Gly | Ala | Cys | Cys | Glu | Asn | Val | Ile | Gly | Tyr | |
| | | | 520 | | | | | 525 | | | | | 530 | | | |
| ATG | CCC | ATC | CCT | GTC | GGA | GTA | GCA | GGG | CCT | CTG | TGC | CTG | GAT | GGT | AAA | 1807 |
| Met | Pro | Ile | Pro | Val | Gly | Val | Ala | Gly | Pro | Leu | Cys | Leu | Asp | Gly | Lys | |
| | | 535 | | | | | 540 | | | | | 545 | | | | |

| | | | | | | | | | | | | | | | | |
|---|---|---|---|---|---|---|---|---|---|---|---|---|---|---|---|---|
| GAG | TAC | CAG | GTT | CCA | ATG | GCA | ACA | ACG | GAA | GGC | TGT | CTG | GTG | GCC | AGC | 1855 |
| Glu | Tyr | Gln | Val | Pro | Met | Ala | Thr | Thr | Glu | Gly | Cys | Leu | Val | Ala | Ser | |
| 550 | | | | | 555 | | | | | 560 | | | | | | |

| | | | | | | | | | | | | | | | | |
|---|---|---|---|---|---|---|---|---|---|---|---|---|---|---|---|---|
| ACC | AAC | AGA | GGC | TGC | AGG | GCA | ATA | GGT | CTT | GGT | GGA | GGT | GCC | AGC | AGC | 1903 |
| Thr | Asn | Arg | Gly | Cys | Arg | Ala | Ile | Gly | Leu | Gly | Gly | Gly | Ala | Ser | Ser | |
| 565 | | | | | 570 | | | | | 575 | | | | | 580 | |

| | | | | | | | | | | | | | | | | |
|---|---|---|---|---|---|---|---|---|---|---|---|---|---|---|---|---|
| CGG | GTC | CTT | GCA | GAT | GGG | ATG | ACC | CGG | GGC | CCA | GTG | GTG | CGT | CTT | CCT | 1951 |
| Arg | Val | Leu | Ala | Asp | Gly | Met | Thr | Arg | Gly | Pro | Val | Val | Arg | Leu | Pro | |
| | | | | 585 | | | | | 590 | | | | | 595 | | |

| | | | | | | | | | | | | | | | | |
|---|---|---|---|---|---|---|---|---|---|---|---|---|---|---|---|---|
| CGT | GCT | TGT | GAT | TCT | GCA | GAA | GTG | AAG | GCC | TGG | CTT | GAA | ACA | CCC | GAA | 1999 |
| Arg | Ala | Cys | Asp | Ser | Ala | Glu | Val | Lys | Ala | Trp | Leu | Glu | Thr | Pro | Glu | |
| | | | 600 | | | | | 605 | | | | | 610 | | | |

| | | | | | | | | | | | | | | | | |
|---|---|---|---|---|---|---|---|---|---|---|---|---|---|---|---|---|
| GGG | TTT | GCG | GTG | ATA | AAG | GAC | GCC | TTC | GAT | AGC | ACT | AGC | AGA | TTT | GCA | 2047 |
| Gly | Phe | Ala | Val | Ile | Lys | Asp | Ala | Phe | Asp | Ser | Thr | Ser | Arg | Phe | Ala | |
| | | 615 | | | | | 620 | | | | | 625 | | | | |

| | | | | | | | | | | | | | | | | |
|---|---|---|---|---|---|---|---|---|---|---|---|---|---|---|---|---|
| CGT | CTA | CAG | AAG | CTT | CAT | GTG | ACC | ATG | GCA | GGG | CGC | AAC | CTG | TAC | ATC | 2095 |
| Arg | Leu | Gln | Lys | Leu | His | Val | Thr | Met | Ala | Gly | Arg | Asn | Leu | Tyr | Ile | |
| | 630 | | | | | 635 | | | | | 640 | | | | | |

| | | | | | | | | | | | | | | | | |
|---|---|---|---|---|---|---|---|---|---|---|---|---|---|---|---|---|
| CGT | TTC | CAG | TCC | AAG | ACA | GGG | GAT | GCC | ATG | GGG | ATG | AAC | ATG | ATT | TCC | 2143 |
| Arg | Phe | Gln | Ser | Lys | Thr | Gly | Asp | Ala | Met | Gly | Met | Asn | Met | Ile | Ser | |
| 645 | | | | | 650 | | | | | 655 | | | | | 660 | |

| | | | | | | | | | | | | | | | | |
|---|---|---|---|---|---|---|---|---|---|---|---|---|---|---|---|---|
| AAG | GGC | ACT | GAG | AAA | GCA | CTT | CTG | AAG | CTT | CAG | GAG | TTC | TTT | CCT | GAA | 2191 |
| Lys | Gly | Thr | Glu | Lys | Ala | Leu | Leu | Lys | Leu | Gln | Glu | Phe | Phe | Pro | Glu | |
| | | | | 665 | | | | | 670 | | | | | 675 | | |

| | | | | | | | | | | | | | | | | |
|---|---|---|---|---|---|---|---|---|---|---|---|---|---|---|---|---|
| ATG | CAG | ATT | CTG | GCA | GTT | AGT | GGT | AAC | TAC | TGC | ACT | GAC | AAG | AAA | CCT | 2239 |
| Met | Gln | Ile | Leu | Ala | Val | Ser | Gly | Asn | Tyr | Cys | Thr | Asp | Lys | Lys | Pro | |
| | | | 680 | | | | | 685 | | | | | 690 | | | |

| | | | | | | | | | | | | | | | | |
|---|---|---|---|---|---|---|---|---|---|---|---|---|---|---|---|---|
| GCC | GCC | ATA | AAC | TGG | ATC | GAG | GGA | AGA | GGA | AAG | ACA | GTT | GTG | TGT | GAA | 2287 |
| Ala | Ala | Ile | Asn | Trp | Ile | Glu | Gly | Arg | Gly | Lys | Thr | Val | Val | Cys | Glu | |
| | | 695 | | | | | 700 | | | | | 705 | | | | |

| | | | | | | | | | | | | | | | | |
|---|---|---|---|---|---|---|---|---|---|---|---|---|---|---|---|---|
| GCT | GTT | ATT | CCA | GCC | AAG | GTG | GTG | AGA | GAA | GTA | TTA | AAG | ACA | ACT | ACG | 2335 |
| Ala | Val | Ile | Pro | Ala | Lys | Val | Val | Arg | Glu | Val | Leu | Lys | Thr | Thr | Thr | |
| | 710 | | | | | 715 | | | | | 720 | | | | | |

| | | | | | | | | | | | | | | | | |
|---|---|---|---|---|---|---|---|---|---|---|---|---|---|---|---|---|
| GAA | GCT | ATG | ATT | GAC | GTA | AAC | ATT | AAC | AAG | AAT | CTT | GTG | GGT | TCT | GCC | 2383 |
| Glu | Ala | Met | Ile | Asp | Val | Asn | Ile | Asn | Lys | Asn | Leu | Val | Gly | Ser | Ala | |
| 725 | | | | | 730 | | | | | 735 | | | | | 740 | |

| | | | | | | | | | | | | | | | | |
|---|---|---|---|---|---|---|---|---|---|---|---|---|---|---|---|---|
| ATG | GCT | GGG | AGC | ATA | GGA | GGC | TAC | AAT | GCC | CAT | GCA | GCA | AAC | ATC | GTC | 2431 |
| Met | Ala | Gly | Ser | Ile | Gly | Gly | Tyr | Asn | Ala | His | Ala | Ala | Asn | Ile | Val | |
| | | | | 745 | | | | | 750 | | | | | 755 | | |

| | | | | | | | | | | | | | | | | |
|---|---|---|---|---|---|---|---|---|---|---|---|---|---|---|---|---|
| ACT | GCT | ATC | TAC | ATT | GcA | TGT | GGC | CAG | GAT | GCA | GCA | CAG | AAT | GTG | GGG | 2479 |
| Thr | Ala | Ile | Tyr | Ile | Ala | Cys | Gly | Gln | Asp | Ala | Ala | Gln | Asn | Val | Gly | |
| | | | 760 | | | | | 765 | | | | | 770 | | | |

| | | | | | | | | | | | | | | | | |
|---|---|---|---|---|---|---|---|---|---|---|---|---|---|---|---|---|
| AGT | TCA | AAC | TGT | ATT | ACT | TTA | ATG | GAA | GCA | AGT | GGT | CCC | ACG | AAT | GAA | 2527 |
| Ser | Ser | Asn | Cys | Ile | Thr | Leu | Met | Glu | Ala | Ser | Gly | Pro | Thr | Asn | Glu | |
| | | 775 | | | | | 780 | | | | | 785 | | | | |

| | | | | | | | | | | | | | | | | |
|---|---|---|---|---|---|---|---|---|---|---|---|---|---|---|---|---|
| GAC | TTG | TAT | ATC | AGC | TGC | ACC | ATG | CCA | TCT | ATA | GAG | ATA | GGA | ACT | GTG | 2575 |
| Asp | Leu | Tyr | Ile | Ser | Cys | Thr | Met | Pro | Ser | Ile | Glu | Ile | Gly | Thr | Val | |
| | 790 | | | | | 795 | | | | | 800 | | | | | |

| | | | | | | | | | | | | | | | | |
|---|---|---|---|---|---|---|---|---|---|---|---|---|---|---|---|---|
| GGT | GGT | GGG | ACC | AAC | CTC | CTA | CCA | CAG | CAG | GCC | TGT | CTG | CAG | ATG | CTA | 2623 |
| Gly | Gly | Gly | Thr | Asn | Leu | Leu | Pro | Gln | Gln | Ala | Cys | Leu | Gln | Met | Leu | |
| 805 | | | | | 810 | | | | | 815 | | | | | 820 | |

| | | | | | | | | | | | | | | | | |
|---|---|---|---|---|---|---|---|---|---|---|---|---|---|---|---|---|
| GGT | GTT | CAA | GGA | GCG | TGC | AAA | GAC | AAT | CCT | GGA | GAA | AAT | GCA | CGG | CAA | 2671 |
| Gly | Val | Gln | Gly | Ala | Cys | Lys | Asp | Asn | Pro | Gly | Glu | Asn | Ala | Arg | Gln | |
| | | | | 825 | | | | | 830 | | | | | 835 | | |

| | | | | | | | | | | | | | | | | |
|---|---|---|---|---|---|---|---|---|---|---|---|---|---|---|---|---|
| CTT | GCC | CGA | ATT | GTG | TGT | GGT | ACT | GTA | ATG | GCT | GGG | GAG | TTG | TCC | TTG | 2719 |
| Leu | Ala | Arg | Ile | Val | Cys | Gly | Thr | Val | Met | Ala | Gly | Glu | Leu | Ser | Leu | |
| | | | 840 | | | | | 845 | | | | | 850 | | | |

| | | | | | | | | | | | | | | | | |
|---|---|---|---|---|---|---|---|---|---|---|---|---|---|---|---|---|
| ATG | GCA | GCA | TTG | GCA | GCA | GGA | CAT | CTT | GTT | AGA | AGT | CAC | ATG | GTT | CAT | 2767 |
| Met | Ala | Ala | Leu | Ala | Ala | Gly | His | Leu | Val | Arg | Ser | His | Met | Val | His | |
| | | 855 | | | | | 860 | | | | | 865 | | | | |

| | | | | | | | | | | | | | | | |
|---|---|---|---|---|---|---|---|---|---|---|---|---|---|---|---|
| AAC | AGA | TCG | AAG | ATA | AAT | TTA | CAA | GAT | CTG | CAA | GGA | ACG | TGC | ACC | AAG | 2815 |
| Asn | Arg | Ser | Lys | Ile | Asn | Leu | Gln | Asp | Leu | Gln | Gly | Thr | Cys | Thr | Lys |
| | 870 | | | | | 875 | | | | | 880 | | | | |

| | | | | |
|---|---|---|---|---|
| AAG | TCA | GCT | TGAGCAGCCT | GACAGTATTG AACTGAAACA CGGGCATTGG | 2864 |
| Lys | Ser | Ala |
| 885 |

```
GTTCTCAAGG  ACTAACATGA  AATCTGTGAA  TTAAAATCT   CAATGCAGTG  TCTTGTGGAA  2924
GATGAATGAA  CGTGATCAGT  GAGACGCCTG  CTTGGTTTCT  GGCTCTTTCA  GAGACGTCTG  2984
AGGTCCTTTG  CTCGGAGACT  CCTCAGATCT  GGAAACAGTG  TGGTCCTTCC  CATGCTGTAT  3044
TCTGAAAAGA  TCTCATATGG  ATGTTGTGCT  CTGAGCACCA  CAGATGTGAT  CTGCAGCTCG  3104
TTTCTGAAAT  GATGGAGTTC  ATGGTGATCA  GTGTGAGACT  GCCTCTCCC   AGCAGGTTAA  3164
AAATGGAGTT  TTAAATTATA  CTGTAGCTGA  CAGTACTTCT  GATTTATAT   TTATTTAGTC  3224
TGAGTTGTAG  AACTTTGCAA  TCTAAGTTTA  TTTTTGTAA   CCTAATAATT  CATTTGGTGC  3284
TGGTCTATTG  ATTTTTGGGG  GTAAACAATA  TTATTCTTCA  GAAGGGGACC  TACTTCTTCA  3344
TGGGAAGAAT  TACTTTTATT  CTCAAACTAC  AGAACAATGT  GCTAAGCAGT  GCTAAATTGT  3404
TCTCATGAAG  AAAACAGTCA  CTGCATTTAT  CTCTGTAGGC  CTTTTTCAG   AGAGGCTTG   3464
TCTAGATTTT  TGCCAGCTAG  GCTACTGCAT  GTCTTAGTGT  CAGGCCTTAG  GAAAGTGCCA  3524
CGCTCTGCAC  TAAAGATATC  AGAGCTCTTG  GTGTTACTTA  GACAAGAGTA  TGAGCAAGTC  3584
GGACCTCTCA  GAGTGTGGGA  ACACAGTTTT  GAAAGAAAAA  CCATTTCTCT  AAGCCAATTT  3644
TCTTTAAAGA  CATTTTAACT  TATTTAGCTG  AGTTCTAGAT  TTTTCGGGTA  AACTATCAAA  3704
TCTGTATATG  TTGTAATAAA  GTGTCTTATG  CTAGGAGTTT  ATTCAAAGTG  TTTAAGTAAT  3764
AAAAGGACTC  AAATTTACAC  TGATAAAATA  CTCTAGCTTG  GGCCAGAGAA  GACAGTGCTC  3824
ATTAGCGTTG  TCCAGGAAAC  CCTGCTTGCT  TGCCAAGCCT  AATGAAGGGA  AAGTCAGCTT  3884
TCAGAGCCAA  TGATGGAGGC  CACATGAATG  GCCCTGGAGC  TGTGTGCCTT  GTTCTGTGGC  3944
CAGGAGCTTG  GTGACTGAAT  CATTTACGGG  CTCCTTTGAT  GGACCCATAA  AAGCTCTTAG  4004
CTTCCTCAGG  GGGTCAGCAG  AGTTGTTGAA  TCTTAATTTT  TTTTTAATG   TACCAGTTTT  4064
GTATAAATAA  TAATAAAGAG  CTCCTTATTT  TGTATTCTAT  CTAATGCTTC  GAGTTCAGTC  4124
TTGGGAAGCT  GACATCTCAT  GTAGAAGATG  GACTCTGAAA  GACATTCCAA  GAGTGCAGCG  4184
GCATCATGGG  AGCCTCTTAG  TGATTGTGTG  TCAGTATTAT  TGTGGAAGAT  TGACTTTGCT  4244
TTTGTATGTG  AAGTTTCAGA  TTGCTCCTCT  TGTGACTTTT  TAGCCAGTAA  CATTTTATTT  4304
ACCTGAGCTT  GTCATGGAAG  TGGCAGTGAA  AAGTATTGAG  TATTCATGCT  GGTGACTGTA  4364
ACCAATGTCA  TCTTGCTAAA  AACTCATGTT  TTGTACAATT  ACTAAATTGT  ATACATTTTG  4424
TTATAGAATA  CTTTTTCCAG  TTGAGTAAAT  TATGAAAGGA  AGTTAACATT  AACAGGTGTA  4484
AGCGGTGGCT  TTTTTAAAAT  GAAGGATTAA  CCCTAAGCCC  GAGACCCAGA  AGCTAGCAAA  4544
GTCTGGCAGA  GTGGTAAACT  GTCCTGCTGG  GGCCATCCAA  TCATCTCTCT  CCATTACACT  4604
TTCTAACTTT  GCAGCATTGG  TGCTGGCCAG  TGTATTGTTT  CATTGATCTT  CCTTACGCTT  4664
AGAGGGTTTG  ATTGGTTCAG  ATCTATAATC  TCAGCCACAT  TGTCTTGGTA  TCAGCTGGAG  4724
AGAGTTAAGA  GGA-AGGGAAA ATAAAGTTCA GATAGCCAAA ACAC                     4768
```

( 2 ) INFORMATION FOR SEQ ID NO:2:

( i ) SEQUENCE CHARACTERISTICS:
        ( A ) LENGTH: 887 amino acids
        ( B ) TYPE: amino acid
        ( D ) TOPOL40GY: linear ( i i ) MOLECULE TYPE: protein ( x i ) SEQUENCE DESCRIPTION: SEQ ID NO:2:

Met Leu Ser Arg Leu Phe Arg Met His Gly Leu Ile Val Ala Ser His
1               5                  10                 15

Pro Trp Glu Val Ile Val Gly Thr Val Thr Leu Thr Ile Cys Met Met
                    20                 25                 30

Ser Met Asn Met Phe Thr Gly Asn Asn Lys Ile Cys Gly Trp Asn Tyr
            35                 40                 45

Glu Cys Pro Lys Phe Glu Glu Asp Val Leu Ser Ser Asp Ile Ile Ile
        50                 55                 60

Leu Thr Ile Thr Arg Cys Ile Ala Ile Leu Tyr Ile Tyr Phe Gln Phe
65                  70                 75                 80

Gln Asn Leu Arg Gln Leu Gly Ser Lys Tyr Ile Leu Gly Ile Ala Gly
                                85                 90                 95

Leu Phe Thr Ile Phe Ser Ser Phe Val Phe Ser Thr Val Val Ile His
                            100                105                110

Phe Leu Asp Lys Glu Leu Thr Gly Leu Asn Glu Ala Leu Pro Phe Phe
                        115                120                125

Leu Leu Leu Ile Asp Leu Ser Arg Ala Ser Ala Leu Ala Lys Phe Ala
                    130                135                140

Leu Ser Ser Asn Ser Gln Asp Glu Val Arg Glu Asn Ile Ala Arg Gly
145                150                155                160

Met Ala Ile Leu Gly Pro Thr Phe Thr Leu Asp Ala Leu Val Glu Cys
                                165                170                175

Leu Val Ile Gly Val Gly Thr Met Ser Gly Val Arg Gln Leu Glu Ile
                            180                185                190

Met Cys Cys Phe Gly Cys Met Ser Val Leu Ala Asn Tyr Phe Val Phe
                        195                200                205

Met Thr Phe Phe Pro Ala Cys Val Ser Leu Val Leu Glu Leu Ser Arg
                    210                215                220

Glu Ser Arg Glu Gly Arg Pro Ile Trp Gln Leu Ser His Phe Ala Arg
225                230                235                240

Val Leu Glu Glu Glu Glu Asn Lys Pro Asn Pro Val Thr Gln Arg Val
                                245                250                255

Lys Met Ile Met Ser Leu Gly Leu Val Leu Val His Ala His Ser Arg
                            260                265                270

Trp Ile Ala Asp Pro Ser Pro Gln Asn Ser Thr Thr Glu His Ser Lysg
                        275                280                285

Val Ser Leu Gly Losu Asp Glu Asp Val Ser Lys Arg Ile Glu Pro Serg
                    290                295                300

Val Ser Leu Trp Gln Phe Tyr Leu Ser Lys Met Ile Ser Met Asp Ile
305                310                315                320

Glu Gln Val Val Thr Leu Ser Leu Ala Phe Leu Leu Ala Val Lys Tyr
                                325                330                335

Ile Phe Phe Glu Gln Ala Glu Thr Glu Ser Thr Leu Ser Leu Lys Asn
                            340                345                350

Pro Ile Thr Ser Pro Val Val Thr Pro Lys Lys Ala Pro Asp Asn Cys
                        355                360                365

Cys Arg Arg Glu Pro Leu Leu Val Arg Arg Ser Glu Lys Leu Ser Ser
                    370                375                380

Val Glu Glu Glu Pro Gly Val Ser Gln Asp Arg Lys Val Glu Val Ile
385                390                395                400

Lys Pro Leu Val Val Glu Thr Glu Ser Ala Ser Arg Ala Thr Phe Val

```
                    405 410 415

Leu Gly Ala Ser Gly Thr Ser Pro Pro Val Ala Ala Arg Thr Gln Glu
                    420 425 430

Leu Glu Ile Glu Leu Pro Ser Glu Pro Arg Pro Asn Glu Glu Cys Leu
                    435 440 445

Gln Ile Leu Glu Ser Ala Glu Lys Gly Ala Lys Phe Leu Ser Asp Ala
                    450 455 460

Glu Ile Ile Gln Leu Val Asn Ala Lys His Ile Pro Ala Tyr Lys Leu
465 470 475 480

Glu Thr Leu Met Glu Thr His Glu Arg Gly Val Ser Ile Arg Arg Gln
                    485 490 495

Leu Leu Ser Thr Lys Leu Pro Glu Pro Ser Ser Leu Gln Tyr Leu Pro
                    500 505 510

Tyr Arg Asp Tyr Asn Tyr Ser Leu Val Met Gly Ala Cys Cys Glu Asn
                    515 520 525

Val Ile Gly Tyr Met Pro Ile Pro Val Gly Val Ala Gly Pro Leu Cys
                    530 535 540

Leu Asp Gly Lys Glu Tyr Gln Val Pro Met Ala Thr Thr Glu Gly Cys
545 550 555 560

Leu Val Ala Ser Thr Asn Arg Gly Cys Arg Ala Ile Gly Leu Gly Gly
                    565 570 575

Gly Ala Ser Ser Arg Val Leu Ala Asp Gly Met Thr Arg Gly Pro Val
                    580 585 590

Val Arg Leu Pro Arg Ala Cys Asp Ser Ala Glu Val Lys Ala Trp Leu
                    595 600 605

Glu Thr Pro Glu Gly Phe Ala Val Ile Lys Asp Ala Phe Asp Ser Thr
                    610 615 620

Ser Arg Phe Ala Arg Leu Gln Lys Leu His Val Thr Met Ala Gly Arg
625 630 635 640

Asn Leu Tyr Ile Arg Phe Gln Ser Lys Thr Gly Asp Ala Met Gly Met
                    645 650 655

Asn Met Ile Ser Lys Gly Thr Glu Lys Ala Xeu Leu Lys Leu Gln Glu
                    660 665 670

Phe Phe Pro Glu Met Gln Ile Leu Ala Val Ser Gly Asn Tyr Cys Thr
                    675 680 685

Asp Lys Lys Pro Ala Ala Ile Asn Trp Ile Glu Gly Arg Gly Lys Thr
                    690 695 700

Val Val Cys Glu Ala Val Ile Pro Ala Lys Val Val Arg Glu Val Leu
705 710 715 720

Lys Thr Thr Thr Glu Ala Met Ile Asp Val Asn Ile Asn Lys Asn Leu
                    725 730 735

Val Gly Ser Ala Met Ala Gly Ser Ile Gly Gly Tyr Asn Ala His Ala
                    740 745 750

Ala Asn Ile Val Thr Ala Ile Tyr Ile Ala Cys Gly Gln Asp Ala Ala
                    755 760 765

Gln Asn Val Gly Ser Ser Asn Cys Ile Thr Leu Met Glu Ala Ser Gly
                    770 775 780

Pro Thr Asn Glu Asp Leu Tyr Ile Ser Cys Thr Met Pro Ser Ile Glu
785 790 795 800

Ile Gly Thr val Gly Gly Gly Thr Asn Leu Leu Pro Gln Gln Ala Cys
                    805 810 815

Leu Gln Met Leu Gly Val Gln Gly Ala Cys Lys Asp Asn Pro Gly Glu
                    820 825 830
```

```
Asn Ala Arg Gln Leu Ala Arg Ile Val Cys Gly Thr Val Met Ala Gly
           835                 840                 845

Glu Leu Ser Leu Met Ala Ala Leu Ala Ala Gly His Leu Val Arg Ser
      850                 855                 860

His Met Val His Asn Arg Ser Lys Ile Asn Leu Gln Asp Leu Gln Gly
865                 870                 875                 880

Thr Cys Thr Lys Lys Ser Ala
                        885
```

( 2 ) INFORMATION FOR SEQ ID NO:3:

( i ) SEQUENCE CHARACTERISTICS:
            ( A ) LENGTH: 3360 base pairs
            ( B ) TYPE: nucleic acid
            ( C ) STRANDEDNESS: single
            ( D ) TOPOLOGY: linear ( i i ) MOLECULE TYPE: DNA (genomic)

( i x ) FEATURE:
            ( A ) NAME/KEY: CDS
            ( B ) L40CATION: 121..3282

( x i ) SEQUENCE DESCRIPTION: SEQ ID NO:3:

```
TTTATTAACT TATTTTTTC TTCTTTCTAC CCAATTCTAG TCAGGAAAAG ACTAAGGGCT        60

GGAACATAGT GTATCATTGT CTAATTGTTG ATACAAAGTA GATAAATACA TAAAACAAGC       120

ATG CCG CCG CTA TTC AAG GGA CTG AAA CAG ATG GCA AAG CCA ATT GCC        168
Met Pro Pro Leu Phe Lys Gly Leu Lys Gln Met Ala Lys Pro Ile Ala
 1                5                  10                 15

TAT GTT TCA AGA TTT TCG GCG AAA CGA CCA ATT CAT ATA ATA CTT TTT        216
Tyr Val Ser Arg Phe Ser Ala Lys Arg Pro Ile His Ile Ile Leu Phe
               20                  25                 30

TCT CTA ATC ATA TCC GCA TTC GCT TAT CTA TCC GTC ATT CAG TAT TAC        264
Ser Leu Ile Ile Ser Ala Phe Ala Tyr Leu Ser Val Ile Gln Tyr Tyr
           35                  40                  45

TTC AAT GGT TGG CAA CTA CAT TCA AAT AGT GTT TTT GAA ACT GCT CCA        312
Phe Asn Gly Trp Gln Leu Asp Ser Asn Ser Val Phe Glu Thr Ala Pro
       50                  55                  60

AAT AAA GAC TCC AAC ACT CTA TTT CAA GAA TGT TCC CAT TAC TAC AGA        360
Asn Lys Asp Ser Asn Thr Leu Phe Gln Glu Cys Ser His Tyr Tyr Arg
 65                 70                  75                 80

GAT TCC TCT CTA GAT GGT TGG GTA TCA ATC ACC GCG CAT GAA GCT AGT        408
Asp Ser Ser Leu Asp Gly Trp Val Ser Ile Thr Ala His Glu Ala Ser
                85                  90                 95

GAG TTA CCA GCC CCA CAC CAT TAC TAT CTA TTA AAC CTG AAC TTC AAT        456
Glu Leu Pro Ala Pro His His Tyr Tyr Leu Leu Asn Leu Asn Phe Asn
           100                 105                110

AGT CCT AAT GAA ACT GAC TCC ATT CCA GAA CTA GCT AAC ACG GTT TTT        504
Ser Pro Asn Glu Thr Asp Ser Ile Pro Glu Leu Ala Asn Thr Val Phe
       115                 120                 125

GAG AAA GAT AAT ACA AAA TAT ATT CTG CAA GAA GAT CTC AGT GTT TCC        552
Glu Lys Asp Asn Thr Lys Tyr Ile Leu Gln Glu Asp Leu Ser Val Ser
   130                 135                 140

AAA GAA ATT TCT TCT ACT GAT GGA ACG AAA TGG AGG TTA AGA AGT GAC        600
Lys Glu Ile Ser Ser Thr Asp Gly Thr Lys Trp Arg Leu Arg Ser Asp
145                 150                 155                160

AGA AAA AGT CTT TTC GAC GTA AAG ACG TTA GCA TAT TCT CTC TAC GAT        648
Arg Lys Ser Leu Phe Asp Val Lys Thr Leu Ala Tyr Ser Leu Tyr Asp
               165                 170                175

GTA TTT TCA GAA AAT GTA ACC CAA GCA GAC CCG TTT GAC GTC CTT ATT        696
Val Phe Ser Glu Asn Val Thr Gln Ala Asp Pro Phe Asp Val Leu Ile
           180                 185                 190
```

| | | | | | | | | | | | | | | | | |
|---|---|---|---|---|---|---|---|---|---|---|---|---|---|---|---|---|
| ATG | GTT | ACT | GCC | TAC | CTA | ATG | ATG | TTC | TAC | ACC | ATA | TTC | GGC | CTC | TTC | 744 |
| Met | Val | Thr | Ala | Tyr | Leu | Met | Met | Phe | Tyr | Thr | Ile | Phe | Gly | Leu | Phe | |
| | | 195 | | | | 200 | | | | | 205 | | | | | |
| AAT | GAC | ATG | AGG | AAG | ACC | GGG | TCA | AAT | TTT | TGG | TTG | AGC | GCC | TCT | ACA | 792 |
| Asn | Asp | Met | Arg | Lys | Thr | Gly | Ser | Asn | Phe | Trp | Leu | Ser | Ala | Ser | Thr | |
| | 210 | | | | | 215 | | | | | 220 | | | | | |
| GTG | GTC | AAT | TCT | GCA | TCA | TCA | CTT | TTC | TTA | GCA | TTG | TAT | GTC | ACC | CAA | 840 |
| Val | Val | Asn | Ser | Ala | Ser | Ser | Leu | Phe | Leu | Ala | Leu | Tyr | Val | Thr | Gln | |
| 225 | | | | | 230 | | | | | 235 | | | | | 240 | |
| TGT | ATT | CTA | GGC | AAA | GAA | GTT | TCC | GCA | TTA | ACT | CTT | TTT | GAA | GGT | TTG | 888 |
| Cys | Ile | Leu | Gly | Lys | Glu | Val | Ser | Ala | Leu | Thr | Leu | Phe | Glu | Gly | Leu | |
| | | | | 245 | | | | | 250 | | | | | 255 | | |
| CCT | TTC | ATT | GTA | GTT | GTT | GTT | GGT | TTC | AAG | CAC | AAA | ATC | AAG | ATT | GCC | 936 |
| Pro | Phe | Ile | Val | Val | Val | Val | Gly | Phe | Lys | His | Lys | Ile | Lys | Ile | Ala | |
| | | | 260 | | | | | 265 | | | | | 270 | | | |
| CAG | TAT | GCC | CTG | GAG | AAA | TTT | GAA | AGA | GTC | GGT | TTA | TCT | AAA | AGG | ATT | 984 |
| Gln | Tyr | Ala | Xeu | Glu | Lys | Phe | Glu | Arg | Val | Gly | Leu | Ser | Lys | Arg | Ile | |
| | | 275 | | | | | 280 | | | | | 285 | | | | |
| ACT | ACC | GAT | GAA | ATC | GTT | TTT | GAA | TCC | GTG | AGC | GAA | GAG | GGT | GGT | CGT | 1032 |
| Thr | Thr | Asp | Glu | Ile | Val | Phe | Glu | Ser | Val | Ser | Glu | Glu | Gly | Gly | Arg | |
| | 290 | | | | | 295 | | | | | 300 | | | | | |
| TTG | ATT | CAA | GAC | CAT | TTG | CTT | TGT | ATT | TTT | GCC | TTT | ATC | GGA | TGC | TCT | 1080 |
| Leu | Ile | Gln | Asp | His | Leu | Leu | Cys | Ile | Phe | Ala | Phe | Ile | Gly | Cys | Ser | |
| 305 | | | | | 310 | | | | | 315 | | | | | 320 | |
| ATG | TAT | GCT | CAC | CAA | TTG | AAG | ACT | TTG | ACA | AAC | TTC | TGC | ATA | TTA | TCA | 1128 |
| Met | Tyr | Ala | His | Gln | Leu | Lys | Thr | Leu | Thr | Asn | Phe | Cys | Ile | Leu | Ser | |
| | | | | 325 | | | | | 330 | | | | | 335 | | |
| GCA | TTT | ATC | CTA | ATT | TTT | GAA | TTG | ATT | TTA | ACT | CCT | ACA | TTT | TAT | TCT | 1176 |
| Ala | Phe | Ile | Leu | Ile | Phe | Glu | Leu | Ile | Leu | Thr | Pro | Thr | Phe | Tyr | Ser | |
| | | | 340 | | | | | 345 | | | | | 350 | | | |
| GCT | ATC | TTA | GCG | CTT | AGA | CTG | GAA | ATG | AAT | GTT | ATC | CAC | AGA | TCT | ACT | 1224 |
| Ala | Ile | Leu | Ala | Leu | Arg | Leu | Glu | Met | Asn | Val | Ile | His | Arg | Ser | Thr | |
| | | 355 | | | | | 360 | | | | | 365 | | | | |
| ATT | ATC | AAG | CAA | ACA | TTA | GAA | GAA | GAC | GGT | GTT | GTT | CCA | TCT | ACA | GCA | 1272 |
| Ile | Ile | Lys | Gln | Thr | Leu | Glu | Glu | Asp | Gly | Val | Val | Pro | Ser | Thr | Ala | |
| | 370 | | | | | 375 | | | | | 380 | | | | | |
| AGA | ATC | ATT | TCT | AAA | GCA | GAA | AAG | AAA | TCC | GTA | TCT | TCT | TTC | TTA | AAT | 1320 |
| Arg | Ile | Ile | Ser | Lys | Ala | Glu | Lys | Lys | Ser | Val | Ser | Ser | Phe | Leu | Asn | |
| 385 | | | | | 390 | | | | | 395 | | | | | 400 | |
| CTC | AGT | GTG | GTT | GTC | ATT | ATC | ATG | AAA | CTC | TCT | GTC | ATA | CTG | TTG | TTT | 1368 |
| Leu | Ser | Val | Val | Val | Ile | Ile | Met | Lys | Leu | Ser | Val | Ile | Leu | Leu | Phe | |
| | | | | 405 | | | | | 410 | | | | | 415 | | |
| GTT | TTC | ATC | AAC | TTT | TAT | AAC | TTT | GGT | GCA | AAT | TGG | GTC | AAT | GAT | GCC | 1416 |
| Val | Phe | Ile | Asn | Phe | Tyr | Asn | Phe | Gly | Ala | Asn | Trp | Val | Asn | Asp | Ala | |
| | | | 420 | | | | | 425 | | | | | 430 | | | |
| TTC | AAT | TCA | TTG | TAC | TTC | GAT | AAG | GAA | CGT | GTT | TCT | CTA | CCA | GAT | TTT | 1464 |
| Phe | Asn | Ser | Leu | Tyr | Phe | Asp | Lys | Glu | Arg | Val | Ser | Leu | Pro | Asp | Phe | |
| | | 435 | | | | | 440 | | | | | 445 | | | | |
| ATT | ACC | TCG | AAT | GCC | TCT | GAA | AAC | TTT | AAA | GAG | CAA | GCT | ATT | GTT | AGT | 1512 |
| Ile | Thr | Ser | Asn | Ala | Ser | Glu | Asn | Phe | Lys | Glu | Gln | Ala | Ile | Val | Ser | |
| | 450 | | | | | 455 | | | | | 460 | | | | | |
| GTC | ACC | CCA | TTA | TTA | TAT | TAC | AAA | CCC | ATT | AAG | TCC | TAC | CAA | CGC | ATT | 1560 |
| Val | Thr | Pro | Leu | Leu | Tyr | Tyr | Lys | Pro | Ile | Lys | Ser | Tyr | Gln | Arg | Ile | |
| 465 | | | | | 470 | | | | | 475 | | | | | 480 | |
| GAG | GAT | ATG | GTT | CTT | CTA | TTG | CTT | CGT | AAT | GTC | AGT | GTT | GCC | ATT | CGT | 1608 |
| Glu | Asp | Met | Val | Leu | Leu | Leu | Leu | Arg | Asn | Val | Ser | Val | Ala | Ile | Arg | |
| | | | | 485 | | | | | 490 | | | | | 495 | | |
| GAT | AGG | TTC | GTC | AGT | AAA | TTA | GTT | CTT | TCC | GCC | TTA | GTA | TGC | AGT | GCT | 1656 |
| Asp | Arg | Phe | Val | Ser | Lys | Leu | Val | Leu | Ser | Ala | Leu | Val | Cys | Ser | Ala | |
| | | | 500 | | | | | 505 | | | | | 510 | | | |

| | | | | | | | | | | | | | | | | |
|---|---|---|---|---|---|---|---|---|---|---|---|---|---|---|---|---|
| GTC | ATC | AAT | GTG | TAT | TTA | TTG | AAT | GCT | GCT | AGA | ATT | CAT | ACC | AGT | TAT | 1704 |
| Val | Ile | Asn | Val | Tyr | Leu | Leu | Asn | Ala | Ala | Arg | Ile | His | Thr | Ser | Tyr | |
| 515 | | | | | 520 | | | | | | | 525 | | | | |
| ACT | GCA | GAC | CAA | TTG | GTG | AAA | ACT | GAA | GTC | ACC | AAG | AAG | TCT | TTT | ACT | 1752 |
| Thr | Ala | Asp | Gln | Leu | Val | Lys | Thr | Glu | Val | Thr | Lys | Lys | Ser | Phe | Thr | |
| 530 | | | | | 535 | | | | | 540 | | | | | | |
| GCT | CCT | GTA | CAA | AAG | GCT | TCT | ACA | CCA | GTT | TTA | ACC | AAT | AAA | ACA | GTC | 1800 |
| Ala | Pro | Val | Gln | Lys | Ala | Ser | Thr | Pro | Val | Leu | Thr | Asn | Lys | Thr | Val | |
| 545 | | | | | 550 | | | | | 555 | | | | | 560 | |
| ATT | TCT | GGA | TCG | AAA | GTC | AAA | AGT | TTA | TCA | TCT | GCG | CAA | TCG | AGC | TCA | 1848 |
| Ile | Ser | Gly | Ser | Lys | Val | Lys | Ser | Leu | Ser | Ser | Ala | Gln | Ser | Ser | Ser | |
| | | | | 565 | | | | | 570 | | | | | 575 | | |
| TCA | GGA | CCT | TCA | TCA | TCT | AGT | GAG | GAA | GAT | GAT | TCC | CGC | GAT | ATT | GAA | 1896 |
| Ser | Gly | Pro | Ser | Ser | Ser | Ser | Glu | Glu | Asp | Asp | Ser | Arg | Asp | Ile | Glu | |
| | | | 580 | | | | | 585 | | | | | 590 | | | |
| AGC | TTG | GAT | AAG | AAA | ATA | CGT | CCT | TTA | GAA | GAA | TTA | GAA | GCA | TTA | TTA | 1944 |
| Ser | Leu | Asp | Lys | Lys | Ile | Arg | Pro | Leu | Glu | Glu | Leu | Glu | Ala | Leu | Leu | |
| | | 595 | | | | | 600 | | | | | 605 | | | | |
| AGT | AGT | GGA | AAT | ACA | AAA | CAA | TTG | AAG | AAC | AAA | GAG | GTC | GCT | GCC | TTG | 1992 |
| Ser | Ser | Gly | Asn | Thr | Lys | Gln | Leu | Lys | Asn | Lys | Glu | Val | Ala | Ala | Leu | |
| | 610 | | | | | 615 | | | | | 620 | | | | | |
| GTT | ATT | CAC | GGT | AAG | TTA | CCT | TTG | TAC | GCT | TTG | GAG | AAA | AAA | TTA | GGT | 2040 |
| Val | Ile | His | Gly | Lys | Leu | Pro | Leu | Tyr | Ala | Leu | Glu | Lys | Lys | Leu | Gly | |
| 625 | | | | | 630 | | | | | 635 | | | | | 640 | |
| GAT | ACT | ACG | AGA | GCG | GTT | GCG | GTA | CGT | AGG | AAG | GCT | CTT | TCA | ATT | TTG | 2088 |
| Asp | Thr | Thr | Arg | Ala | Val | Ala | Val | Arg | Arg | Lys | Ala | Leu | Ser | Ile | Leu | |
| | | | | 645 | | | | | 650 | | | | | 655 | | |
| GCA | GAA | GCT | CCT | GTA | TTA | GCA | TCT | GAT | CGT | TTA | CCA | TAT | AAA | AAT | TAT | 2136 |
| Ala | Glu | Ala | Pro | Val | Leu | Ala | Ser | Asp | Arg | Leu | Pro | Tyr | Lys | Asn | Tyr | |
| | | | 660 | | | | | 665 | | | | | 670 | | | |
| GAC | TAC | GAC | CGC | GTA | TTT | GGC | GCT | TGT | TGT | GAA | AAT | GTT | ATA | GGT | TAC | 2184 |
| Asp | Tyr | Asp | Arg | Val | Phe | Gly | Ala | Cys | Cys | Glu | Asn | Val | Ile | Gly | Tyr | |
| | | 675 | | | | | 680 | | | | | 685 | | | | |
| ATG | CCT | TTG | CCC | GTT | GGT | GTT | ATA | GGC | CCC | TTG | GT.T | ATC | GAT | GGT | ACA | 2232 |
| Met | Pro | Leu | Pro | Val | Gly | Val | Ile | Gly | Pro | Leu | Val | Ile | Asp | Gly | Thr | |
| | 690 | | | | | 695 | | | | | 700 | | | | | |
| TCT | TAT | CAT | ATA | CCA | ATG | GCA | ACT | ACA | GAG | GGT | TGT | TTG | GTA | GCT | TCT | 2280 |
| Ser | Tyr | His | Ile | Pro | Met | Ala | Thr | Thr | Glu | Gly | Cys | Leu | Val | Ala | Ser | |
| 705 | | | | | 710 | | | | | 715 | | | | | 720 | |
| GCC | ATG | CGT | GGC | TGT | AAG | GCA | ATC | AAT | GCT | GGC | GGT | GGT | GCA | ACA | ACT | 2328 |
| Ala | Met | Arg | Gly | Cys | Lys | Ala | Ile | Asn | Ala | Gly | Gly | Gly | Ala | Thr | Thr | |
| | | | | 725 | | | | | 730 | | | | | 735 | | |
| GTT | TTA | ACT | AAG | GAT | GGT | ATG | ACA | AGA | GGC | CCA | GTA | GTC | CGT | TTC | CCA | 2376 |
| Val | Leu | Thr | Lys | Asp | Gly | Met | Thr | Arg | Gly | Pro | Val | Val | Arg | Phe | Pro | |
| | | | 740 | | | | | 745 | | | | | 750 | | | |
| ACT | TTG | AAA | AGA | TCT | GGT | GCC | TGT | AAG | ATA | TGG | TTA | GAC | TCA | GAA | GAG | 2424 |
| Thr | Leu | Lys | Arg | Ser | Gly | Ala | Cys | Lys | Ile | Trp | Leu | Asp | Ser | Glu | Glu | |
| | | 755 | | | | | 760 | | | | | 765 | | | | |
| GGA | CAA | AAC | GCA | ATT | AAA | AAA | GCT | TTT | AAC | TCT | ACA | TCA | AGA | TTT | GCA | 2472 |
| Gly | Gln | Asn | Ala | Ile | Lys | Lys | Ala | Phe | Asn | Ser | Thr | Ser | Arg | Phe | Ala | |
| | 770 | | | | | 775 | | | | | 780 | | | | | |
| CGT | CTG | CAA | CAT | ATT | CAA | ACT | TGT | CTA | GCA | GGA | GAT | TTA | CTC | TTC | ATG | 2520 |
| Arg | Leu | Gln | His | Ile | Gln | Thr | Cys | Leu | Ala | Gly | Asp | Leu | Leu | Phe | Met | |
| 785 | | | | | 790 | | | | | 795 | | | | | 800 | |
| AGA | TTT | AGA | ACA | ACT | ACT | GGT | GAC | GCA | ATG | GGT | ATG | AAT | ATG | ATT | TCT | 2568 |
| Arg | Phe | Arg | Thr | Thr | Thr | Gly | Asp | Ala | Met | Gly | Met | Asn | Met | Ile | Ser | |
| | | | | 805 | | | | | 810 | | | | | 815 | | |
| AAA | GGT | GTC | GAA | TAC | TCA | TTA | AAG | CAA | ATG | GTA | GAA | GAG | TAT | GGC | TGG | 2616 |
| Lys | Gly | Val | Glu | Tyr | Ser | Leu | Lys | Gln | Met | Val | Glu | Glu | Tyr | Gly | Trp | |
| | | | 820 | | | | | 825 | | | | | 830 | | | |

| | | | | | | | | | | | | | | | | |
|---|---|---|---|---|---|---|---|---|---|---|---|---|---|---|---|---|
| GAA | GAT | ATG | GAG | GTT | GTC | TCC | GTT | TCT | GGT | AAC | TAC | TGT | ACC | GAC | AAA | 2664 |
| Glu | Asp | Met 835 | Glu | Val | Val | Ser | Val 840 | Ser | Gly | Asn | Tyr | Cys 845 | Thr | Asp | Lys | |
| AAA | CCA | GCT | GCC | ATC | AAC | TGG | ATC | GAA | GGT | CGT | GGT | AAG | AGT | GTC | GTC | 2712 |
| Lys | Pro 850 | Ala | Ala | Ile | Asn | Trp 855 | Ile | Glu | Gly | Arg | Gly 860 | Lys | Ser | Val | Val | |
| GCA | GAA | GCT | ACT | ATT | CCT | GGT | GAT | GTT | GTC | AGA | AAA | GTG | TTA | AAA | AGT | 2760 |
| Ala 865 | Glu | Ala | Thr | Ile | Pro 870 | Gly | Asp | Val | Val | Arg 875 | Lys | Val | Leu | Lys | Ser 880 | |
| GAT | GTT | TCC | GCA | TTG | GTT | GAG | TTG | AAC | ATT | GCT | AAG | AAT | TTG | GTT | GGA | 2808 |
| Asp | Val | Ser | Ala | Leu 885 | Val | Glu | Leu | Asn | Ile 890 | Ala | Lys | Asn | Leu | Val 895 | Gly | |
| TCT | GCA | ATG | GCT | GGG | TCT | GTT | GGT | GGA | TTT | AAC | GCA | CAT | GCA | GCT | AAT | 2856 |
| Ser | Ala | Met 900 | Ala | Gly | Ser | Val | Gly 905 | Gly | Phe | Asn | Ala | His 910 | Ala | Ala | Asn | |
| TTA | GTG | ACA | GCT | GTT | TTC | TTG | GCA | TTA | GGA | CAA | GAT | CCT | GCA | CAA | AAT | 2904 |
| Leu | Val | Thr 915 | Ala | Val | Phe | Leu | Ala 920 | Leu | Gly | Gln | Asp | Pro 925 | Ala | Gln | Asn | |
| GTT | GAA | AGT | TCC | AAC | TGT | ATA | ACA | TTG | ATG | AAA | GAA | GTG | GAC | GGT | GAT | 2952 |
| Val | Glu 930 | Ser | Ser | Asn | Cys | Ile 935 | Thr | Leu | Met | Lys | Glu 940 | Val | Asp | Gly | Asp | |
| TTG | AGA | ATT | TCC | GTA | TCC | ATG | CCA | TCC | ATC | GAA | GTA | GGT | ACC | ATC | GGT | 3000 |
| Leu 945 | Arg | Ile | Ser | Val | Ser 950 | Met | Pro | Ser | Ile | Glu 955 | Val | Gly | Thr | Ile | Gly 960 | |
| GGT | GGT | ACT | GTT | CTA | GAA | CCA | CAA | GGT | GCC | ATG | TTG | GAC | TTA | TTA | GGT | 3048 |
| Gly | Gly | Thr | Val | Leu 965 | Glu | Pro | Gln | Gly | Ala 970 | Met | Leu | Asp | Leu | Leu 975 | Gly | |
| GTA | AGA | GGC | CCG | CAT | GCT | ACC | GCT | CCT | GGT | ACC | AAC | GCA | CGT | CAA | TTA | 3096 |
| Val | Arg | Gly | Pro 980 | His | Ala | Thr | Ala | Pro 985 | Gly | Thr | Asn | Ala | Arg 990 | Gln | Leu | |
| GCA | AGA | ATA | GTT | GCC | TGT | GCC | GTC | TTG | GCA | GGT | GAA | TTA | TCC | TTA | TGT | 3144 |
| Ala | Arg | Ile 995 | Val | Ala | Cys | Ala | Val 1000 | Leu | Ala | Gly | Glu | Leu 1005 | Ser | Leu | Cys | |
| GCT | GCC | CTA | GCA | GCC | GGC | CAT | TTG | GTT | CAA | AGT | CAT | ATG | ACC | CAC | AAC | 3192 |
| Ala | Ala | Leu 1010 | Ala | Ala | Gly | His 1015 | Leu | Val | Gln | Ser | His 1020 | Met | Thr | His | Asn | |
| AGG | AAA | CCT | GCT | GAA | CCA | ACA | AAA | CCT | AAC | AAT | TTG | GAC | GCC | ACT | GAT | 3240 |
| Arg 1025 | Lys | Pro | Ala | Glu | Pro 1030 | Thr | Lys | Pro | Asn | Asn 1035 | Leu | Asp | Ala | Thr | Asp 1040 | |
| ATA | AAT | CGT | TTG | AAA | GAT | GGG | TCC | GTC | ACC | TGC | ATT | AAA | TCC | | | 3282 |
| Ile | Asn | Arg | Leu | Lys 1045 | Asp | Gly | Ser | Val | Thr 1050 | Cys | Ile | Lys | Ser | | | |

TAAACTTAGT CATACGTCAT TGGTATTCTC TTGAAAAAGA AGCACAACAG CACCATGTGT  3342

TACGTAAAAT ATTTACTT  3360

( 2 ) INFORMATION FOR SEQ ID NO:4:

( i ) SEQUENCE CHARACTERISTICS:
        ( A ) LENGTH: 1054 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met 1 | Pro | Pro | Xeu | Phe 5 | Lys | Gly | Leu | Lys | Gln 10 | Met | Ala | Lys | Pro | Ile 15 | Ala |
| Tyr | Val | Ser | Arg 20 | Phe | Ser | Ala | Lys | Arg 25 | Pro | Ile | His | Ile | Ile 30 | Leu | Phe |
| Ser | Leu | Ile | Ile | Ser | Ala | Phe | Ala | Tyr | Leu | Ser | Val | Ile | Gln | Tyr | Tyr |

-continued

|  |  |  | 35 |  |  |  |  | 40 |  |  |  |  | 45 |  |  |
|---|---|---|---|---|---|---|---|---|---|---|---|---|---|---|---|
| Phe | Asn | Gly | Trp | Gln | Leu | Asp | Ser | Asn | Ser | Val | Phe | Glu | Thr | Ala | Pro |
|  | 50 |  |  |  | 55 |  |  |  |  | 60 |  |  |  |  |  |
| Asn | Lys | Asp | Ser | Asn | Thr | Leu | Phe | Gln | Glu | Cys | Ser | His | Tyr | Tyr | Arg |
| 65 |  |  |  |  | 70 |  |  |  |  | 75 |  |  |  |  | 80 |
| Asp | Ser | Ser | Leu | Asp | Gly | Trp | Val | Ser | Ile | Thr | Ala | His | Glu | Ala | Ser |
|  |  |  |  | 85 |  |  |  |  | 90 |  |  |  |  | 95 |  |
| Glu | Leu | Pro | Ala | Pro | His | His | Tyr | Tyr | Leu | Leu | Asn | Leu | Asn | Phe | Asn |
|  |  |  | 100 |  |  |  |  | 105 |  |  |  |  | 110 |  |  |
| Ser | Pro | Asn | Glu | Thr | Asp | Ser | Ile | Pro | Glu | Leu | Ala | Asn | Thr | Val | Phe |
|  |  | 115 |  |  |  |  | 120 |  |  |  |  | 125 |  |  |  |
| Glu | Lys | Asp | Asn | Thr | Lys | Tyr | Ile | Leu | Gln | Glu | Asp | Leu | Ser | Val | Ser |
|  | 130 |  |  |  |  | 135 |  |  |  |  | 140 |  |  |  |  |
| Lys | Glu | Ile | Ser | Ser | Thr | Asp | Gly | Thr | Lys | Trp | Arg | Leu | Arg | Ser | Asp |
| 145 |  |  |  |  | 150 |  |  |  |  | 155 |  |  |  |  | 160 |
| Arg | Lys | Ser | Leu | Phe | Asp | Val | Lys | Thr | Leu | Ala | Tyr | Ser | Leu | Tyr | Asp |
|  |  |  |  | 165 |  |  |  |  | 170 |  |  |  |  | 175 |  |
| Val | Phe | Ser | Glu | Asn | Val | Thr | Gln | Ala | Asp | Pro | Phe | Asp | Val | Leu | Ile |
|  |  |  | 180 |  |  |  |  | 185 |  |  |  |  | 190 |  |  |
| Met | Val | Thr | Ala | Tyr | Leu | Met | Met | Phe | Tyr | Thr | Ile | Phe | Gly | Leu | Phe |
|  |  | 195 |  |  |  |  | 200 |  |  |  |  | 205 |  |  |  |
| Asn | Asp | Met | Arg | Lys | Thr | Gly | Ser | Asn | Phe | Trp | Leu | Ser | Ala | Ser | Thr |
| 210 |  |  |  |  | 215 |  |  |  |  | 220 |  |  |  |  |  |
| Val | Val | Asn | Ser | Ala | Ser | Ser | Leu | Phe | Leu | Ala | Leu | Tyr | Val | Thr | Gln |
| 225 |  |  |  |  | 230 |  |  |  |  | 235 |  |  |  |  | 240 |
| Cys | Ile | Leu | Gly | Lys | Glu | Val | Ser | Ala | Leu | Thr | Leu | Phe | Glu | Gly | Leu |
|  |  |  |  | 245 |  |  |  |  | 250 |  |  |  |  | 255 |  |
| Pro | Phe | Ile | Val | Val | Val | Gly | Phe | Lys | His | Lys | Ile | Lys | Ile | Ala |
|  |  |  | 260 |  |  |  |  | 265 |  |  |  |  | 270 |  |  |
| Gln | Tyr | Ala | Leu | Glu | Lys | Phe | Glu | Arg | val | Gly | Leu | Ser | Lys | Arg | Ile |
|  |  | 275 |  |  |  |  | 280 |  |  |  |  | 285 |  |  |  |
| Thr | Thr | Asp | Glu | Ile | Val | Phe | Glu | Ser | Val | Ser | Glu | Gly | Gly | Arg |
|  | 290 |  |  |  |  | 295 |  |  |  |  | 300 |  |  |  |  |
| Leu | Ile | Gln | Asp | His | Leu | Leu | Cys | Ile | Phe | Ala | Phe | Ile | Gly | Cys | Ser |
| 305 |  |  |  |  | 310 |  |  |  |  | 315 |  |  |  |  | 320 |
| Met | Tyr | Ala | His | Gln | Leu | Lys | Thr | Leu | Thr | Asn | Phe | Cys | Ile | Leu | Ser |
|  |  |  |  | 325 |  |  |  |  | 330 |  |  |  |  | 335 |  |
| Ala | Phe | Ile | Leu | Ile | Phe | Glu | Leu | Ile | Leu | Thr | Pro | Thr | Phe | Tyr | Ser |
|  |  |  | 340 |  |  |  |  | 345 |  |  |  |  | 350 |  |  |
| Ala | Ile | Leu | Ala | Leu | Arg | Leu | Glu | Met | Asn | Val | Ile | His | Arg | Ser | Thr |
|  |  |  | 355 |  |  |  |  | 360 |  |  |  |  | 365 |  |  |
| Ile | Ile | Lys | Gln | Thr | Leu | Glu | Glu | Asp | Gly | Val | Val | Pro | Ser | Thr | Ala |
|  |  | 360 |  |  |  |  | 375 |  |  |  |  | 380 |  |  |  |
| Arg | Ile | Ile | Ser | Lys | Ala | Glu | Lys | Lys | Ser | Val | Ser | Ser | Phe | Leu | Asn |
| 385 |  |  |  |  | 390 |  |  |  |  | 395 |  |  |  |  | 400 |
| Leu | Ser | Val | Val | Val | Ile | Ile | Met | Lys | Leu | Ser | Val | Ile | Leu | Leu | Phe |
|  |  |  |  | 405 |  |  |  |  | 410 |  |  |  |  | 415 |  |
| Val | Phe | Ile | Asn | Phe | Tyr | Asn | Phe | Gly | Ala | Asn | Trp | Val | Asn | Asp | Ala |
|  |  |  | 420 |  |  |  |  | 425 |  |  |  |  | 430 |  |  |
| Phe | Asn | Ser | Leu | Tyr | Phe | Asp | Lys | Glu | Arg | Val | Ser | Leu | Pro | Asp | Phe |
|  |  |  | 435 |  |  |  |  | 440 |  |  |  |  | 445 |  |  |
| Ile | Thr | Ser | Asn | Ala | Ser | Glu | Asn | Phe | Lys | Glu | Gln | Ala | Ile | Val | Ser |
|  | 440 |  |  |  |  | 455 |  |  |  |  | 460 |  |  |  |  |

-continued

| | | | | | | | | | | | | | | |
|---|---|---|---|---|---|---|---|---|---|---|---|---|---|---|
| Val<br>465 | Thr | Pro | Xcu | Xcu<br>470 | Tyr | Tyr | Lys | Pro | Ile<br>475 | Lys | Ser | Tyr | Gln | Arg | Ile<br>480 |
| Glu | Asp | met | Val | Leu<br>485 | Leu | Leu | Leu | Arg | Asn<br>490 | Val | Ser | Val | Ala | Ile<br>495 | Arg |
| Asp | Arg | Phe | Val<br>500 | Ser | LY8 | LSU | Val | Leu<br>505 | Ser | Ala | Leu | Val | Cys<br>510 | Ser | Ala |
| Val | Ile | Asn<br>515 | Val | Tyr | Leu | Leu | Asn<br>520 | Ala | Ala | Arg | Ile | His<br>525 | Thr | Ser | Tyr |
| Thr | Ala<br>530 | Asp | Gln | Leu | Val | Lys<br>535 | Thr | Glu | Val | Thr | Lys<br>540 | Lys | Ser | Phe | Thr |
| Ala<br>545 | Pro | Val | Gln | Lys | Ala<br>550 | Ser | Thr | Pro | Val | Leu<br>555 | Thr | Asn | Lys | Thr | Val<br>560 |
| Ile | Ser | Gly | Ser | Lys<br>565 | Val | Lys | Ser | Leu | Ser<br>570 | Ser | Ala | Gln | Ser | Ser<br>575 | Ser |
| Ser | Gly | Pro | Ser<br>580 | Ser | Ser | Ser | Glu | Glu<br>585 | Asp | Asp | Ser | Arg | Asp<br>590 | Ile | Glu |
| Ser | Leu | Asp<br>595 | Lys | Lys | Ile | Arg | Pro<br>600 | Leu | Glu | Glu | Leu | Glu<br>605 | Ala | Leu | Leu |
| Ser | Ser<br>610 | Gly | Asn | Thr | Lys | Gln<br>615 | Leu | Lys | Asn | Lys | Glu<br>620 | Val | Ala | Ala | Leu |
| Val<br>625 | Ile | His | Gly | Lys | Leu<br>630 | Pro | Leu | Tyr | Ala | Leu<br>635 | Glu | Lys | Lys | Leu | Gly<br>640 |
| Asp | Thr | Thr | Arg | Ala<br>645 | Val | Ala | Val | Arg | Arg<br>650 | Lys | Ala | Leu | Ser | Ile<br>655 | Leu |
| Ala | Glu | Ala | Pro<br>670 | Val | Leu | Ala | Ser | Asp<br>665 | Arg | Leu | Pro | Tyr | Lys<br>670 | Asn | Tyr |
| Asp | Tyr | Asp<br>675 | Arg | Val | Phe | Gly | Ala<br>680 | Cys | Cys | Glu | Asn | Val<br>685 | Ile | Gly | Tyr |
| Met | Pro<br>680 | Leu | Pro | Val | Gly | Val<br>695 | Ile | Gly | Pro | Leu | Val<br>700 | Ile | Asp | Gly | Thr |
| Ser<br>705 | Tyr | His | Ile | Pro | Met<br>710 | Ala | Thr | Thr | Glu | Gly<br>715 | Cys | Losu | Val | Ala | Ser<br>720 |
| Ala | Met | Arg | Gly | Cys<br>725 | Lys | Ala | Ile | Asn | Ala<br>730 | Gly | Gly | Gly | Ala | Thr<br>735 | Thr |
| Val | Leu | Thr | Lys<br>740 | Asp | Gly | Met | Thr | Arg<br>745 | Gly | Pro | Val | Val | Arg<br>750 | Phe | Pro |
| Thr | Leu | Lys<br>755 | Arg | Ser | Gly | Ala | Cys<br>760 | Lys | Ile | Trp | Leu | Asp<br>765 | Ser | Glu | Glu |
| Gly | Gln<br>770 | Ash | Ala | Ile | Lys<br>775 | Lys | Ala | Phe | Asn | Ser<br>780 | Thr | Ser | Arg | Phe | Ala |
| Arg<br>785 | Leu | Gln | His | Ile | Gln<br>790 | Thr | Cys | Leu | Ala | Gly<br>795 | Asp | Leu | Xocu | Phe | Met<br>800 |
| Arg | Phe | Arg | Thr | Thr<br>805 | Thr | Gly | Asp | Ala | Met<br>810 | Gly | Met | Asn | Met<br>815 | Ile | Ser |
| Lys | Gly | Val | Glu<br>820 | Tyr | Ser | Leu | Lys | Gln<br>825 | Met | Val | Glu | Glu | Tyr<br>830 | Gly | Trp |
| Glu | Asp | Met<br>835 | Glu | Val | Val | Ser | Val<br>840 | Ser | Gly | Asn | Tyr | Cys<br>845 | Thr | Asp | Lys |
| Lys | Pro<br>850 | Ala | Ala | Ile | Asn | Trp<br>855 | Ile | Glu | Gly | Arg | Gly<br>860 | Lys | Ser | Val | Val |
| Ala<br>865 | Glu | Ala | Thr | Ile | Pro<br>870 | Gly | Asp | Val | Val | Arg<br>875 | Lys | Val | Leu | Lys | Ser<br>880 |
| Asp | Val | Ser | Ala | Leu<br>885 | Val | Glu | Leu | Asn | Ile<br>890 | Ala | Lys | Asn | Leu | Val<br>895 | Gly |

| | | | | | | | | | | | | | | |
|---|---|---|---|---|---|---|---|---|---|---|---|---|---|---|
| Ser | Ala | Met | Ala | Gly | Ser | Val | Gly | Gly | Phe | Asn | Ala | His | Ala | Ala | Asn |
| | | | 900 | | | | | 905 | | | | 910 | | |
| Leu | Val | Thr | Ala | Val | Phe | Leu | Ala | Leu | Gly | Gln | Asp | Pro | Ala | Gln | Asn |
| | | 915 | | | | 920 | | | | | 925 | | | |
| Val | Glu | Ser | Ser | Asn | Cys | Ile | Thr | Leu | Met | Lys | Glu | Val | Asp | Gly | Asp |
| | 930 | | | | | 935 | | | | | 940 | | | |
| Leu | Arg | Ile | Ser | Val | Ser | Met | Pro | Ser | Ile | Glu | Val | Gly | Thr | Ile | Gly |
| 945 | | | | | 950 | | | | | 955 | | | | 960 |
| Gly | Gly | Thr | Val | Leu | Glu | Pro | Gln | Gly | Ala | Met | Leu | Asp | Leu | Leu | Gly |
| | | | | 965 | | | | | | 970 | | | | 975 |
| Val | Arg | Gly | Pro | His | Ala | Thr | Ala | Pro | Gly | Thr | Asn | Ala | Arg | Gln | Leu |
| | | | 980 | | | | | | 985 | | | | | 990 |
| Ala | Arg | Ile | Val | Ala | Cys | Ala | Val | Leu | Ala | Gly | Glu | Leu | Ser | Leu | Cys |
| | | | 995 | | | | | 1000 | | | | | 1005 | |
| Ala | Ala | Leu | Ala | Ala | Gly | His | Leu | Val | Gln | Ser | His | Met | Thr | His | Asn |
| | 1010 | | | | | | 1015 | | | | | 1020 | | |
| Arg | Lys | Pro | Ala | Glu | Pro | Thr | Lys | Pro | Asn | Asn | Leu | Asp | Ala | Thr | Asp |
| 1025 | | | | | 1030 | | | | | 1035 | | | | | 1040 |
| Ile | Asn | Arg | Xeu | Lys | Asp | Gly | Ser | Val | Thr | Cys | Ile | Lys | Ser | | |
| | | | | 1045 | | | | | 1050 | | | | | | |

( 2 ) INFORMATION FOR SEQ ID NO:5:

( i ) SEQUENCE CHARACTERISTICS:
        ( A ) LENGTH: 3348 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 121..3255

( x i ) SEQUENCE DESCRIPTION: SEQ ID NO:5:

```
GGAATATTTT GTACGAGCAA GTTATAGTAA GACACTTCAG TGAGAAATTA ATCTGACTTA        60

CTTTTACTTA ATTGTGTTCT TTCCAAATTA GTTCAACAAG GTTCCCACAT ACAACCTCAA       120
```

| | | | | | | | | | | | | | | | | |
|---|---|---|---|---|---|---|---|---|---|---|---|---|---|---|---|---|
| ATG | TCA | CTT | CCC | TTA | AAA | ACG | ATA | GTA | CAT | TTG | GTA | AAG | CCC | TTT | GCT | 168 |
| Met | Ser | Leu | Pro | Leu | Lys | Thr | Ile | Val | His | Leu | Val | Lys | Pro | Phe | Ala | |
| 1 | | | | 5 | | | | | 10 | | | | | 15 | | |
| TGC | ACT | GCT | AGG | TTT | AGT | GCG | AGA | TAC | CCA | ATC | CAC | GTC | ATT | GTT | GTT | 216 |
| Cys | Thr | Ala | Arg | Phe | Ser | Ala | Arg | Tyr | Pro | Ile | His | Val | Ile | Val | Val | |
| | | | 20 | | | | | 25 | | | | | 30 | | | |
| GCT | GTT | TTA | TTG | AGT | GCC | GCT | GCT | TAT | cTA | TCC | GTG | ACA | CAA | TCT | TAC | 264 |
| Ala | Val | Leu | Leu | Ser | Ala | Ala | Ala | Tyr | Leu | Ser | Val | Thr | Gln | Ser | Tyr | |
| | | | 35 | | | | | 40 | | | | | 45 | | | |
| CTT | AAC | GAA | TGG | AAG | CTG | GAC | TCT | AAT | CAG | TAT | TCT | ACA | TAC | TTA | AGC | 312 |
| Leu | Asn | Glu | Trp | Lys | Leu | Asp | Ser | Asn | Gln | Tyr | Ser | Thr | Tyr | Leu | Ser | |
| | | 50 | | | | | 55 | | | | | 60 | | | | |
| ATA | AAG | CCG | GAT | GAG | TTG | TTT | GAA | AAA | TGC | ACA | CAC | TAC | TAT | AGG | TCT | 360 |
| Ile | Lys | Pro | Asp | Glu | Leu | Phe | Glu | Lys | Cys | Thr | His | Tyr | Tyr | Arg | Ser | |
| 65 | | | | | 70 | | | | | 75 | | | | | 80 | |
| CCT | GTG | TCT | GAT | ACA | TGG | AAG | TTA | CTC | AGC | TCT | AAA | GAA | GCC | GCC | GAT | 408 |
| Pro | Val | Ser | Asp | Thr | Trp | Lys | Leu | Leu | Ser | Ser | LYS | Glu | Ala | Ala | Asp | |
| | | | | 85 | | | | | 90 | | | | | 95 | | |
| ATT | TAT | ACC | CCT | TTT | CAT | TAT | TAT | TTG | TCT | ACC | ATA | AGT | TTT | CAA | AGT | 456 |
| Ile | Tyr | Thr | Pro | Phe | His | Tyr | Tyr | Leu | Ser | Thr | Ile | Ser | Phe | Gln | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| AAG | GAC | AAT | TCA | ACG | ACT | TTG | CCT | TCC | CTT | GAT | GAC | GTT | ATT | TAC | AGT | 504 |
| Lys | Asp | Asn | Ser | Thr | Thr | Leu | Pro | Ser | Leu | Asp | Asp | Val | Ile | Tyr | Ser | |
| | | 115 | | | | | 120 | | | | | 125 | | | | |
| GTT | GAC | CAT | ACC | AGG | TAC | TTA | TTA | AGT | GAA | GAG | CCA | AAG | ATA | CCA | ACT | 552 |
| Val | Asp | His | Thr | Arg | Tyr | Leu | Leu | Ser | Glu | Glu | Pro | Lys | Ile | Pro | Thr | |
| | 130 | | | | | 135 | | | | | 140 | | | | | |
| GAA | CTA | GTG | TCT | GAA | AAC | GGA | ACG | AAA | TGG | AGA | TTG | AGA | AAC | AAC | AGC | 600 |
| Glu | Leu | Val | Ser | Glu | Asn | Gly | Thr | Lys | Trp | Arg | Leu | Arg | Asn | Asn | Ser | |
| 145 | | | | | 150 | | | | | 155 | | | | | 160 | |
| AAT | TTT | ATT | TTG | GAC | CTG | CAT | AAT | ATT | TAC | CGA | AAT | ATG | GTG | AAG | CAA | 648 |
| Asn | Phe | Ile | Leu | Asp | Leu | His | Asn | Ile | Tyr | Arg | Asn | Met | Val | Lys | Gln | |
| | | | | 165 | | | | | 170 | | | | | 175 | | |
| TTT | TCT | AAC | AAA | ACG | AGC | GAA | TTT | GAT | CAG | TTC | GAT | TTG | TTT | ATC | ATC | 696 |
| Phe | Ser | Asn | Lys | Thr | Ser | Glu | Phe | Asp | Gln | Phe | Asp | Leu | Phe | Ile | Ile | |
| | | | 180 | | | | | 185 | | | | | 190 | | | |
| CTA | GCT | GCT | TAC | CTT | ACT | CTT | TTT | TAT | ACT | CTC | TGT | TGC | CTG | TTT | AAT | 744 |
| Leu | Ala | Ala | Tyr | Leu | Thr | Leu | Phe | Tyr | Thr | Leu | Cys | Cys | Leu | Phe | Asn | |
| | | 195 | | | | | 200 | | | | | 205 | | | | |
| GAC | ATG | AGG | AAA | ATC | GGA | TCA | AAG | TTT | TGG | TTA | AGC | TTT | TCT | GCT | CrT | 792 |
| Asp | Met | Arg | Lys | Ile | Gly | Ser | Lys | Phe | Trp | Leu | Ser | Phe | Ser | Ala | Leu | |
| | 210 | | | | | 215 | | | | | 220 | | | | | |
| TCA | AAC | TCT | GCA | TGC | GCA | TTA | TAT | TTA | TCG | CTG | TAC | ACA | ACT | CAC | AGT | 840 |
| Ser | Asn | Ser | Ala | Cys | Ala | Leu | Tyr | Leu | Ser | Leu | Tyr | Thr | Thr | His | Ser | |
| 225 | | | | | 230 | | | | | 235 | | | | | 240 | |
| TTA | TTG | AAG | AAA | CCG | GCT | TCC | TTA | TTA | AGT | TTG | GTC | ATT | GGA | CTA | CCA | 888 |
| Leu | Leu | Lys | Lys | Pro | Ala | Ser | Leu | Leu | Ser | Leu | Val | Ile | Gly | Leu | Pro | |
| | | | | 245 | | | | | 250 | | | | | 255 | | |
| TTT | ATC | GTA | GTA | ATT | ATT | GGC | TTT | AAG | CAT | AAA | GTT | CGA | CTT | GCG | GCA | 936 |
| Phe | Ile | Val | Val | Ile | Ile | Gly | Phe | Lys | His | Lys | Val | Arg | Leu | Ala | Ala | |
| | | | 260 | | | | | 265 | | | | | 270 | | | |
| TTC | TCG | CTA | CAA | AAA | TTC | CAC | AGA | ATT | AGT | ATT | GAC | AAG | AAA | ATA | ACG | 984 |
| Phe | Ser | Leu | Gln | Lys | Phe | His | Arg | Ile | Ser | Ile | Asp | Lys | Lys | Ile | Thr | |
| | | 275 | | | | | 280 | | | | | 285 | | | | |
| GTA | AGC | AAC | ATT | ATT | TAT | GAG | GCT | ATG | TTT | CAA | GAA | GGT | GCC | TAC | TTA | 1032 |
| Val | Ser | Asn | Ile | Ile | Tyr | Glu | Ala | Met | Phe | Gln | Glu | Gly | Ala | Tyr | Leu | |
| | 290 | | | | | 295 | | | | | 300 | | | | | |
| ATC | CGC | GAC | TAC | TTA | TTT | TAT | ATT | AGC | TCC | TTC | ATT | GGA | TGT | GCT | ATT | 1080 |
| Ile | Arg | Asp | Tyr | Leu | Phe | Tyr | Ile | Ser | Ser | Phe | Ile | Gly | Cys | Ala | Ile | |
| 305 | | | | | 310 | | | | | 315 | | | | | 320 | |
| TAT | GCT | AGA | CAT | CTT | CCC | GGA | TTG | GTC | AAT | TTC | TGT | ATT | TTG | TCT | ACA | 1128 |
| Tyr | Ala | Arg | His | Leu | Pro | Gly | Leu | Val | Asn | Phe | Cys | Ile | Leu | Ser | Thr | |
| | | | | 325 | | | | | 330 | | | | | 335 | | |
| TTT | ATG | CTA | GTT | TTC | GAC | TTG | CTT | TTG | TCT | GCT | ACT | TTT | TAT | TCT | GCC | 1176 |
| Phe | Met | Leu | Val | Phe | Asp | Leu | Leu | Leu | Ser | Ala | Thr | Phe | Tyr | Ser | Ala | |
| | | | 340 | | | | | 345 | | | | | 350 | | | |
| ATT | TTA | TCA | ATG | AAG | CTG | GAA | ATT | AAC | ATC | ATT | CAC | AGA | TCA | ACC | GTC | 1224 |
| Ile | Leu | Ser | Met | Lys | Leu | Glu | Ile | Asn | Ile | Ile | His | Arg | Ser | Thr | Val | |
| | | 355 | | | | | 360 | | | | | 365 | | | | |
| ATC | AGA | CAG | ACT | TTG | GAA | GAG | GAC | GGA | GTT | GTC | CCA | ACT | ACA | GCA | GAT | 1272 |
| Ile | Arg | Gln | Thr | Leu | Glu | Glu | Asp | Gly | Val | Val | Pro | Thr | Thr | Ala | Asp | |
| | 370 | | | | | 375 | | | | | 380 | | | | | |
| ATT | ATA | TAT | AAG | GAT | GAA | ACT | GCC | TCA | GAA | CCA | CAT | TTT | TTG | AGA | TCT | 1320 |
| Ile | Ile | Tyr | Lys | Asp | Glu | Thr | Ala | Ser | Glu | Pro | His | Phe | Leu | Arg | Ser | |
| 385 | | | | | 390 | | | | | 395 | | | | | 400 | |
| AAC | GTG | GCT | ATC | ATT | CTG | GGA | AAA | GCA | TCA | GTT | ATT | GGT | CTT | TTG | CTT | 1368 |
| Asn | Val | Ala | Ile | Ile | Leu | Gly | Lys | Ala | Ser | Val | Ile | Gly | Leu | Leu | Leu | |
| | | | | 405 | | | | | 410 | | | | | 415 | | |
| CTG | ATC | AAC | CTT | TAT | GIRT | TTC | ACA | GAT | AAG | TTA | AAT | GCT | ACA | ATA | CTA | 1416 |
| Leu | Ile | Asn | Leu | Tyr | Val | Phe | Thr | Asp | Lys | Leu | Asn | Ala | Thr | Ile | Leu | |
| | | | 420 | | | | | 425 | | | | | 430 | | | |

| | | | | | | | | | | | | | | | | |
|---|---|---|---|---|---|---|---|---|---|---|---|---|---|---|---|---|
|AAC|ACG|GTA|TAT|TTT|GAC|TCT|ACA|ATT|TAC|TCG|TTA|CCA|AAT|TTT|ATC|1464|
|Asn|Thr|Val 435|Tyr|Phe|Asp|Ser|Thr 440|Ile|Tyr|Ser|Leu|Pro 445|Asn|Phe|Ile| |

| | | | | | | | | | | | | | | | | |
|---|---|---|---|---|---|---|---|---|---|---|---|---|---|---|---|---|
|AAT|TAT|AAA|GAT|ATT|GGC|AAT|CTC|AGC|AAT|CAA|GTG|ATC|ATT|TCC|GTG|1512|
|Asn|Tyr 450|Lys|Asp|Ile|Gly|Asn 455|Leu|Ser|Asn|Gln|Val 460|Ile|Ile|Ser|Val| |

| | | | | | | | | | | | | | | | | |
|---|---|---|---|---|---|---|---|---|---|---|---|---|---|---|---|---|
|TTG|CCA|AAG|CAA|TAT|TAT|ACT|CCG|CTG|AAA|AAA|TAC|CAT|CAG|ATC|GAA|1560|
|Leu 465|Pro|Lys|Gln|Tyr|Tyr 470|Thr|Pro|Leu|Lys|Lys 475|Tyr|His|Gln|Ile|Glu 480| |

| | | | | | | | | | | | | | | | | |
|---|---|---|---|---|---|---|---|---|---|---|---|---|---|---|---|---|
|GAT|TCT|GTT|CTA|CTT|ATC|ATT|GAT|TCC|GTT|AGC|AAT|GCT|ATT|CGG|GAC|1608|
|Asp|Ser|Val|Leu|Leu 485|Ile|Ile|Asp|Ser|Val 490|Ser|Asn|Ala|Ile|Arg 495|Asp| |

| | | | | | | | | | | | | | | | | |
|---|---|---|---|---|---|---|---|---|---|---|---|---|---|---|---|---|
|CAA|TTT|ATC|AGC|AAG|TTA|CTT|TTT|TTT|GCA|TTT|GCA|GTT|AGT|ATT|TCC|1656|
|Gln|Phe|Ile|Ser 500|Lys|Leu|Leu|Phe|Phe 505|Ala|Phe|Ala|Val|Ser 510|Ile|Ser| |

| | | | | | | | | | | | | | | | | |
|---|---|---|---|---|---|---|---|---|---|---|---|---|---|---|---|---|
|ATC|AAT|GTC|TAC|TTA|CTG|AAT|GCT|GCA|AAA|ATT|CAC|ACA|GGA|TAC|ATG|1704|
|Ile|Asn|Val 515|Tyr|Leu|Leu|Asn|Ala 520|Ala|Lys|Ile|His|Thr 525|Gly|Tyr|Met| |

| | | | | | | | | | | | | | | | | |
|---|---|---|---|---|---|---|---|---|---|---|---|---|---|---|---|---|
|AAC|TTC|CAA|CCA|CAA|TCA|AAT|AAG|ATC|GAT|GAT|CTT|GTT|GTT|CAG|CAA|1752|
|Asn|Phe 530|Gln|Pro|Gln|Ser|Asn 535|Lys|Ile|Asp|Asp|Leu 540|Val|Val|Gln|Gln| |

| | | | | | | | | | | | | | | | | |
|---|---|---|---|---|---|---|---|---|---|---|---|---|---|---|---|---|
|AAA|TCG|GCA|ACG|ATT|GAG|TTT|TCA|GAA|ACT|CGA|AGT|ATG|CCT|GCT|TCT|1800|
|Lys 545|Ser|Ala|Thr|Ile|Glu 550|Phe|Ser|Glu|Thr|Arg 555|Ser|Met|Pro|Ala|Ser 560| |

| | | | | | | | | | | | | | | | | |
|---|---|---|---|---|---|---|---|---|---|---|---|---|---|---|---|---|
|TCT|GGC|CTA|GAA|ACT|CCA|GTG|ACC|GCG|AAA|GAT|ATA|ATT|ATC|TCT|GAA|1848|
|Ser|Gly|Leu|Glu|Thr 565|Pro|Val|Thr|Ala|Lys 570|Asp|Ile|Ile|Ile|Ser 575|Glu| |

| | | | | | | | | | | | | | | | | |
|---|---|---|---|---|---|---|---|---|---|---|---|---|---|---|---|---|
|GAA|ATC|CAG|AAT|AAC|GAA|TGC|GTC|TAT|GCT|TTG|AGT|TCC|CAG|GAC|GAG|1896|
|Glu|Ile|Gln|Asn 580|Asn|Glu|Cys|Val|Tyr 585|Ala|Leu|Ser|Ser|Gln 590|Asp|Glu| |

| | | | | | | | | | | | | | | | | |
|---|---|---|---|---|---|---|---|---|---|---|---|---|---|---|---|---|
|CCT|ATC|CGT|CCT|TTA|TCG|AAT|TTA|GTG|GAA|CTT|ATG|GAG|AAA|GAA|CAA|1944|
|Pro|Ile|Arg 595|Pro|Leu|Ser|Asn|Leu 600|Val|Glu|Leu|Met|Glu 605|Lys|Glu|Gln| |

| | | | | | | | | | | | | | | | | |
|---|---|---|---|---|---|---|---|---|---|---|---|---|---|---|---|---|
|TTA|AAG|AAC|ATG|AAT|AAT|ACT|GAG|GTT|TCG|AAT|CTT|GTC|GTC|AAC|GGT|1992|
|Leu|Lys|Asn|Met 610|Asn|Asn|Thr|Glu|Val 615|Ser|Asn|Leu|Val|Val 620|Asn|Gly| |

| | | | | | | | | | | | | | | | | |
|---|---|---|---|---|---|---|---|---|---|---|---|---|---|---|---|---|
|AAA|CTG|CCA|TTA|TAT|TCC|TTA|GAG|AAA|AAA|TTA|GAG|GAC|ACA|ACT|CGT|2040|
|Lys 625|Leu|Pro|Leu|Tyr|Ser 630|Leu|Glu|Lys|Lys|Leu 635|Glu|Asp|Thr|Thr|Arg 640| |

| | | | | | | | | | | | | | | | | |
|---|---|---|---|---|---|---|---|---|---|---|---|---|---|---|---|---|
|GCG|GTT|TTA|GTT|AGG|AGA|AAG|GCA|CTT|TCA|ACT|TTG|GCT|GAA|TCG|CCA|2088|
|Ala|Val|Leu|Val|Arg 645|Arg|Lys|Ala|Leu|Ser 650|Thr|Leu|Ala|Glu|Ser 655|Pro| |

| | | | | | | | | | | | | | | | | |
|---|---|---|---|---|---|---|---|---|---|---|---|---|---|---|---|---|
|ATT|TTA|GTT|TCC|GAA|AAA|TTG|CCC|TTC|AGA|AAT|TAT|GAT|TAT|GAT|CGC|2136|
|Ile|Leu|Val|Ser 660|Glu|Lys|Leu|Pro|Phe 665|Arg|Asn|Tyr|Asp|Tyr 670|Asp|Arg| |

| | | | | | | | | | | | | | | | | |
|---|---|---|---|---|---|---|---|---|---|---|---|---|---|---|---|---|
|GTT|TTT|GGA|GCT|TGC|TGT|GAA|AAT|GTC|ATC|GGC|TAT|ATG|CCA|ATA|CCA|2184|
|Val|Phe|Gly 675|Ala|Cys|Cys|Glu|Asn 680|Val|Ile|Gly|Tyr|Met 685|Pro|Ile|Pro| |

| | | | | | | | | | | | | | | | | |
|---|---|---|---|---|---|---|---|---|---|---|---|---|---|---|---|---|
|GTT|GGT|GTA|ATT|GGT|CcA|TTA|ATT|ATT|GAT|GGA|ACA|TCT|TAT|CAC|ATA|2232|
|Val|Gly|Val 690|Ile|Gly|Pro|Leu|Ile 695|Ile|Asp|Gly|Thr|Ser 700|Tyr|His|Ile| |

| | | | | | | | | | | | | | | | | |
|---|---|---|---|---|---|---|---|---|---|---|---|---|---|---|---|---|
|CCA|ATG|GCA|ACC|ACG|GAA|GGT|TGT|TTA|GTG|GCT|TCA|GCT|ATG|CGT|GGT|2280|
|Pro|Met|Ala|Thr 705|Thr|Glu|Gly|Cys|Leu 710|Val|Ala|Ser|Ala|Met 715|Arg|Gly 720| |

| | | | | | | | | | | | | | | | | |
|---|---|---|---|---|---|---|---|---|---|---|---|---|---|---|---|---|
|TGC|AAA|GCC|ATC|AAT|GCT|GGT|GGT|GGT|GCA|ACA|ACT|GTT|TTA|ACC|AAA|2328|
|Cys|Lys|Ala|Ile|Asn 725|Ala|Gly|Gly|Gly|Ala 730|Thr|Thr|Val|Lau|Thr 735|Lys| |

| | | | | | | | | | | | | | | | | |
|---|---|---|---|---|---|---|---|---|---|---|---|---|---|---|---|---|
|GAT|GGT|ATG|ACT|AGA|GGC|CCA|GTC|GTT|CGT|TTC|CCT|ACT|TTA|ATA|AGA|2376|
|Asp|Gly|Met|Thr 740|Arg|Gly|Pro|Val|Val 745|Arg|Phe|Pro|Thr|Leu 750|Ile|Arg| |

| | | | | | | | | | | | | | | | | |
|---|---|---|---|---|---|---|---|---|---|---|---|---|---|---|---|---|
| TCT | GGT | GCC | TGC | AAG | ATA | TGG | TTA | GAC | TCG | GAA | GAG | GGA | CAA | AAT | TCA | 2424 |
| Ser | Gly | Ala | Cys | Lys | Ile | Trp | Leu | Asp | Ser | Glu | Glu | Gly | Gln | Asn | Ser | |
| | | 755 | | | | 760 | | | | | 765 | | | | | |
| ATT | AAA | AAA | GCT | TTT | AAT | TCT | ACA | TCA | AGG | TTT | GCA | CGT | TTG | CAA | CAT | 2472 |
| Ile | Lys | Lys | Ala | Phe | Asn | Ser | Thr | Ser | Arg | Phe | Ala | Arg | Leu | Gln | His | |
| 770 | | | | | 775 | | | | | 780 | | | | | | |
| ATT | CAA | ACC | TGT | CTA | GCA | GGC | GAT | TTG | CTT | TTT | ATG | AGA | TTT | CGG | ACA | 2520 |
| Ile | Gln | Thr | Cys | Leu | Ala | Gly | Asp | Leu | Leu | Phe | Met | Arg | Phe | Arg | Thr | |
| 785 | | | | | 790 | | | | | 795 | | | | | 800 | |
| ACT | ACC | GGT | GAC | GCA | ATG | GGT | ATG | AAC | ATG | ATA | TCG | AAA | GGT | GTC | GAA | 2568 |
| Thr | Thr | Gly | Asp | Ala | Met | Gly | Met | Asn | Met | Ile | Ser | Lys | Gly | Val | Glu | |
| | | | | 805 | | | | | 810 | | | | | 815 | | |
| TAC | TCT | TTG | AAA | CAA | ATG | GTA | GAA | GAA | TAT | GGT | TGG | GAA | GAT | ATG | GAA | 2616 |
| Tyr | Ser | Leu | Lys | Gln | Met | Val | Glu | Glu | Tyr | Gly | Trp | Glu | Asp | Met | Glu | |
| | | | 820 | | | | | 825 | | | | | 830 | | | |
| GTT | GTC | TCC | GTA | TCT | GGT | AAC | TAT | TGT | ACT | GAT | AAG | AAk | CCT | GCC | GCA | 2664 |
| Val | Val | Ser | Val | Ser | Gly | Asn | Tyr | Cys | Thr | Asp | Lys | Lys | Pro | Ala | Ala | |
| | | 835 | | | | | 840 | | | | | 845 | | | | |
| ATC | AAT | TGG | ATT | GAA | GGT | CGT | GGT | AAA | AGT | GTC | GTA | GCT | GAA | GCT | ACT | 2712 |
| Ile | Asn | Trp | Ile | Glu | Gly | Arg | Gly | Lys | Ser | Val | Val | Ala | Glu | Ala | Thr | |
| | 850 | | | | | 855 | | | | | 860 | | | | | |
| ATT | CCT | GGT | GAT | GTC | GTA | AAA | AGT | GTT | TTA | AAG | AGC | GAT | GTT | TCC | GCT | 2760 |
| Ile | Pro | Gly | Asp | Val | Val | Lys | Ser | Val | Leu | Lys | Ser | Asp | Val | Ser | Ala | |
| 865 | | | | | 870 | | | | | 875 | | | | | 880 | |
| TTA | GTT | GAA | TTA | AAT | ATA | TCC | AAG | AAC | TTG | GTT | GGA | TCC | GCA | ATG | GCT | 2808 |
| Leu | Val | Glu | Leu | Asn | Ile | Ser | Lys | Asn | Leu | Val | Gly | Ser | Ala | Met | Ala | |
| | | | | 885 | | | | | 890 | | | | | 895 | | |
| GGA | TCT | GTT | GGT | GGT | TTC | AAC | GCG | CAC | GCA | GCT | AAT | TTG | GTC | ACT | GCA | 2856 |
| Gly | Ser | Val | Gly | Gly | Phe | Asn | Ala | His | Ala | Ala | Asn | Leu | Val | Thr | Ala | |
| | | | 900 | | | | | 905 | | | | | 910 | | | |
| CTT | TTC | TTG | GCA | TTA | GGC | CAA | GAT | CCT | GCG | CAG | AAC | GTC | GAA | AGT | TCC | 2904 |
| Leu | Phe | Leu | Ala | Leu | Gly | Gln | Asp | Pro | Ala | Gln | Asn | Val | Glu | Ser | Ser | |
| | | 915 | | | | | 920 | | | | | 925 | | | | |
| AAC | TGT | ATA | ACT | TTG | ATG | AAG | GAA | GTT | GAT | GGT | GAT | TTA | AGG | ATC | TCT | 2952 |
| Asn | Cys | Ile | Thr | Leu | Met | Lys | Glu | Val | Asp | Gly | Asp | Leu | Arg | Ile | Ser | |
| | 930 | | | | | 935 | | | | | 940 | | | | | |
| GTT | TCC | ATG | CCA | TCT | ATT | GAA | GTT | GGT | ACG | ATT | GGC | GGG | GGT | ACT | GTT | 3000 |
| Val | Ser | Met | Pro | Ser | Ile | Glu | Val | Gly | Thr | Ile | Gly | Gly | Gly | Thr | Val | |
| 945 | | | | | 950 | | | | | 955 | | | | | 960 | |
| CTG | GAG | CCT | CAG | GGC | GCC | ATG | CTT | GAT | CTT | CTC | GGC | GTT | CGT | GGT | CCT | 3048 |
| Leu | Glu | Pro | Gln | Gly | Ala | Met | Leu | Asp | Leu | Leu | Gly | Val | Arg | Gly | Pro | |
| | | | | 965 | | | | | 970 | | | | | 975 | | |
| CAC | CCC | ACT | GAA | CCT | GGA | GCA | AAT | GCT | AGG | CAA | TTA | GCT | AGA | ATA | ATC | 3096 |
| His | Pro | Thr | Glu | Pro | Gly | Ala | Asn | Ala | Arg | Gln | Leu | Ala | Arg | Ile | Ile | |
| | | | 980 | | | | | 985 | | | | | 990 | | | |
| GCG | TGT | GCT | GTC | TTG | GCT | GGT | GAA | CTG | TCT | CTG | TGC | TCC | GCA | CTT | GCT | 3144 |
| Ala | Cys | Ala | Val | Leu | Ala | Gly | Glu | Leu | Ser | Leu | Cys | Ser | Ala | Leu | Ala | |
| | | 995 | | | | | 1000 | | | | | 1005 | | | | |
| GCC | GGT | CAC | CTG | GTA | CAA | AGC | CAT | ATG | ACT | CAC | AAC | CGT | AAA | ACA | AAC | 3192 |
| Ala | Gly | His | Leu | Val | Gln | Ser | His | Met | Thr | His | Asn | Arg | Lys | Thr | Asn | |
| | 1010 | | | | | 1015 | | | | | 1020 | | | | | |
| AAA | GCC | AAT | GAA | CTG | CCA | CAA | CCA | AGT | AAC | AAA | GGG | CCC | CCC | TGT | AAA | 3240 |
| Lys | Ala | Asn | Glu | Leu | Pro | Gln | Pro | Ser | Asn | Lys | Gly | Pro | Pro | Cys | Lys | |
| 1025 | | | | | 1030 | | | | | 1035 | | | | | 1040 | |
| ACC | TCA | GCA | TTA | TTA | TAACTCTTGT | AGTTACATG | GTGATACTTT | ATATCTTTGT | | | | | | | | 3295 |
| Thr | Ser | Ala | Leu | Leu | | | | | | | | | | | | |
| | | | 1045 | | | | | | | | | | | | | |

ATTGTCTAGC TATTCTAAAT CATCTGCATG TAATAAGAAG TTGATCAAAA TGA                3348

( 2 ) INFORMATION FOR SEQ ID NO:6:

(i) SEQUENCE CHARACTERISTICS:
    (A) LENGTH: 1045 amino acids
    (B) TYPE: amino acid
    (D) TOPOLOGY: linear (ii) MOLECULE TYPE: protein (xi) SEQUENCE DESCRIPTION: SEQ ID NO:6:

| Met | Ser | Leu | Pro | Leu | Lys | Thr | Ile | Val | His | Leu | Val | Lys | Pro | Phe | Ala |
|---|---|---|---|---|---|---|---|---|---|---|---|---|---|---|---|
| 1 | | | | 5 | | | | | 10 | | | | | 15 | |
| Cys | Thr | Ala | Arg | Phe | Ser | Ala | Arg | Tyr | Pro | Ile | His | Val | Ile | Val | Val |
| | | | 20 | | | | | 25 | | | | | 30 | | |
| Ala | Val | Leu | Leu | Ser | Ala | Ala | Ala | Tyr | Leu | Ser | Val | Thr | Gln | Ser | Tyr |
| | | | 35 | | | | 40 | | | | | 45 | | | |
| Leu | Asn | Glu | Trp | Lys | Leu | Asp | Ser | Asn | Gln | Tyr | Ser | Thr | Tyr | Leu | Ser |
| | | 50 | | | | | 55 | | | | | 60 | | | |
| Ile | Lys | Pro | Asp | Glu | Leu | Phe | Glu | Lys | Cys | Thr | His | Tyr | Tyr | Arg | Ser |
| 65 | | | | | 70 | | | | | 75 | | | | | 80 |
| Pro | Val | Ser | Asp | Thr | Trp | Lys | Leu | Leu | Ser | Ser | Lys | Glu | Ala | Ala | Asp |
| | | | | 85 | | | | | 90 | | | | | 95 | |
| Ile | Tyr | Thr | Pro | Phe | His | Tyr | Tyr | Leu | Ser | Thr | Ile | Ser | Phe | Gln | Ser |
| | | | 100 | | | | | 105 | | | | | 110 | | |
| Lys | Asp | Asn | Ser | Thr | Thr | Leu | Pro | Ser | Leu | Asp | Asp | Val | Ile | Tyr | Ser |
| | | | 115 | | | | | 120 | | | | | 125 | | |
| Val | Asp | His | Thr | Arg | Tyr | Leu | Leu | Ser | Glu | Glu | Pro | Lys | Ile | Pro | Thr |
| | | | 130 | | | | | 135 | | | | | 140 | | |
| Glu | Leu | Val | Ser | Glu | Asn | Gly | Thr | Lys | Trp | Arg | Leu | Arg | Asn | Asn | Ser |
| 145 | | | | | 150 | | | | | 155 | | | | | 160 |
| Asn | Phe | Ile | Leu | Asp | Leu | His | Asn | Ile | Tyr | Arg | Asn | Met | Val | Lys | Gln |
| | | | | 165 | | | | | 170 | | | | | 175 | |
| Phe | Ser | Asn | Lys | Thr | Ser | Glu | Phe | Asp | Gln | Phe | Asp | Leu | Phe | Ile | Ile |
| | | | | 180 | | | | | 185 | | | | | 190 | |
| Leu | Ala | Ala | Tyr | Leu | Thr | Leu | Phe | Tyr | Thr | Leu | Cys | Cys | Leu | Phe | Asn |
| | | | | 195 | | | | | 200 | | | | | 205 | |
| Asp | Met | Arg | Lys | Ile | Gly | Ser | Lys | Phe | Trp | Leu | Ser | Phe | Ser | Ala | Leu |
| | | | 210 | | | | | 215 | | | | | 220 | | |
| Ser | Asn | Ser | Ala | Cys | Ala | Leu | Tyr | Leu | Ser | Leu | Tyr | Thr | Thr | His | Ser |
| 225 | | | | | 230 | | | | | 235 | | | | | 240 |
| Leu | Leu | Lys | Lys | Pro | Ala | Ser | Leu | Leu | Ser | Leu | Val | Ile | Gly | Leu | Pro |
| | | | | 245 | | | | | 250 | | | | | 255 | |
| Phe | Ile | Val | Val | Ile | Ile | Gly | Phe | Lys | His | Lys | Val | Arg | Leu | Ala | Ala |
| | | | | 260 | | | | | 265 | | | | | 270 | |
| Phe | Ser | Leu | Gln | Lys | Phe | His | Arg | Ile | Ser | Ile | Asp | Lys | Lys | Ile | Thr |
| | | | 275 | | | | | 280 | | | | | 285 | | |
| Val | Ser | Asn | Ile | Ile | Tyr | Glu | Ala | Met | Phe | Gln | Glu | Gly | Ala | Tyr | Leu |
| | | 290 | | | | | 295 | | | | | 300 | | | |
| Ile | Arg | Asp | Tyr | Leu | Phe | Tyr | Ile | Ser | Ser | Phe | Ile | Gly | cys | Ala | Ile |
| 310 | | | | | 315 | | | | | 320 | | | | | |
| Tyr | Ala | Arg | His | Leu | Pro | Gly | Leu | Val | Asn | Phe | Cys | Ile | Leu | Ser | Thr |
| | | | | 325 | | | | | 330 | | | | | 335 | |
| Phe | Met | Leu | Val | Phe | Asp | Leu | Leu | Leu | Ser | Ala | Thr | Phe | Tyr | Ser | Ala |
| | | | 340 | | | | | 345 | | | | | 350 | | |
| Ile | Leu | Ser | Met | Lys | Leu | Glu | Ile | Asn | Ile | Ile | His | Arg | Ser | Thr | Val |
| | | 355 | | | | | 360 | | | | | 365 | | | |
| Ile | Arg | Gln | Thr | Leu | Glu | Glu | Asp | Gly | Val | Val | Pro | Thr | Thr | Ala | Asp |

|     |     |     |     |     | 370 |     |     |     | 375 |     |     |     |     | 380 |
|---|---|---|---|---|---|---|---|---|---|---|---|---|---|---|

Ile Ile Tyr Lys Asp Glu Thr Ala Ser Glu Pro His Phe Leu Arg Ser
390                 395             400

Asn Val Ala Ile Ile Leu Gly Lys Ala Ser Val Ile Gly Leu Leu Leu
            405             410             415

Leu Ile Asn Leu Tyr Val Phe Thr Asp Lys Leu Asn Ala Thr Ile Leu
        420             425             430

Asn Thr Val Tyr Phe Asp Ser Thr Ile Tyr Ser Leu Pro Asn Phe Ile
        435             440             445

Asn Tyr Lys Asp Ile Gly Asn Leu Ser Asn Gln Val Ile Ile Ser Val
    450             455             460

Leu Pro Lys Gln Tyr Tyr Thr Pro Leu Lys Lys Tyr His Gln Ile Glu
465             470             475                         480

Asp Ser Val Leu Leu Ile Ile Asp Ser Val Ser Asn Ala Ile Arg Asp
                485             490             495

Gln Phe Ile Ser Lys Leu Leu Phe Phe Ala Phe Ala Val Ser Ile Ser
            500             505             510

Ile Asn Val Tyr Leu Leu Asn Ala Ala Lys Ile His Thr Gly Tyr Met
        515             520             525

Asn Phe Gln Pro Gln Ser Asn Lys Ile Asp Asp Leu Val Val Gln Gln
    530             535             540

Lys Ser Ala Thr Ile Glu Phe Ser Glu Thr Arg Ser Met Pro Ala Ser
545             550             555             560

Ser Gly Leu Glu Thr Pro Val Thr Ala Lys Asp Ile Ile Ile Ser Glu
            565             570             575

Glu Ile Gln Asn Asn Glu Cys Val Tyr Ala Leu Ser Ser Gln Asp Glu
            580             585             590

Pro Ile Arg Pro Leu Ser Asn Leu Val Glu Leu Met Glu Lys Glu Gln
        595             600             605

Leu Lys Asn Met Asn Asn Thr Glu Val Ser Asn Leu Val Val Asn Gly
    610             615             620

Lys Leu Pro Leu Tyr Ser Leu Glu Lys Lys Leu Glu Asp Thr Thr Arg
625             630             635             640

Ala Val Leu Val Arg Arg Lys Ala Leu Ser Thr Leu Ala Glu Ser Pro
            645             650             655

Ile Leu Val Ser Glu Lys Leu Pro Phe Arg Asn Tyr Asp Tyr Asp Arg
            660             665             670

Val Phe Gly Ala Cys Cys Glu Asn Val Ile Gly Tyr Met Pro Ile Pro
        675             680             685

Val Gly Val Ile Gly Pro Leu Ile Ile Asp Gly Thr Ser Tyr His Ile
    690             695             700

Pro Met Ala Thr Thr Glu Gly Cys Leu Val Ala Ser Ala Met Arg Gly
705             710             715             720

Cys Lys Ala Ile Asn Ala Gly Gly Gly Ala Thr Thr Val Leu Thr Lys
            725             730             735

Asp Gly Met Thr Arg Gly Pro Val Val Arg Phe Pro Thr Leu Ile Arg
            740             745             750

Ser Gly Ala Cys Lys Ile Trp Leu Asp Ser Glu Glu Gly Gln Asn Ser
        755             760             765

Ile Lys Lys Ala Phe Asn Ser Thr Ser Arg Phe Ala Arg Leu Gln His
    770             775             780

Ile Gln Thr Cys Leu Ala Gly Asp Leu Leu Phe Met Arg Phe Arg Thr
785             790             795             800

```
Thr  Thr  Gly  Asp  Ala  Met  Gly  Met  Asn  Met  Ile  Ser  Lys  Gly  Val  Glu
               805                      810                      815

Tyr  Ser  Leu  Lys  Gln  Met  Val  Glu  Glu  Tyr  Gly  Trp  Glu  Asp  Met  Glu
               820                 825                      830

Val  Val  Ser  Val  Ser  Gly  Asn  Tyr  Cys  Thr  Asp  Lys  Lys  Pro  Ala  Ala
          835                 840                      845

Ile  Asn  Trp  Ile  Glu  Gly  Arg  Gly  Lys  Ser  Val  Val  Ala  Glu  Ala  Thr
     840                      855                      860

Ile  Pro  Gly  Asp  Val  Val  Lys  Ser  Val  Leu  Lys  Ser  Asp  Val  Ser  Ala
865                      870                 875                           880

Leu  Val  Glu  Leu  Asn  Ile  Ser  Lys  Asn  Leu  Val  Gly  Ser  Ala  Met  Ala
               885                      890                           895

Gly  Ser  Val  Gly  Gly  Phe  Asn  Ala  His  Ala  Ala  Asn  Leu  Val  Thr  Ala
               900                 905                      910

Leu  Phe  Leu  Ala  Leu  Gly  Gln  Asp  Pro  Ala  Gln  Asn  Val  Glu  Ser  Ser
          915                 920                      925

Asn  Cys  Ile  Thr  Leu  Met  Lys  Glu  Val  Asp  Gly  Asp  Leu  Arg  Ile  Ser
     930                 935                      940

Val  Ser  Met  Pro  Ser  Ile  Glu  Val  Gly  Thr  Ile  Gly  Gly  Gly  Thr  Val
945                      950                 955                           960

Leu  Glu  Pro  Gln  Gly  Ala  Met  Leu  Asp  Leu  Leu  Gly  Val  Arg  Gly  Pro
               965                      970                      975

His  Pro  Thr  Glu  Pro  Gly  Ala  Asn  Ala  Arg  Gln  Leu  Ala  Arg  Ile  Ile
               980                 985                      990

Ala  Cys  Ala  Val  Leu  Ala  Gly  Glu  Leu  Ser  Leu  Cys  Ser  Ala  Leu  Ala
          995                 1000                     1005

Ala  Gly  His  Leu  Val  Gln  Ser  His  Met  Thr  His  Asn  Arg  Lys  Thr  Asn
     1010                     1015                     1020

Lys  Ala  Asn  Glu  Leu  Pro  Gln  Pro  Ser  Asn  Lys  Gly  Pro  Pro  Cys  Lys
1025                     1030                     1035                     1040

Thr  Ser  Ala  Leu  Leu
               1045
```

We claim:

1. A process of increasing squalene accumulation in a transgenic plant comprising:
   (a) transforming a plant cell with a recombinant DNA molecule comprising a vector operatively linked to a DNA segment that encodes a polypeptide having HMG-CoA reductase activity, and a promoter suitable for driving the expression of said polypeptide in said plant cell to form a transformed plant cell; and
   (b) regenerating said transformed plant cell into said transgenic plant.

2. The process according to claim 1 wherein said polypeptide comprises the catalytic region and at least a portion of the linker region but is free from the membrane binding region of a HMG-CoA reductase.

3. The process according to claim 1 wherein the promoter is a promoter whose regulatory function is substantially unaffected by the level of squalene in said transgenic plant.

4. The process according to claim 1 wherein the promoter is the CaMV 35S promoter.

5. The process according to claim 1 wherein said plant cell is obtained from plants of the group consisting of tobacco, cotton, soybean, tomato and alfalfa.

6. A transgenic plant produced in accordance with the process of claim 1.

7. A transgenic plant seed transformed with a vector comprising a DNA segment that encodes a polypeptide having HMG-CoA reductase activity, and a promoter suitable for driving the expression of said polypeptide in said plant cell, wherein said transgenic plant seed is capable of germinating into a transgenic plant that over accumulates squalene relative to a native, non-transgenic plant of the same strain; and mutants, recombinants, genetically engineered derivatives thereof and hybrids derived therefrom, wherein said mutants, recombinants, genetically engineered derivatives thereof and hybrids derived therefrom maintain the ability to overaccumulate squalene.

* * * * *

UNITED STATES PATENT AND TRADEMARK OFFICE
CERTIFICATE OF CORRECTION

PATENT NO.: 5,589,619

DATED: December 31, 1996

INVENTOR(S): Joseph Chappell, Court A. Saunders, Fred R. Wolf

It is certified that error appears in the above-identified patent and that said Letters Patent is hereby corrected as shown below:

Patent reads:

| Col. | Line | |
|---|---|---|
| 2 | 22 | reads "Exemplary naturally occurring delta-5 plant sterols isofucosterol..." <br> should read --Exemplary naturally occurring delta-5 plant sterols are isofucosterol...-- |
| 6 | 36 | reads "(Gramineae,..." <br> should read --(Gramineae),...-- |
| 10 | 4 | reads "weight of 53kDa segment and..." <br> should read --weight of 53 kDa and-- |
| 10 | 29 | reads "A truncated hamster HMG-CoA reductase gene, designated" <br> should read --A truncated hamster HMG-CoA reductase gene is designated-- |

UNITED STATES PATENT AND TRADEMARK OFFICE
CERTIFICATE OF CORRECTION

PATENT NO.: 5,589,619

DATED: December 31, 1996

INVENTOR(S): Joseph Chappell, Court A. Saunders, Fred R. Wolf

It is certified that error appears in the above-identified patent and that said Letters Patent is hereby corrected as shown below:

Patent reads:

| Col. | Line | |
|---|---|---|
| 21 | 60 | reads "... Dr. J.L. Goldstein, See, e.g.,"<br>should read --...Dr. J.L. Goldstein. See, e.g.,-- |
| 22 | 12 | reads "HMRGΔ-KLYX71"<br>should read --HMRGΔ-pKLYX71-- |
| 22 | 28 | reads "HMGR Δ-227-KYLX71"<br>should read --HMGRΔ227-pKYLX71-- |
| 22 | 37 | reads "Δ227-pKYLX71"<br>should read --HMGRΔ227-pKYLX71-- |
| 26 | 50 | reads "HMGR 227-KYLX71"<br>should read --HMGRΔ227-pKYLX71-- |
| 37- | | SEQ ID NO: 2, sequence numbers are misaligned, |

Signed and Sealed this

Ninth Day of February, 1999

*Attest:*

*Attesting Officer*

*Acting Commissioner of Patents and Trademarks*

(ii) MOLECULE TYPE: protein (xi) SEQUENCE DESCRIPTION: SEQ ID NO:2:

```
Met Leu Ser Arg Leu Phe Arg Met His Gly Leu Phe Val Ala Ser His
 1               5                  10                      15

Pro Trp Glu Val Ile Val Gly Thr Val Thr Leu Thr Ile Cys Met Met
            20                  25                      30

Ser Met Asn Met Phe Thr Gly Asn Asn Lys Ile Cys Gly Trp Asn Tyr
        35                  40                  45

Glu Cys Pro Lys Phe Glu Glu Asp Val Leu Ser Ser Asp Ile Ile Ile
    50                  55                  60

Leu Thr Ile Thr Arg Cys Ile Ala Ile Leu Tyr Ile Tyr Phe Gln Phe
65                  70                  75                      80

Gln Asn Leu Arg Gln Leu Gly Ser Lys Tyr Ile Leu Gly Ile Ala Gly
                85                  90                      95

Leu Phe Thr Ile Phe Ser Ser Phe Val Phe Ser Thr Val Val Ile His
            100                 105                     110

Phe Leu Asp Lys Glu Leu Thr Gly Leu Asn Glu Ala Leu Pro Phe Phe
            115                 120                 125

Leu Leu Leu Ile Asp Leu Ser Arg Ala Ser Ala Leu Ala Lys Phe Ala
130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                165                 170                 175

Leu Val Ile Gly Val Gly Thr Met Ser Gly Val Arg Gln Leu Glu Ile
                180                 185                 190

Met Cys Cys Phe Gly Cys Met Ser Val Leu Ala Asn Tyr Phe Val Phe
            195                 200                 205

Met Thr Phe Phe Pro Ala Cys Val Ser Leu Val Leu Glu Leu Ser Arg
210                 215                 220

Glu Ser Arg Glu Gly Arg Pro Ile Trp Gln Leu Ser His Phe Ala Arg
225                 230                 235                 240

Val Leu Glu Glu Glu Glu Asn Lys Pro Asn Pro Val Thr Gln Arg Val
                245                 250                 255
```

```
Lys Met Ile Met Ser Leu Gly Leu Val Leu Val His Ala His Ser Arg
        260                 265             270

Trp Ile Ala Asp Pro Ser Pro Gln Asn Ser Thr Thr Glu His Ser Lys
    275                 280             285

Val Ser Leu Gly Leu Asp Glu Asp Val Ser Lys Arg Ile Glu Pro Ser
    290             295             300

Val Ser Leu Trp Gln Phe Tyr Leu Ser Lys Met Ile Ser Met Asp Ile
305             310             315             320

Glu Gln Val Val Thr Leu Ser Leu Ala Phe Leu Leu Ala Val Lys Tyr
                325             330             335

Ile Phe Phe Glu Gln Ala Glu Thr Glu Ser Thr Leu Ser Leu Lys Asn
            340             345             350

Pro Ile Thr Ser Pro Val Val Thr Pro Lys Lys Ala Pro Asp Asn Cys
        355             360             365

Cys Arg Arg Glu Pro Leu Leu Val Arg Arg Ser Glu Lys Leu Ser Ser
    370             375             380

Val Glu Glu Glu Pro Gly Val Ser Gln Asp Arg Lys Val Glu Val Ile
385             390             395             400

Lys Pro Leu Val Val Glu Thr Glu Ser Ala Ser Arg Ala Thr Phe Val
            405             410             415

Leu Gly Ala Ser Gly Thr Ser Pro Pro Val Ala Ala Arg Thr Gln Glu
        420             425             430

Leu Glu Ile Glu Leu Pro Ser Glu Pro Arg Pro Asn Glu Glu Cys Leu
        435             440             445

Gln Ile Leu Glu Ser Ala Glu Lys Gly Ala Lys Phe Leu Ser Asp Ala
    450             455             460

Glu Ile Ile Gln Leu Val Asn Ala Lys His Ile Pro Ala Tyr Lys Leu
465             470             475             480

Glu Thr Leu Met Glu Thr His Glu Arg Gly Val Ser Ile Arg Arg Gln
            485             490             495

Leu Leu Ser Thr Lys Leu Pro Glu Pro Ser Ser Leu Gln Tyr Leu Pro
        500             505             510

Tyr Arg Asp Tyr Asn Tyr Ser Leu Val Met Gly Ala Cys Cys Glu Asn
    515             520             525
```

Val Ile Gly Tyr Met Pro Ile Pro Val Gly Val Ala Gly Pro Leu Cys
530                     535                 540

Leu Asp Gly Lys Glu Tyr Gln Val Pro Met Ala Thr Thr Glu Gly Cys
545                 550                 555                 560

Leu Val Ala Ser Thr Asn Arg Gly Cys Arg Ala Ile Gly Leu Gly Gly
                565                 570                 575

Gly Ala Ser Ser Arg Val Leu Ala Asp Gly Met Thr Arg Gly Pro Val
            580                 585                 590

Val Arg Leu Pro Arg Ala Cys Asp Ser Ala Glu Val Lys Ala Trp Leu
        595                 600                 605

Glu Thr Pro Glu Gly Phe Ala Val Ile Lys Asp Ala Phe Asp Ser Thr
    610                 615                 620

Ser Arg Phe Ala Arg Leu Gln Lys Leu His Val Thr Met Ala Gly Arg
625                 630                 635                 640

Asn Leu Tyr Ile Arg Phe Gln Ser Lys Thr Gly Asp Ala Met Gly Met
                645                 650                 655

Asn Met Ile Ser Lys Gly Thr Glu Lys Ala Leu Leu Lys Leu Gln Glu
            660                 665                 670

Phe Phe Pro Glu Met Gln Ile Leu Ala Val Ser Gly Asn Tyr Cys Thr
        675                 680                 685

Asp Lys Lys Pro Ala Ala Ile Asn Trp Ile Glu Gly Arg Gly Lys Thr
    690                 695                 700

Val Val Cys Glu Ala Val Ile Pro Ala Lys Val Val Arg Glu Val Leu
705                 710                 715                 720

Lys Thr Thr Thr Glu Ala Met Ile Asp Val Asn Ile Asn Lys Asn Leu
                725                 730                 735

Val Gly Ser Ala Met Ala Gly Ser Ile Gly Gly Tyr Asn Ala His Ala
            740                 745                 750

Ala Asn Ile Val Thr Ala Ile Tyr Ile Ala Cys Gly Gln Asp Ala Ala
        755                 760                 765

Gln Asn Val Gly Ser Ser Asn Cys Ile Thr Leu Met Glu Ala Ser Gly
    770                 775                 780

Pro Thr Asn Glu Asp Leu Tyr Ile Ser Cys Thr Met Pro Ser Ile Glu
785                 790                 795                 800

70

Ile Gly Thr Val Gly Gly Gly Thr Asn Leu Leu Pro Gln Gln Ala Cys
                    805                 810                 815
Leu Gln Met Leu Gly Val Gln Gly Ala Cys Lys Asp Asn Pro Gly Glu
            820                 825                 830
Asn Ala Arg Gln Leu Ala Arg Ile Val Cys Gly Thr Val Met Ala Gly
        835                 840                 845
Glu Leu Ser Leu Met Ala Ala Leu Ala Ala Gly His Leu Val Arg Ser
850                 855                 860
His Met Val His Asn Arg Ser Lys Ile Asn Leu Gln Asp Leu Gln Gly
865             870                 875                 880
Thr Cys Thr Lys Lys Ser Ala
                885